(12) United States Patent
Alexander et al.

(10) Patent No.: US 9,694,121 B2
(45) Date of Patent: Jul. 4, 2017

(54) SYSTEMS AND METHODS FOR IMPROVING CARDIAC FUNCTION

(71) Applicant: CardioKinetix, Inc., Menlo Park, CA (US)

(72) Inventors: Miles D. Alexander, Fremont, CA (US); Matthew L. Pease, Mountain View, CA (US); Barry L Templin, San Jose, CA (US); Serjan D. Nikolic, San Francisco, CA (US)

(73) Assignee: CardioKinetix, Inc., Menlo Park, CA (US)

( * ) Notice: Subject to any disclaimer, the term of this patent is extended or adjusted under 35 U.S.C. 154(b) by 461 days.

(21) Appl. No.: 14/189,856

(22) Filed: Feb. 25, 2014

(65) Prior Publication Data

US 2014/0179993 A1 Jun. 26, 2014

Related U.S. Application Data

(63) Continuation-in-part of application No. 11/801,075, filed on May 7, 2007, now Pat. No. 8,657,873, which
(Continued)

(51) Int. Cl.
*A61F 2/24* (2006.01)
*A61M 1/10* (2006.01)
(Continued)

(52) U.S. Cl.
CPC ............ *A61M 1/10* (2013.01); *A61B 17/0057* (2013.01); *A61B 17/12022* (2013.01);
(Continued)

(58) Field of Classification Search
CPC .............. A61F 2/2487; A61F 2002/249; A61F 2/0063; A61F 2002/0068; A61M 1/12; A61M 1/125
See application file for complete search history.

(56) References Cited

U.S. PATENT DOCUMENTS 3,874,388 A * 4/1975 King .................. A61B 17/0057
606/213
4,007,743 A 2/1977 Blake
(Continued)

FOREIGN PATENT DOCUMENTS

EP 1474032 A2 11/2004
EP 2068768 A 6/2009
(Continued)

OTHER PUBLICATIONS

Sojitra et al.; Electropolishing of 316LVM stainless steel cardiovascular stents: an investigation of material removal, surface roughness and corrosion behaviour; Trends Biomater. Artif. Organs; 23(3); pp. 115-121; (year of pub. sufficiently earlier than effective US filing date and any foreign priority date) 2010.
(Continued)

*Primary Examiner* — Katrina Stransky
*Assistant Examiner* — Wade P Schutte
(74) *Attorney, Agent, or Firm* — Shay Glenn LLP

(57) ABSTRACT

A system for improving cardiac function is provided. A foldable and expandable frame having at least one anchoring formation is attached to an elongate manipulator and placed in a catheter tube while folded. The tube is inserted into a left ventricle of a heart where the frame is ejected from the tube and expands in the left ventricle. Movements of the elongate manipulator cause the anchor to penetrate the heart muscle and the elongate manipulator to release the frame. The installed frame minimizes the effects of an akinetic portion of the heart forming an aneurysmic bulge. Devices and methods are described herein which are directed to the treatment of a patient's heart having, or one which is susceptible to heart failure, to improve diastolic function.

30 Claims, 55 Drawing Sheets

Related U.S. Application Data is a continuation of application No. 10/436,959, filed on May 12, 2003, now Pat. No. 8,257,428, which is a continuation-in-part of application No. 09/635,511, filed on Aug. 9, 2000, now abandoned, application No. 14/189,856, filed on Feb. 25, 2014, which is a continuation-in-part of application No. 12/691,587, filed on Jan. 21, 2010, now Pat. No. 8,672,827, which is a continuation of application No. 11/640,469, filed on Dec. 14, 2006, now Pat. No. 7,674,222, which is a continuation-in-part of application No. 10/212,033, filed on Aug. 1, 2002, now Pat. No. 7,303,526, which is a continuation-in-part of application No. 09/635,511, filed on Aug. 9, 2000, now abandoned.

(60) Provisional application No. 60/147,894, filed on Aug. 9, 1999, provisional application No. 61/816,628, filed on Apr. 26, 2013.

(51) Int. Cl.
*A61B 17/00* (2006.01)
*A61B 17/12* (2006.01)
*A61B 17/064* (2006.01)

(52) U.S. Cl.
CPC .. *A61B 17/12122* (2013.01); *A61B 17/12172* (2013.01); *A61B 2017/00243* (2013.01); *A61B 2017/00575* (2013.01); *A61B 2017/00579* (2013.01); *A61B 2017/00592* (2013.01); *A61B 2017/00597* (2013.01); *A61B 2017/00615* (2013.01); *A61B 2017/00632* (2013.01); *A61B 2017/00867* (2013.01); *A61B 2017/0649* (2013.01); *A61B 2017/12095* (2013.01)

(56) References Cited

U.S. PATENT DOCUMENTS

| | | |
|---|---|---|
| 4,425,908 A | 1/1984 | Simon |
| 4,453,545 A | 6/1984 | Inoue |
| 4,536,893 A | 8/1985 | Parravicini |
| 4,588,404 A | 5/1986 | Lapeyre |
| 4,619,246 A | 10/1986 | Molgaard-Nielsen et al. |
| 4,685,446 A | 8/1987 | Choy |
| 4,710,192 A | 12/1987 | Liotta et al. |
| 4,819,751 A | 4/1989 | Shimada et al. |
| 4,832,055 A | 5/1989 | Palestrant |
| 4,917,089 A | 4/1990 | Sideris |
| 4,983,165 A | 1/1991 | Loiterman |
| 5,104,399 A | 4/1992 | Lazarus |
| 5,192,301 A | 3/1993 | Kamiya et al. |
| 5,192,314 A * | 3/1993 | Daskalakis ...... A61B 17/12022 623/3.21 |
| 5,258,000 A | 11/1993 | Gianturco |
| 5,375,612 A | 12/1994 | Cottenceau et al. |
| 5,385,156 A | 1/1995 | Oliva |
| 5,389,087 A | 2/1995 | Miraki |
| 5,425,744 A | 6/1995 | Fagan et al. |
| 5,433,727 A | 7/1995 | Sideris |
| 5,451,235 A | 9/1995 | Lock et al. |
| 5,496,277 A | 3/1996 | Termin et al. |
| 5,527,337 A | 6/1996 | Stack et al. |
| 5,527,338 A | 6/1996 | Purdy |
| 5,549,621 A | 8/1996 | Bessler et al. |
| 5,551,435 A | 9/1996 | Sramek |
| 5,578,069 A | 11/1996 | Miner, II |
| 5,634,936 A | 6/1997 | Linden et al. |
| 5,634,942 A | 6/1997 | Chevillon et al. |
| 5,647,870 A | 7/1997 | Kordis et al. |
| 5,702,343 A | 12/1997 | Alferness |
| 5,709,707 A | 1/1998 | Lock et al. |
| 5,758,664 A | 6/1998 | Campbell et al. |
| 5,791,231 A | 8/1998 | Cohn et al. |
| 5,797,849 A | 8/1998 | Vesely et al. |
| 5,797,960 A | 8/1998 | Stevens et al. |
| 5,800,457 A | 9/1998 | Gelbfish |
| 5,800,517 A | 9/1998 | Anderson et al. |
| 5,829,447 A | 11/1998 | Stevens et al. |
| 5,833,682 A | 11/1998 | Amplatz et al. |
| 5,833,698 A | 11/1998 | Hinchliffe et al. |
| 5,836,968 A | 11/1998 | Simon et al. |
| 5,843,170 A | 12/1998 | Ahn |
| 5,860,951 A | 1/1999 | Eggers et al. |
| 5,861,003 A | 1/1999 | Latson et al. |
| 5,865,730 A | 2/1999 | Fox et al. |
| 5,865,791 A | 2/1999 | Whayne et al. |
| 5,871,017 A | 2/1999 | Mayer |
| 5,875,782 A | 3/1999 | Ferrari et al. |
| 5,876,325 A | 3/1999 | Mizuno et al. |
| 5,876,449 A | 3/1999 | Starck et al. |
| 5,879,366 A | 3/1999 | Shaw et al. |
| 5,882,340 A | 3/1999 | Yoon |
| 5,910,150 A | 6/1999 | Saadat |
| 5,916,145 A | 6/1999 | Chu et al. |
| 5,924,424 A | 7/1999 | Stevens et al. |
| 5,925,062 A | 7/1999 | Purdy |
| 5,925,076 A | 7/1999 | Inoue |
| 5,928,260 A | 7/1999 | Chin et al. |
| 5,961,440 A | 10/1999 | Schweich, Jr. et al. |
| 5,961,539 A | 10/1999 | Northrup, III et al. |
| 5,984,917 A | 11/1999 | Fleischman et al. |
| 6,024,096 A | 2/2000 | Buckberg |
| 6,024,756 A | 2/2000 | Huebsch et al. |
| 6,036,720 A | 3/2000 | Abrams et al. |
| 6,045,497 A | 4/2000 | Schweich, Jr. et al. |
| 6,059,715 A | 5/2000 | Schweich, Jr. et al. |
| 6,076,013 A | 6/2000 | Brennan et al. |
| 6,077,214 A | 6/2000 | Mortier et al. |
| 6,077,218 A | 6/2000 | Alferness |
| 6,093,199 A | 7/2000 | Brown et al. |
| 6,095,968 A | 8/2000 | Snyders |
| 6,096,347 A | 8/2000 | Geddes et al. |
| 6,099,832 A | 8/2000 | Mickle et al. |
| 6,102,887 A | 8/2000 | Altman |
| 6,125,852 A | 10/2000 | Stevens et al. |
| 6,132,438 A | 10/2000 | Fleischman et al. |
| 6,142,973 A | 11/2000 | Carleton et al. |
| 6,152,144 A * | 11/2000 | Lesh ............... A61B 17/0057 128/898 |
| 6,155,968 A | 12/2000 | Wilk |
| 6,156,027 A | 12/2000 | West |
| 6,161,543 A | 12/2000 | Cox et al. |
| 6,193,731 B1 | 2/2001 | Oppelt et al. |
| 6,221,092 B1 | 4/2001 | Koike et al. |
| 6,221,104 B1 | 4/2001 | Buckberg et al. |
| 6,230,714 B1 | 5/2001 | Alferness et al. |
| 6,231,561 B1 | 5/2001 | Frazier et al. |
| 6,258,021 B1 | 7/2001 | Wilk |
| 6,267,772 B1 | 7/2001 | Mulhauser et al. |
| 6,290,674 B1 | 9/2001 | Roue et al. |
| 6,296,656 B1 | 10/2001 | Bolduc et al. |
| 6,312,446 B1 | 11/2001 | Huebsch et al. |
| 6,328,727 B1 | 12/2001 | Frazier et al. |
| 6,334,864 B1 | 1/2002 | Amplatz et al. |
| 6,343,605 B1 | 2/2002 | Lafontaine |
| 6,348,068 B1 | 2/2002 | Campbell et al. |
| 6,355,052 B1 | 3/2002 | Neuss et al. |
| 6,360,749 B1 | 3/2002 | Jayaraman |
| 6,364,896 B1 | 4/2002 | Addis |
| 6,387,042 B1 | 5/2002 | Herrero |
| 6,406,420 B1 | 6/2002 | McCarthy et al. |
| 6,419,669 B1 | 7/2002 | Frazier et al. |
| 6,436,088 B2 | 8/2002 | Frazier et al. |
| 6,450,171 B1 | 9/2002 | Buckberg et al. |
| 6,482,146 B1 | 11/2002 | Alferness et al. |
| 6,482,228 B1 | 11/2002 | Norred |
| 6,506,204 B2 | 1/2003 | Mazzocchi |
| 6,508,756 B1 | 1/2003 | Kung et al. |
| 6,511,496 B1 | 1/2003 | Huter et al. |
| 6,537,198 B1 | 3/2003 | Vidlund et al. |
| 6,551,303 B1 | 4/2003 | Van Tassel et al. |
| 6,572,643 B1 | 6/2003 | Gharibadeh |

(56) References Cited

U.S. PATENT DOCUMENTS

| | | |
|---|---|---|
| 6,586,414 B2 | 7/2003 | Haque et al. |
| 6,592,608 B2 | 7/2003 | Fisher et al. |
| 6,613,013 B2 | 9/2003 | Haarala et al. |
| 6,622,730 B2 | 9/2003 | Ekvall et al. |
| 6,645,199 B1 | 11/2003 | Jenkins et al. |
| 6,652,555 B1 | 11/2003 | Van Tassel et al. |
| 6,681,773 B2 | 1/2004 | Murphy et al. |
| 6,685,627 B2 | 2/2004 | Jayaraman |
| 6,702,763 B2 | 3/2004 | Murphy et al. |
| 6,730,108 B2 | 5/2004 | Van Tassel et al. |
| 6,776,754 B1 | 8/2004 | Wilk |
| 6,852,076 B2 | 2/2005 | Nikolic et al. |
| 6,887,192 B1 | 5/2005 | Whayne et al. |
| 6,951,534 B2 | 10/2005 | Girard et al. |
| 6,959,711 B2 | 11/2005 | Murphy et al. |
| 6,994,093 B2 | 2/2006 | Murphy et al. |
| 7,144,363 B2 | 12/2006 | Pai et al. |
| 7,172,551 B2 | 2/2007 | Leasure |
| 7,175,660 B2 | 2/2007 | Cartledge et al. |
| 7,279,007 B2 | 10/2007 | Nikolic et al. |
| 7,303,526 B2 | 12/2007 | Sharkey et al. |
| 7,320,665 B2 | 1/2008 | Vijay |
| 7,399,271 B2 | 7/2008 | Sharkey et al. |
| 7,485,088 B2 | 2/2009 | Murphy et al. |
| 7,530,998 B1 | 5/2009 | Starkey |
| 7,569,062 B1 | 8/2009 | Kuehn et al. |
| 7,582,051 B2 | 9/2009 | Khairkhahan et al. |
| 7,674,222 B2 | 3/2010 | Nikolic et al. |
| 7,758,491 B2 | 7/2010 | Buckner et al. |
| 7,762,943 B2 | 7/2010 | Khairkhahan |
| 7,824,325 B2 | 11/2010 | Dubi |
| 7,862,500 B2 | 1/2011 | Sharkey et al. |
| 7,887,477 B2 | 2/2011 | Sharkey et al. |
| 7,897,086 B2 | 3/2011 | Khairkhahan et al. |
| 7,938,767 B2 | 5/2011 | Evans et al. |
| 7,976,455 B2 | 7/2011 | Khairkhahan |
| 7,993,258 B2 | 8/2011 | Feld et al. |
| 8,192,478 B2 | 6/2012 | Khairkhahan et al. |
| 8,246,671 B2 | 8/2012 | Khairkhahan et al. |
| 8,257,428 B2 | 9/2012 | Khairkhahan et al. |
| 8,377,114 B2 | 2/2013 | Khairkhahan et al. |
| 8,382,653 B2 | 2/2013 | Dubi et al. |
| 8,388,672 B2 | 3/2013 | Khairkhahan et al. |
| 8,398,537 B2 | 3/2013 | Khairkhahan et al. |
| 8,500,622 B2 | 8/2013 | Lipperman et al. |
| 8,500,790 B2 | 8/2013 | Khairkhahan |
| 8,500,795 B2 | 8/2013 | Khairkhahan et al. |
| 8,529,430 B2 | 9/2013 | Nikolic et al. |
| 8,657,873 B2 | 2/2014 | Khairkhahan et al. |
| 8,672,827 B2 | 3/2014 | Nikolic et al. |
| 2001/0014800 A1 | 8/2001 | Frazier et al. |
| 2002/0019580 A1 | 2/2002 | Lau et al. |
| 2002/0026092 A1 | 2/2002 | Buckberg et al. |
| 2002/0028981 A1 | 3/2002 | Lau et al. |
| 2002/0032481 A1 | 3/2002 | Gabbay |
| 2002/0055767 A1 | 5/2002 | Forde et al. |
| 2002/0055775 A1 | 5/2002 | Carpentier et al. |
| 2002/0111647 A1 | 8/2002 | Khairkhahan et al. |
| 2002/0133227 A1 | 9/2002 | Murphy et al. |
| 2002/0161392 A1 | 10/2002 | Dubrul |
| 2002/0161394 A1 | 10/2002 | Macoviak et al. |
| 2002/0169359 A1 | 11/2002 | McCarthy et al. |
| 2002/0169360 A1 | 11/2002 | Taylor et al. |
| 2002/0183604 A1 | 12/2002 | Gowda et al. |
| 2002/0188170 A1 | 12/2002 | Santamore et al. |
| 2003/0045896 A1 | 3/2003 | Murphy et al. |
| 2003/0078671 A1 | 4/2003 | Lesniak et al. |
| 2003/0109770 A1 | 6/2003 | Sharkey et al. |
| 2003/0120337 A1 | 6/2003 | Van Tassel et al. |
| 2003/0135230 A1 | 7/2003 | Massey et al. |
| 2003/0149333 A1 | 8/2003 | Alferness |
| 2003/0149422 A1 | 8/2003 | Muller |
| 2003/0181942 A1 | 9/2003 | Sutton et al. |
| 2003/0220667 A1 | 11/2003 | van der Burg et al. |
| 2004/0002626 A1 | 1/2004 | Feld et al. |
| 2004/0034366 A1 | 2/2004 | van der Burg et al. |
| 2004/0044361 A1 | 3/2004 | Frazier et al. |
| 2004/0054394 A1 | 3/2004 | Lee |
| 2004/0064014 A1 | 4/2004 | Melvin et al. |
| 2004/0122090 A1 | 6/2004 | Lipton |
| 2004/0127935 A1 | 7/2004 | Van Tassel et al. |
| 2004/0133062 A1 | 7/2004 | Pai et al. |
| 2004/0136992 A1 | 7/2004 | Burton et al. |
| 2004/0172042 A1 | 9/2004 | Suon et al. |
| 2004/0186511 A1 | 9/2004 | Stephens et al. |
| 2004/0215230 A1 | 10/2004 | Frazier et al. |
| 2004/0220610 A1 | 11/2004 | Kreidler et al. |
| 2004/0243170 A1 | 12/2004 | Suresh et al. |
| 2004/0260331 A1 | 12/2004 | D'Aquanni et al. |
| 2004/0260346 A1 | 12/2004 | Overall et al. |
| 2004/0267086 A1 | 12/2004 | Anstadt et al. |
| 2004/0267378 A1 | 12/2004 | Gazi et al. |
| 2005/0007031 A1 | 1/2005 | Hyder |
| 2005/0015109 A1 | 1/2005 | Lichtenstein |
| 2005/0038470 A1 | 2/2005 | van der Burg et al. |
| 2005/0043708 A1 | 2/2005 | Gleeson et al. |
| 2005/0065548 A1 | 3/2005 | Marino et al. |
| 2005/0085826 A1 | 4/2005 | Nair et al. |
| 2005/0096498 A1 | 5/2005 | Houser et al. |
| 2005/0113811 A1 | 5/2005 | Houser et al. |
| 2005/0113861 A1 | 5/2005 | Corcoran et al. |
| 2005/0124849 A1 | 6/2005 | Barbut et al. |
| 2005/0137690 A1 | 6/2005 | Salahieh et al. |
| 2005/0142180 A1 | 6/2005 | Bisgaier et al. |
| 2005/0177180 A1 | 8/2005 | Kaganov et al. |
| 2005/0187620 A1 | 8/2005 | Pai et al. |
| 2005/0216052 A1 | 9/2005 | Mazzocchi et al. |
| 2005/0228434 A1 | 10/2005 | Amplatz et al. |
| 2005/0277981 A1 | 12/2005 | Maahs et al. |
| 2005/0277983 A1 | 12/2005 | Saadat et al. |
| 2005/0283218 A1 | 12/2005 | Williams |
| 2006/0019888 A1 | 1/2006 | Zhou |
| 2006/0025800 A1 | 2/2006 | Suresh |
| 2006/0030881 A1 | 2/2006 | Sharkey et al. |
| 2006/0063970 A1 | 3/2006 | Raman et al. |
| 2006/0069430 A9 | 3/2006 | Rahdert et al. |
| 2006/0079736 A1 | 4/2006 | Chin et al. |
| 2006/0116692 A1 | 6/2006 | Ward |
| 2006/0136043 A1 | 6/2006 | Cully et al. |
| 2006/0199995 A1 | 9/2006 | Vijay |
| 2006/0229491 A1 | 10/2006 | Sharkey et al. |
| 2006/0259124 A1 | 11/2006 | Matsuoka et al. |
| 2006/0276684 A1 | 12/2006 | Speziali |
| 2007/0129753 A1 | 6/2007 | Quinn et al. |
| 2007/0135889 A1 | 6/2007 | Moore et al. |
| 2007/0162048 A1 | 7/2007 | Quinn et al. |
| 2007/0213578 A1 | 9/2007 | Khairkhahan et al. |
| 2008/0015717 A1 | 1/2008 | Griffin et al. |
| 2008/0045778 A1 | 2/2008 | Lichtenstein et al. |
| 2008/0228205 A1 | 9/2008 | Khairkhahan et al. |
| 2009/0112050 A1 | 4/2009 | Farnan et al. |
| 2010/0030256 A1 | 2/2010 | Dubrul et al. |
| 2010/0057185 A1 | 3/2010 | Melsheimer et al. |
| 2010/0274227 A1 | 10/2010 | Khairkhahan et al. |
| 2011/0087066 A1 | 4/2011 | Boutillette et al. |
| 2011/0092761 A1 | 4/2011 | Almog et al. |
| 2011/0098525 A1 | 4/2011 | Kermode et al. |
| 2011/0178362 A1 | 7/2011 | Evans et al. |
| 2011/0264204 A1 | 10/2011 | Khairkhahan |
| 2012/0041257 A1 | 2/2012 | Stankus et al. |
| 2012/0245604 A1 | 9/2012 | Tegzes |
| 2013/0090677 A1 | 4/2013 | Evans et al. |
| 2013/0165735 A1 | 6/2013 | Khairkhahan et al. |
| 2013/0270735 A1 | 10/2013 | Alexander |
| 2013/0274595 A1 | 10/2013 | Kermode et al. |
| 2013/0317537 A1 | 11/2013 | Khairkhahan |
| 2013/0338695 A1 | 12/2013 | Nikolic et al. |
| 2014/0296624 A1 | 10/2014 | Kermode et al. |
| 2014/0343356 A1 | 11/2014 | Nikolic et al. |
| 2015/0182338 A1 | 7/2015 | Kermode et al. |
| 2015/0209144 A1 | 7/2015 | Khairkhahan |

(56) References Cited

U.S. PATENT DOCUMENTS

| | | | |
|---|---|---|---|
| 2015/0265405 A1 | 9/2015 | Boutillette et al. | |
| 2016/0262892 A1 | 9/2016 | Kermode et al. | |

FOREIGN PATENT DOCUMENTS

| | | |
|---|---|---|
| EP | 2344070 A | 7/2011 |
| EP | 2244661 B1 | 3/2012 |
| EP | 2082690 B1 | 6/2012 |
| JP | H08257031 A | 10/1996 |
| JP | 2001520910 A | 11/2001 |
| JP | 2003512128 A | 4/2003 |
| JP | 2003512129 A | 4/2003 |
| JP | 2005324019 | 11/2005 |
| JP | 2008514291 A | 5/2008 |
| KR | 10-1070811 B1 | 10/2011 |
| WO | WO 96/37859 A1 | 11/1996 |
| WO | WO 98/03213 A1 | 1/1998 |
| WO | WO 00/27292 A1 | 5/2000 |
| WO | WO 00/42919 A1 | 7/2000 |
| WO | WO 00/50639 A2 | 8/2000 |
| WO | WO 01/30266 A1 | 5/2001 |
| WO | WO 01/78625 A1 | 10/2001 |
| WO | WO 02/30335 A2 | 4/2002 |
| WO | WO 02/45710 A1 | 6/2002 |
| WO | WO 02/071977 A2 | 9/2002 |
| WO | WO 02/087481 A1 | 11/2002 |
| WO | WO 03/007778 A2 | 1/2003 |
| WO | WO 03/043507 A2 | 5/2003 |
| WO | WO 03/073961 A1 | 9/2003 |
| WO | WO 03/090716 A1 | 11/2003 |
| WO | WO 03/099300 A1 | 12/2003 |
| WO | WO 03/099320 A1 | 12/2003 |
| WO | WO 03/103538 A1 | 12/2003 |
| WO | WO 03/103743 A2 | 12/2003 |
| WO | WO 2004/012629 A1 | 2/2004 |
| WO | WO 2004/019866 A2 | 3/2004 |
| WO | WO 2004/066805 A2 | 8/2004 |
| WO | WO 2004/100803 A1 | 11/2004 |
| WO | WO 2005/007031 A2 | 1/2005 |
| WO | WO 2005/007873 A2 | 1/2005 |
| WO | WO 2005/041745 A2 | 5/2005 |
| WO | WO 2005/091860 A2 | 10/2005 |
| WO | WO 2005/102181 A1 | 11/2005 |
| WO | WO 2006/033107 A2 | 3/2006 |
| WO | WO 2006/055683 A2 | 5/2006 |
| WO | WO 2007/016349 A2 | 2/2007 |
| WO | WO 2007/092354 A2 | 8/2007 |
| WO | WO 2007/143560 A2 | 12/2007 |
| WO | WO 2008/010792 A1 | 1/2008 |
| WO | WO 2011/011641 A2 | 1/2011 |
| WO | WO2012/099418 A2 | 7/2012 |
| WO | WO2013065036 A2 | 5/2013 |
| WO | WO 2013/128461 A1 | 9/2013 |

OTHER PUBLICATIONS

AGA Medical Corporation. www.amplatzer.com/products. "The Muscular VSD Occluder" and "The Septal Occluder" device description. Accessed Apr. 3, 2002.

Anand et al.; Isolated myocyte contractile function is normal in postinfarct remodeled rat heart with systolic dysfunction; Circulation ; 96(11); pp. 3974-3984; Dec. 1997.

Artrip et al.; Left ventricular volume reduction surgery for heart failure: A physiologic perspective; J Thorac Cardiovasc Surg; vol. 122; No. 4; pp. 775-782; Oct. 2001.

Boersma et al.; Early thrombolytic treatment in acute myocardial infarction: reappraisal of the golden hour; Lancet: vol. 348(9030); pp. 771-775; Sep. 21, 1996.

Bozdag-Turan et al.; Left ventricular partitioning device in a patient with chronic heart failure: Short-term clinical follow-up; Int J Cardiol; 163(1); pp. e1-e3; (Epub) Jul. 2012.

Dang et al.; Akinetic myocardial infarcts must contain contracting myocytes: finite-element model study; Am J Physiol Heart Circ Physiol ; 288; pp. H1844-H1850; Apr. 2005.

Dang et al.; Effect of ventricular size and patch stiffness in surgical anterior ventricular restoration: a finite element model study; Ann Thorac Surg; 79; pp. 185-193; Jan. 2005.

Di Mattia, et al. Surgical treatment of left ventricular post-infarction aneurysm with endoventriculoplasty: late clinical and functioal results. European Journal of Cardio-thoracic Surgery. 15(4):413-418; Apr. 1999.

Dor, et al. Ventricular remodeling in coronary artery disease. Current Opinion in Cardiology. 12(6):533-537; Nov. 1997.

Dor, V. The treatment of refractory ischemic ventricular tachycardia by endoventricular patch plasty reconstruction of the left ventricle. Seminars in Thoracic and Cardiovascular Surgery. 9(2): 146-155; Apr. 1997.

Dor. Surgery for left ventricular aneurysm. Current Opinion in Cardiology. vol. 5; No. 6; pp. 773-780; Dec. 1990.

Gore Medical. www.goremedical.com. "Helex Septal Occluder" product description. Accessed Apr. 3, 2002.

Grossman et al.; Wall stress and patterns of hypertrophy in the human left ventricle; J Clin Invest; 56; pp. 56-64; Jul. 1975.

Guccione et al.; Finite element stress analysis of left ventricular mechanics in the beating dog heart; J Biomech; 28; pp. 1167-1177; Oct. 1995.

Guccione et al.; Mechanics of active contraction in cardiac muscle: Part II—Cylindrical models of the systolic left ventricle; J Biomech Eng; 115; pp. 82-90; Feb. 1993.

Gutberlet et al.; Myocardial viability assessment in patients with highly impaired left ventricular function: comparison of delayed enhancement, dobutamine stress MRI, end-diastolic wall thickness, and TI201-SPECT with functional recovery after revascularization; Eur Radiol; 15; pp. 872-880; May 2005.

Huisman et al.; Measurement of left ventricular wall stress; Cardiovascular Research; 14; pp. 142-153; Mar. 1980.

Jackson et al.; Extension of borderzone myocardium in postinfarction dilated cardiomyopathy; J Am Coll Cardiol; 40(6); 1160-7; and discussion; pp. 1168-1171; Sep. 2002.

James et al.; Blood Volume and Brain Natriuretic Peptide in Congestive Heart Failure: A Pilot Study; American Heart Journal; vol. 150; issue 5, pp. 984.e1-984.e6 (abstract); Dec. 6, 2005.

Januzzi, James L.; Natriuretic peptide testing: A window into the diagnosis and prognosis of heart failure; Cleveland Clinic Journal of Medicine; vol. 73; No. 2; pp. 149-152 and 155-157; Feb. 2006.

Jones et al.; Coronary Bypass Surgery with or without Surgical Ventricular Reconstruction; N Engl J Med; 360; pp. 1705-1717; Apr. 2009.

Katsumata, et al. An objective appraisal of partial left ventriculectomy for heart failure. Journal of Congestive Heart Failure and Circulator Support. 1(2): 97-106; (year of pub. sufficiently earlier than effective US filing date and any foreign priority date) 1999.

Kawata, et al. Systolic and Diastolic Function after Patch Reconstruction of Left Ventricular Aneurysms. Ann. Thorac. Surg. 5(2)9:403-407; Feb. 1995.

Lee et al.; A novel method for quantifying in-vivo regional left ventricular myocardial contractility in the border zone of a myocardial infarction (author manuscript, 11 pgs.); J Biomech Eng; 133; 094506; Sep. 2011.

Mazzaferri et al.; Percutaneous left ventricular partitioning in patients with chronic heart failure and a prior anterior myocardial infarction: Results of the Percutaneous Ventricular Restoration in Chronic Heart Failure Patients Trial; Am Heart J; 163; pp. 812-820; May 2012.

Nikolic et al.; Percutaneous implantation of an intraventricular device for the treatment of heart failure: experimental results and proof of concept; J Card Fail; 15(9); pp. 790-797; Nov. 2009.

Priola et al.; Functional characteristics of the left ventricular inflow and outflow tracts; Circ Res; 17; pp. 123-129; Aug. 1965.

Sagic et al.; Percutaneous implantation of the left ventricular partitioning device for chronic heart failure: a pilot study with 1-year follow-up. Eur J Heart Fail; 12; pp. 600-606; Apr. 2010.

(56) References Cited

OTHER PUBLICATIONS

Sharkey et al.; Left ventricular apex occluder. Description of a a ventricular partitioning device; EuroInterv.; 2(1); pp. 125-127; May 2006.
Sun et al.; A computationally efficient formal optimization of regional myocardial contractility in a sheep with left ventricular aneurysm (author manuscript, 21 pgs.); J Biomech Eng; 131; 111001; Nov. 2009.
U.S. Food & Drug Administration; AneuRx Stent Graft System—Instructions for use; (pre-market approval); Sep. 29, 1999; downloaded Apr. 25, 2013 (http://www.accessdata.fda.gov/cdrh_docs/pdf/P990020c.pdf).
Walker et al; Magnetic resonance imaging-based finite element stress analysis after linear repair of left ventricular aneurysm (author manuscript, 17 pgs.); J Thorac Cardiovasc Surg; 135; pp. 1094-1102 e1-2; May 2008.
Walker et al; MRI-based finite-element analysis of left ventricular aneurysm; Am J Physiol Heart Circ Physiol; 289; pp. H692-H700; Aug. 2005.
Walmsley; Anatomy of left ventricular outflow tract; British Heart Journal; 41; pp. 263-267; Mar. 1979.
Wenk et al.; First evidence of depressed contractility in the border zone of a human myocardial infarction; Ann Thorac Surg; 93; pp. 1188-1193; Apr. 2012.
Wenk et al.; Regional left ventricular myocardial contractility and stress in a finite element model of posterobasal myocardial infarction (author manuscript, pgs.); J Biomech Eng; 133(4); 044501; Apr. 2011.
Boutillette et al.; U.S. Appl. No. 15/133,080 entitled "Devices and methods for delivering an endocardial device," filed Apr. 19, 2016.

\* cited by examiner

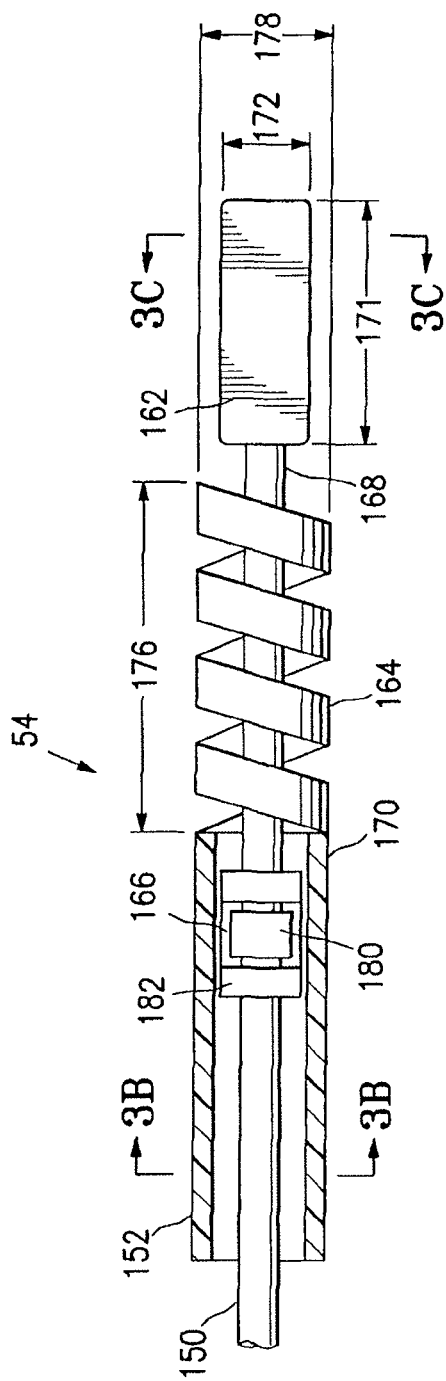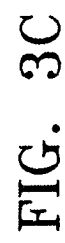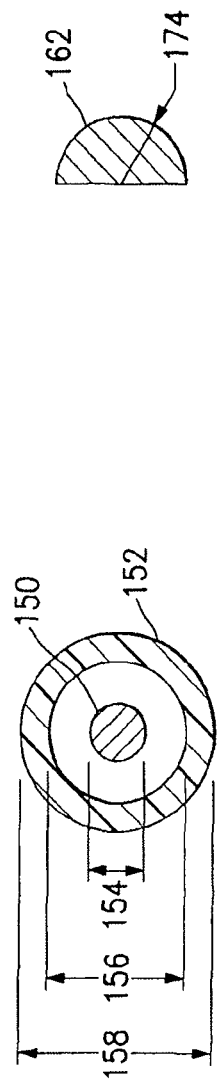
FIG. 3A
FIG. 3C
FIG. 3B

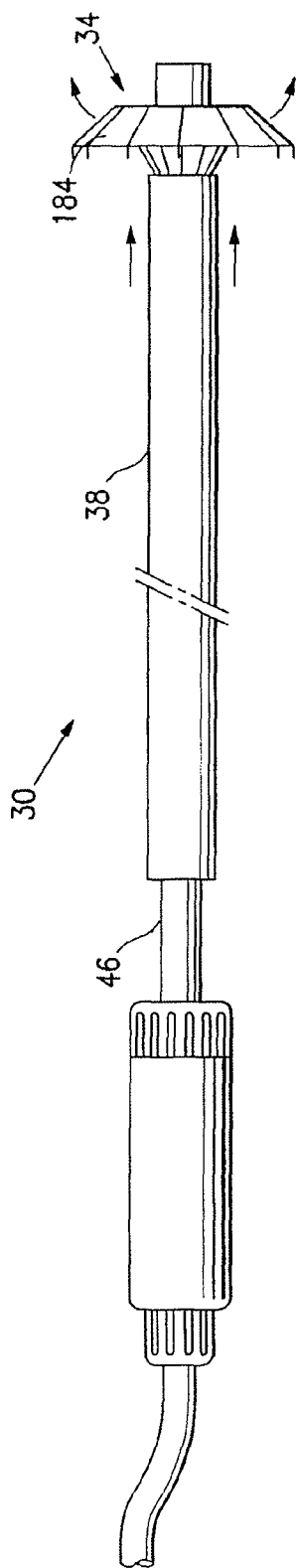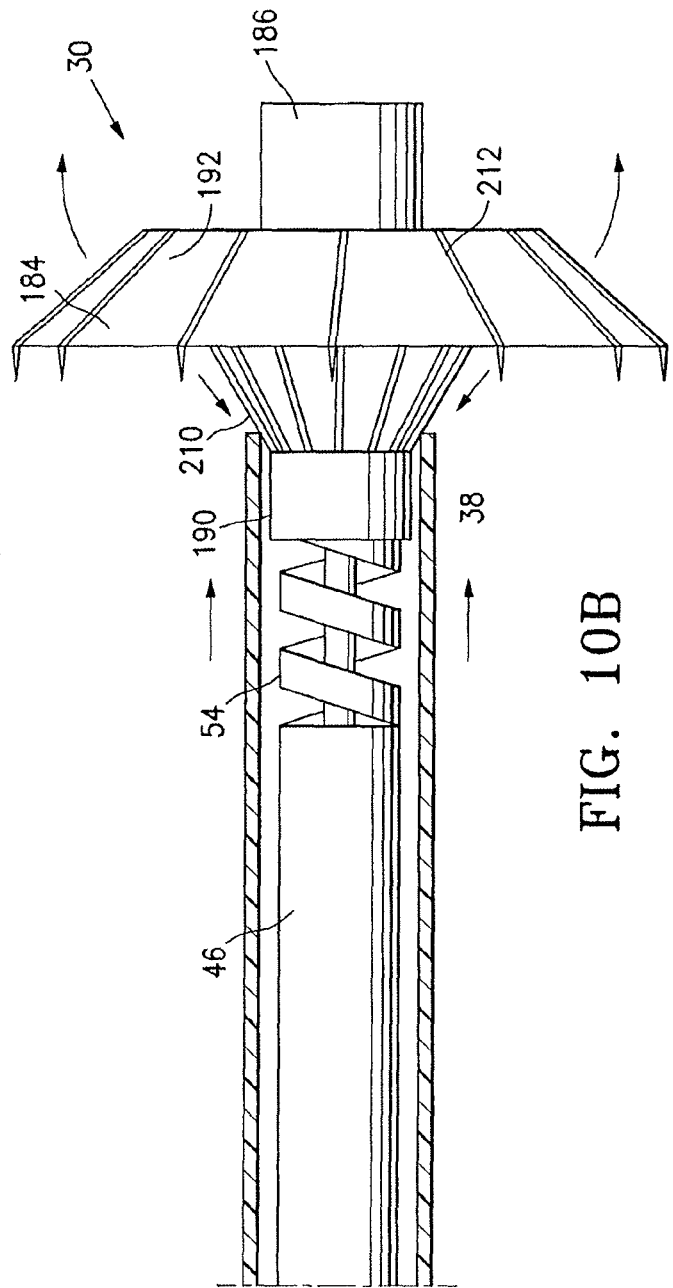
FIG. 10A
FIG. 10B

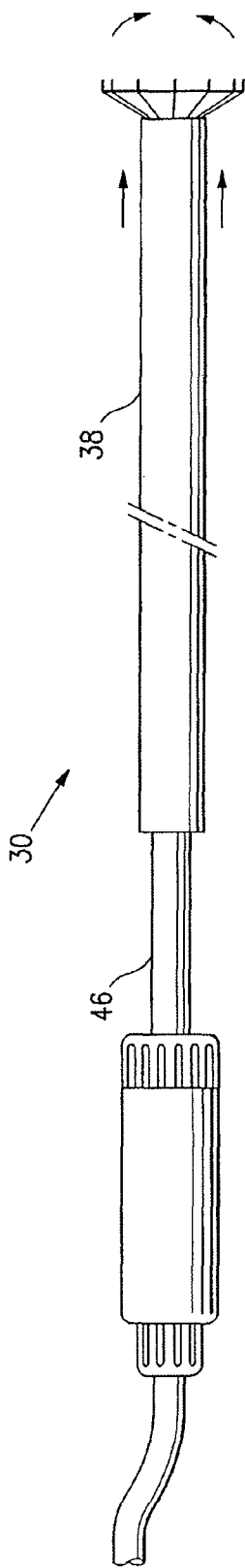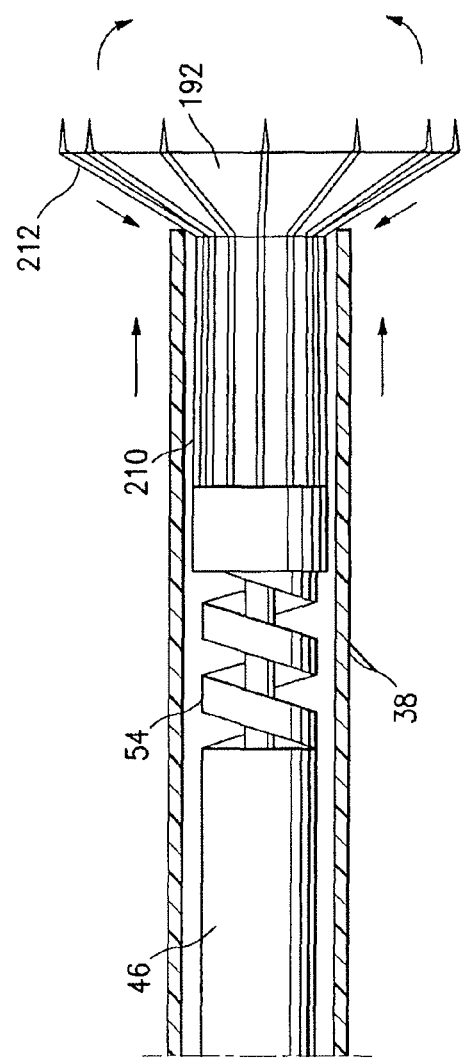
FIG. 11A
FIG. 11B

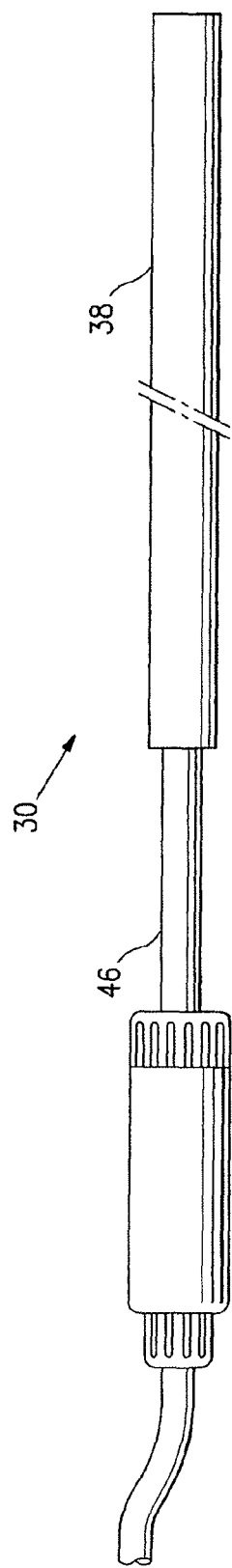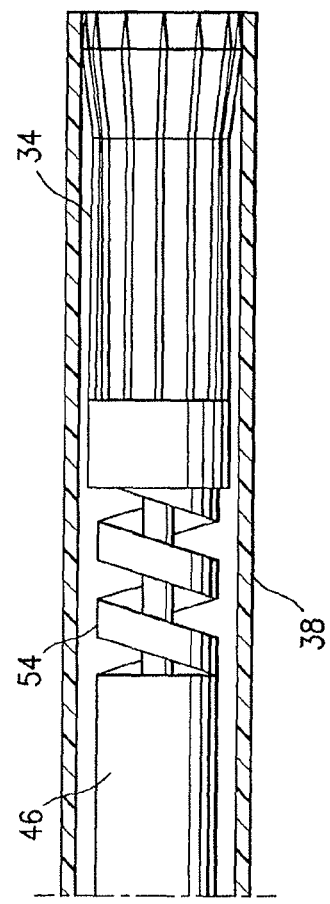
FIG. 12A
FIG. 12B

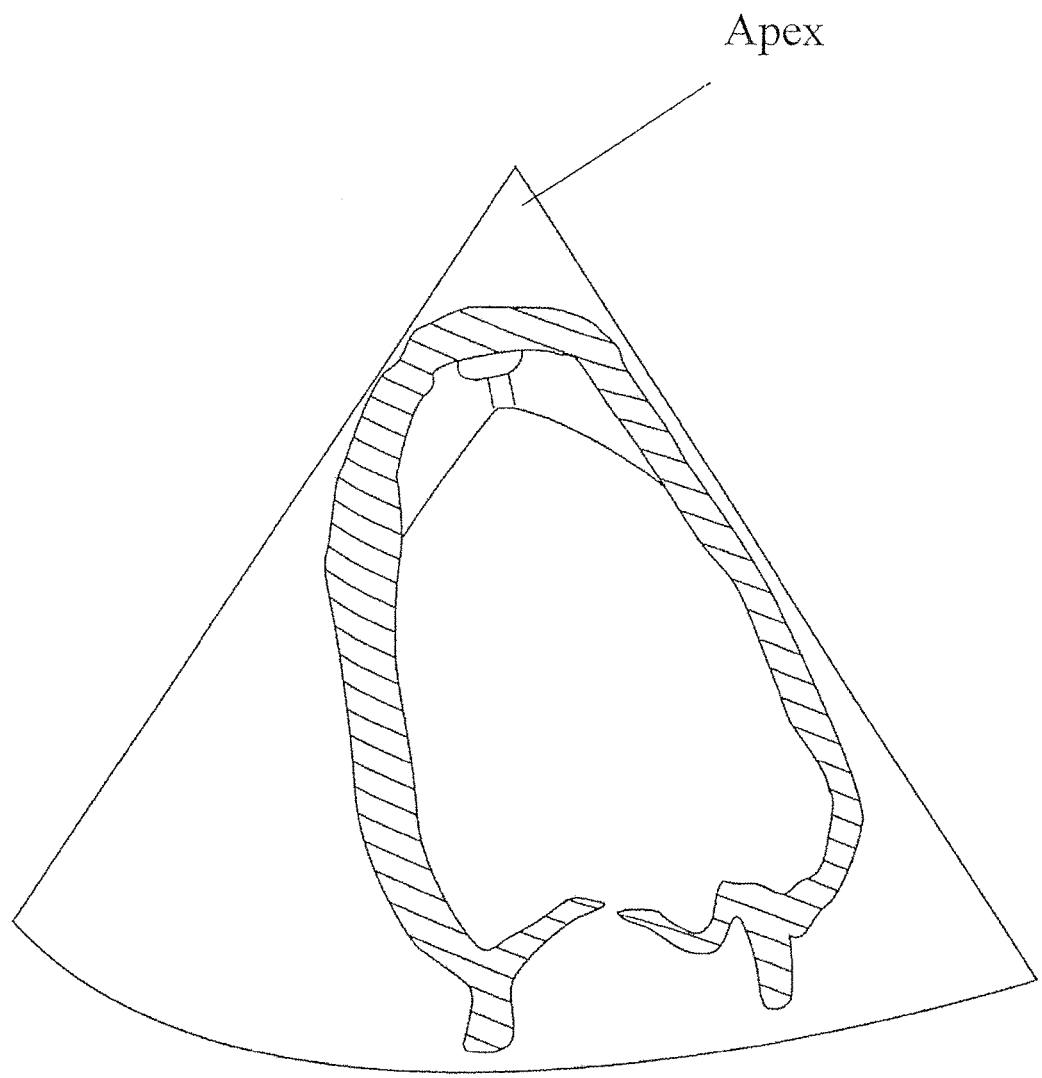
FIG. 38A  Echocardiogram View of Implant at End Diastole

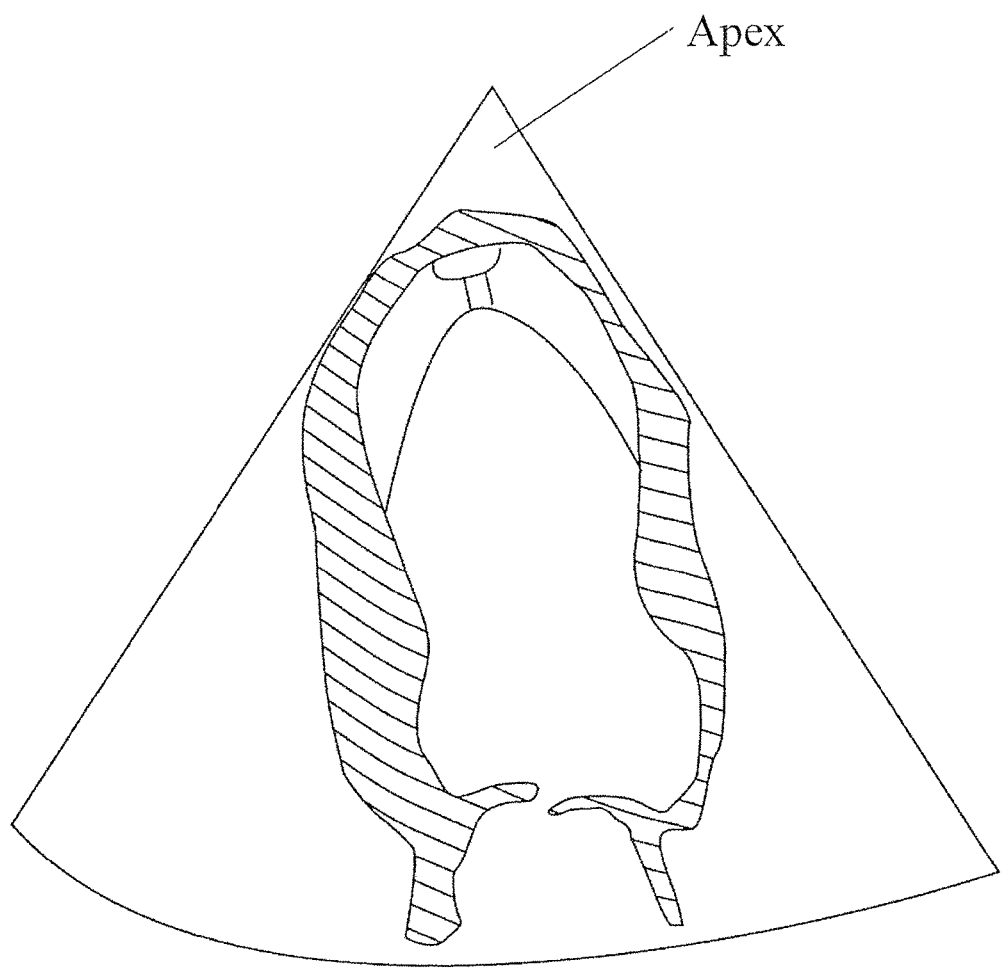
FIG. 38B  Echocardiogram View of Implant at End Systole

SYSTEMS AND METHODS FOR IMPROVING CARDIAC FUNCTION

CROSS REFERENCE TO RELATED APPLICATIONS

This application claims benefit of U.S. Provisional Patent Application Ser. No. 61/816,628, titled "SYSTEMS AND METHODS FOR IMPROVING CARDIAC FUNCTION," and filed on Apr. 26, 2013. This application is also a continuation-in-part of U.S. patent application Ser. No. 11/801,075, titled "SYSTEM FOR IMPROVING CARDIAC FUNCTION," filed May 7, 2007, now U.S. Pat. No. 8,657,873, which is a continuation of U.S. patent application Ser. No. 10/436,959, titled "SYSTEM FOR IMPROVING CARDIAC FUNCTION," filed on May 12, 2003, now U.S. Pat. No. 8,257,428, which is a continuation-in-part of U.S. patent application Ser. No. 09/635,511, titled "DEVICE AND METHOD FOR TREATMENT OF HOLLOW ORGANS," filed on Aug. 9, 2000, now abandoned, which claims benefit of U.S. Provisional Patent Application Ser. No. 60/147,894, titled "EXPANDABLE, IMPLANTABLE DEVICE AND METHOD," and filed on Aug. 9, 1999. This application is also a continuation-in-part of U.S. patent application Ser. No. 12/691,587, titled "CARDIAC DEVICE AND METHODS OF USE THEREOF," filed Jan. 21, 2010, now U.S. Patent Application Publication No. 2010-0121132-A1, which is a continuation of U.S. patent application Ser. No. 11/640,469, titled "CARDIAC DEVICE AND METHODS OF USE THEREOF," filed Dec. 14, 2006, now U.S. Pat. No. 7,674,222, which is a continuation-in-part application of U.S. patent application Ser. No. 10/212,033, titled "DEVICE FOR IMPROVING CARDIAC FUNCTION," filed Aug. 1, 2002, now U.S. Pat. No. 7,303,526, which is a continuation-in-part of prior U.S. patent application Ser. No. 09/635,511, titled "DEVICE AND METHOD FOR TREATMENT OF HOLLOW ORGANS," filed on Aug. 9, 2000, now abandoned, which claims benefit of U.S. Provisional Patent Application No. 60/147,894, titled "EXPANDABLE, IMPLANTABLE DEVICE AND METHOD," and filed on Aug. 9, 1999; each of which is herein incorporated by reference in its entirety.

STATEMENT AS TO FEDERALLY SPONSORED RESEARCH

This invention was made with Government support under Grant No. R01-HL-084431 and Grant No. R01-HL-077921 awarded by the National Institutes of Health. The Government has certain rights in the invention.

INCORPORATION BY REFERENCE

All publications and patent applications mentioned in this specification are herein incorporated by reference to the same extent as if each individual publication or patent application was specifically and individually indicated to be incorporated by reference.

FIELD

Embodiments of this invention relate to methods, devices and systems for improving cardiac function.

BACKGROUND

Heart failure (HF) is one of the most common causes of in-hospital mortality for patients with cardiac diseases. Heart failure is typified by the inability of the heart to pump enough blood to meet the body's metabolic requirements for oxygen and nutrients leading to discrepancies between myocardial oxygen supply and demand. Congestive heart failure annually leads to millions of hospital visits internationally. Congestive heart failure is the description given to a myriad of symptoms that can be the result of the heart's inability to meet the body's demand for blood flow. In certain pathological conditions, the ventricles of the heart become ineffective in pumping the blood, causing a back-up of pressure in the vascular system behind the ventricle.

The reduced effectiveness of the heart is usually due an enlargement of the heart. A myocardial ischemia may, for example, cause a portion of a myocardium of the heart to lose its ability to contract. Prolonged ischaemia can lead to infarction of a portion of the myocardium (heart muscle) wherein the heart muscle dies and becomes scar tissue. Once this tissue dies it no longer functions as a muscle and cannot contribute to the pumping action of the heart. When the heart tissue is no longer pumping effectively, that portion of the myocardium is said to be hypokinetic, meaning that it is less contractile than the uncompromised myocardial tissue. As this situation worsens, the local area of compromised myocardium may in fact bulge out as the heart contracts, further decreasing the heart's ability to move blood forward. When local wall motion moves in this way, it is said to be dyskinetic, or akinetic. The dyskinetic portion of the myocardium may stretch and eventually form an aneurysmic bulge. Certain diseases may cause a global dilated myopathy, i.e., a general enlargement of the heart when this situation continues for an extended period of time.

As the heart begins to fail, distilling pressures increase, which stretches the ventricular chamber prior to contraction and greatly increases the pressure in the heart. In response, the heart tissue reforms to accommodate the chronically increased filling pressures, further increasing the work that the now comprised myocardium must perform.

This vicious cycle of cardiac failure results in the symptoms of congestive heart failure, such as shortness of breath on exertion, edema in the periphery, nocturnal dypsnia (a characteristic shortness of breath that occurs at night after going to bed), waking, and fatigue, to name a few. The enlargements increase stress on the myocardium. The stress increase requires a larger amount of oxygen supply, which can result in exhaustion of the myocardium leading to reduced cardiac output of the heart.

The left ventricle's inability to generate sufficient cardiac output, i.e. HF, is commonly associated with left ventricular systolic (emptying of left ventricular chamber) dysfunction, but its symptoms may also arise as a result of diastolic (filling of left ventricular chamber) dysfunction (with or without the presence of systolic dysfunction). The term "diastolic dysfunction" refers to changes in ventricular diastolic properties that have an adverse effect on ventricular diastolic pressures and ventricular filling.

An integral part of normal diastolic filling is the contribution of the left ventricular (LV) elastic recoil forces to the LV filling. Elastic recoil forces are generated within healthy myocardium during systolic shortening. The magnitudes of elastic recoil forces are inversely proportional to the volume of the LV, i.e., they increase as the LV volume decreases. Their contribution is important in early diastole because they allow rapid and enhanced early filling by assisting the expansion of the left ventricle.

In a case of ventricular enlargement and/or the decrease of myocardial function due to hypertrophy the left ventricular elastic recoil forces may be diminished or nonexistent, therefore ceasing to assist early ventricular filling and leading to an increase of the ventricular filling pressure.

Intervention to alleviate the resultant symptoms of the physical changes described above may offer great benefit to patients with heart disease. Administration of vasodilators, diuretics, sodium channel blockers, and inotropic agents have been used to reduce the number of acute events and slow the advance of disease, but cannot reverse the physical changes to the heart. Surgical intervention can reduce the volume of the ventricle such that cardiac function is improved but carries high risk for the patient. Other less invasive modes of intervention offer improved function while reducing risk for the patient during and after the procedure.

Additional background may be described in each of the following publications, each of which is incorporated by reference:

1. Anand I S, D Liu, S S Chugh, A J Prahash, S Gupta, R John, F Popescu and Y Chandrashekhar (1997) Isolated myocyte contractile function is normal in postinfarct remodeled rat heart with systolic dysfunction. Circulation 96:3974-84
2. Bozdag-Turan I, B Bermaoui, R G Turan, L Paranskaya, D A G, S Kische, K Hauenstein, C A Nienaber and H Ince (2012) Left ventricular partitioning device in a patient with chronic heart failure: Short-term clinical follow-up. Int J Cardiol 163:e1-e3.
3. Dang A B, J M Guccione, J M Mishell, P Zhang, A W Wallace, R C Gorman, J H Gorman, 3rd and M B Ratcliffe (2005) Akinetic myocardial infarcts must contain contracting myocytes: finite-element model study. Am J Physiol Heart Circ Physiol 288:H1844-50
4. Dang A B, J M Guccione, P Zhang, A W Wallace, R C Gorman, J H Gorman, 3rd and M B Ratcliffe (2005) Effect of ventricular size and patch stiffness in surgical anterior ventricular restoration: a finite element model study. Ann Thorac Surg 79:185-93
5. Grossman W, D Jones and L P McLaurin (1975) Wall stress and patterns of hypertrophy in the human left ventricle. J Clin Invest 56:56-64
6. Guccione J M, L K Waldman and A D McCulloch (1993) Mechanics of active contraction in cardiac muscle: Part II—Cylindrical models of the systolic left ventricle. J Biomech Eng 115:82-90
7. Guccione J M, K D Costa and A D McCulloch (1995) Finite element stress analysis of left ventricular mechanics in the beating dog heart. J Biomech 28:1167-77
8. Gutberlet M, M Frohlich, S Mehl, H Amthauer, H Hausmann, R Meyer, H Siniawski, J Ruf, M Plotkin, T Denecke, B Schnackenburg, R Hetzer and R Felix (2005) Myocardial viability assessment in patients with highly impaired left ventricular function: comparison of delayed enhancement, dobutamine stress MRI, end-diastolic wall thickness, and Tl201-SPECT with functional recovery after revascularization. Eur Radiol 15:872-80
9. Huisman R M, G Elzinga, N Westerhof and P Sipkema (1980) Measurement of left ventricular wall stress. Cardiovascular Research 14:142-53
10. Jackson B M, J H Gorman, S L Moainie, T S Guy, N Narula, J Narula, M G John-Sutton, L H Edmunds, Jr. and R C Gorman (2002) Extension of borderzone myocardium in postinfarction dilated cardiomyopathy. J Am Coll Cardiol 40:1160-7; discussion 1168-71
11. Jones R H, E J Velazquez, R E Michler, G Sopko, J K Oh, C M O'Connor, J A Hill, L Menicanti, Z Sadowski, P Desvigne-Nickens, J-L Rouleau, K L Lee and the STICH Hypothesis 2 Investigators (2009) Coronary Bypass Surgery with or without Surgical Ventricular Reconstruction. N Engl J Med 360:1705-17
12. Lee L C, J F Wenk, D Klepach, Z Zhang, D Saloner, A W Wallace, L Ge, M B Ratcliffe and J M Guccione (2011) A novel method for quantifying in-vivo regional left ventricular myocardial contractility in the border zone of a myocardial infarction. J Biomech Eng 133:094506
13. Mazzaferri E L, Jr., S Gradinac, D Sagic, P Otasevic, A K Hasan, T L Goff, H Sievert, N Wunderlich, S D Nikolic and WT Abraham (2012) Percutaneous left ventricular partitioning in patients with chronic heart failure and a prior anterior myocardial infarction: Results of the PercutAneous Ventricular RestorAtion in Chronic Heart failUre PaTiEnts Trial. Am Heart J 163:812-820 e1
14. Nikolic S D, A Khairkhahan, M Ryu, G Champsaur, E Breznock and M Dae (2009) Percutaneous implantation of an intraventricular device for the treatment of heart failure: experimental results and proof of concept. J Card Fail 15:790-7
15. Sagic D, P Otasevic, H Sievert, A Elsasser, V Mitrovic and S Gradinac (2010) Percutaneous implantation of the left ventricular partitioning device for chronic heart failure: a pilot study with 1-year follow-up. Eur J Heart Fail 12:600-6
16. Sun K, N Stander, C S Jhun, Z Zhang, T Suzuki, G Y Wang, M Saeed, A W Wallace, E E Tseng, A J Baker, D Saloner, D R Einstein, M B Ratcliffe and J M Guccione (2009) A computationally efficient formal optimization of regional myocardial contractility in a sheep with left ventricular aneurysm. J Biomech Eng 131:111001
17. Walker J C, M B Ratcliffe, P Zhang, A W Wallace, B Fata, E W Hsu, D Saloner and J M Guccione (2005) MRI-based finite-element analysis of left ventricular aneurysm. Am J Physiol Heart Circ Physiol 289:H692-700
18. Walker J C, M B Ratcliffe, P Zhang, A W Wallace, E W Hsu, D A Saloner and J M Guccione (2008) Magnetic resonance imaging-based finite element stress analysis after linear repair of left ventricular aneurysm. J Thorac Cardiovasc Surg 135:1094-102, 1102 e1-2
19. Wenk J F, K Sun, Z Zhang, M Soleimani, L Ge, D Saloner, A W Wallace, M B Ratcliffe and J M Guccione (2011) Regional left ventricular myocardial contractility and stress in a finite element model of posterobasal myocardial infarction. J Biomech Eng 133:044501
20. Wenk J F, D Klepach, L C Lee, Z Zhang, L Ge, E E Tseng, A Martin, S Kozerke, J H Gorman, 3rd, R C Gorman and J M Guccione (2012) First evidence of depressed contractility in the border zone of a human myocardial infarction. Ann Thorac Surg 93:1188-93

SUMMARY OF THE DISCLOSURE

The present invention relates to methods, devices and systems for improving cardiac function. In some embodiments, a device configured for delivery to a heart of a patient is provided. The device can include a plurality of radially expandable resilient ribs connected at their distal ends to a central hub, and a membrane coupled to said ribs, wherein said ribs are adapted to anchor to a wall of a ventricle of said heart to store energy provided by said ventricle during systole and to provide a force to said wall of said ventricle during diastole, thereby improving diastolic compliance.

In some embodiments, the device is configured for percutaneous delivery to a heart of a patient.

In some embodiments, by improving diastolic compliance, myofiber stress in the ventricle is reduced.

In some embodiments, the device further includes anchor elements on proximal ends of said ribs for anchoring said device to a selected area of said wall of said ventricle.

In some embodiments, the device enhances, improves, or restores a composite material property of a ventricle of the heart.

In some embodiments, the device reduces a filing pressure of the heart.

In some embodiments, a device configured for delivery to a heart of a patient is provided. The device can include a plurality of radially expandable resilient ribs connected at their distal ends to a central hub, and a membrane coupled to said ribs, wherein said ribs are adapted to anchor to a wall of a ventricle of said heart and the membrane is adapted to separate the left ventricle into a main functioning portion and a secondary, essentially non-functioning portion thereby reducing pressure acting on the non-functioning portion.

In some embodiments, the device is configured for percutaneous delivery to a heart of a patient.

In some embodiments, by reducing pressure acting on the non-functioning portion of the ventricle, myofiber stress in the ventricle is reduced.

In some embodiments, the non-functioning portion of the ventricle is an infarcted region of the ventricle.

In some embodiments, a method of treating a patient suffering from a heart condition is provided. The method includes advancing a collapsed device comprising a plurality of radially expandable resilient ribs connected at their distal ends to a central hub, said device further comprising a membrane coupled to said ribs; expanding said ribs in a ventricle of said heart; partitioning said ventricle with said membrane; and securing said device to opposing walls of said ventricle thereby providing elastic support between said opposing ventricular walls, thereby improving diastolic compliance.

In some embodiments, the advancing step further comprises advancing the collapsed device percutaneously.

In some embodiments, by improving diastolic compliance, myofiber stress in the ventricle is reduced.

In some embodiments, the method enhances, improves, or restores a composite material property of a ventricle of the heart.

In some embodiments, the method reduces a filling pressure of the heart.

In some embodiments, the method further includes augmenting movement of said walls of said ventricle during diastole.

In some embodiments, the step of augmenting movement of said walls of said ventricle during diastole comprises harnessing motion of a healthy portion of said ventricle to create motion in an unhealthy portion of said ventricle.

In some embodiments, the method further includes decreasing stress in said walls of said ventricle, thereby limiting remodeling of said heart.

In some embodiments, the method further includes reducing diastolic pressure of said ventricle.

In some embodiments, the method further includes improving a pressure-volume relationship of said ventricle.

In some embodiments, the method further includes supporting a weakened cardiac wall.

In some embodiments, a method of treating a patient suffering from a heart condition is provided. The method includes advancing a collapsed device comprising a plurality of radially expandable resilient ribs connected at their distal ends to a central hub, said device further comprising a membrane coupled to said ribs; expanding said ribs in a ventricle of said heart; partitioning said ventricle with said membrane; and securing said device to opposing walls of said ventricle thereby separating the left ventricle into a main functioning portion and a secondary, essentially non-functioning portion and thereby reducing pressure acting on the non-functioning portion.

In some embodiments, the advancing step further comprises advancing the collapsed device percutaneously.

In some embodiments, by reducing pressure acting on the non-functioning portion of the ventricle, myofiber stress in the ventricle is reduced.

In some embodiments, the non-functioning portion of the ventricle is an infarcted region of the ventricle.

In some embodiments, a device for implantation within a ventricle of the heart is provided. The device can include an expandable frame formed from a plurality of ribs extending from a first end of a central hub and a support component extending from a second end of the central hub; and a membrane secured to the plurality of ribs, the membrane having a peripheral portion configured to form a seal against a ventricle wall and an interior portion configured to be spaced away from the ventricle wall by the support component, wherein the interior portion of the membrane is adapted to provide a trampoline effect wherein a pressure receiving face of the interior portion of the membrane is configured to move in a first direction during systole and a second direction during diastole.

In some embodiments, the first direction is substantially opposite the second direction.

In some embodiments, the tips of the plurality of ribs flare outwardly away from a central axis of the device.

In some embodiments, the membrane forms a trumpet shaped surface.

In some embodiments, a method of treating a patient with a diseased left ventricle is provided. The method can include advancing percutaneously to the left ventricle an implant having an expandable frame formed from a plurality of ribs extending from a first end of a central hub, a support component extending from a second end of the central hub, and a membrane secured to the plurality of ribs; aligning the implant with the left ventricular outflow tract; expanding the implant within the left ventricle; and securing the expanded implant within the left ventricle.

In some embodiments, the method further includes sealing a peripheral portion of the membrane against the left ventricle wall.

In some embodiments, the step of sealing the peripheral portion of the membrane isolates an akinetic region of the heart from a function portion of the ventricle.

In some embodiments, the step of sealing the peripheral portion of the membrane isolates an enlarged region of the heart from a function portion of the ventricle.

In some embodiments, the method further includes abutting the support component against the ventricle wall and spacing an interior portion of the membrane from the ventricle wall.

In some embodiments, the interior portion of the membrane is adapted to provide a trampoline effect wherein a pressure receiving face of the interior portion of the membrane is configured to move in a first direction relative to a wall of the ventricle during systole and to recoil in a second direction during diastole.

In some embodiments, aligning the implant with the left ventricular outflow tract comprises aligning the implant to receive flow of blood exiting the mitral valve and redirecting the flow of blood towards the aortic valve.

In some embodiments, aligning comprises aligning a central axis through the central hub of the implant with the left ventricular outflow tract.

In some embodiments, a method of treating a left ventricle of a patient suffering from a heart condition is provided. The method can include percutaneously advancing to the left ventricle an implant having a frame formed from a plurality of ribs and a membrane secured to the frame; securing the implant within the left ventricle so that the membrane cyclically and resiliently moves relative to a wall of the ventricle during a cardiac cycle so that a gap between the membrane and the wall of the ventricle decreases and increases in a trampoline-like fashion.

In some embodiments, percutaneously advancing comprises collapsing the implant and expanding the implant after advancing into the left ventricle.

In some embodiments, securing further comprising securing an end of each of the plurality of ribs against the ventricle wall.

In some embodiments, securing comprises securing the implant at the apex of the ventricle.

In some embodiments, securing the implant comprises securing the implant so that the membrane and frame moves relative to a wall of the ventricle during a cardiac cycle.

In some embodiments, securing the implant within the left ventricle comprises securing the edge of the implant to the ventricle so that a central portion of the implant is separated from the wall of the ventricle and so that the implant may elastically recoil relative to the wall during a cardiac cycle.

In some embodiments, the method further includes aligning the implant with an axis extending through the aortic valve and along the ventricular outflow tract.

In some embodiments, a method of treating a left ventricle of a patient suffering from a heart condition resulting in a left ventricle having a healthy portion and an unhealthy portion is provided. The method includes percutaneously advancing to the left ventricle an implant having a frame formed from a plurality of ribs and a membrane secured to the frame; anchoring the frame in the healthy portion of the left ventricle; and transmitting motion from the healthy portion of the left ventricle through the plurality of ribs and the membrane to the unhealthy portion of the left ventricle.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 3A is cross-sectional side view of a distal end of the deployment member including a key and a detachment screw;

FIG. 3B is a cross-sectional end view on 3B-3B in FIG. 3A of the deployment member;

FIG. 3C is a cross-sectional end view on 3C-3C in FIG. 3A of the key;

FIG. 10A is a view similar to FIG. 9 with the cardiac device partially retracted into the catheter;

FIG. 10B is a cross-sectional side view of a portion of FIG. 10A;

FIG. 11A is a side view of the system with the cardiac device further retracted;

FIG. 11B is a cross-sectional side view of a portion of FIG. 11A;

FIG. 12A is a side view of the system with the cardiac device fully retracted;

FIG. 12B is a cross-sectional side view of a portion of FIG. 12A;

FIGS. 20E-20I are cross sectional side views of a human heart illustrating installation of the cardiac device of FIG. 20A and FIG. 20B.

FIG. 38A is a drawing of the echocardiograph image of the patient's heart after treatment according to a method of the present invention using a diastolic recoil device at end-diastole, highlighting the effective diameter of the diastolic recoil device in the relaxed state.

FIG. 38B is a drawing of the echocardiograph image of the patient's heart after treatment according to a method of the present invention using a diastolic recoil device at end-systole, highlighting the effective diameter of the diastolic recoil device in the constrained state.

DETAILED DESCRIPTION

Figure 1:
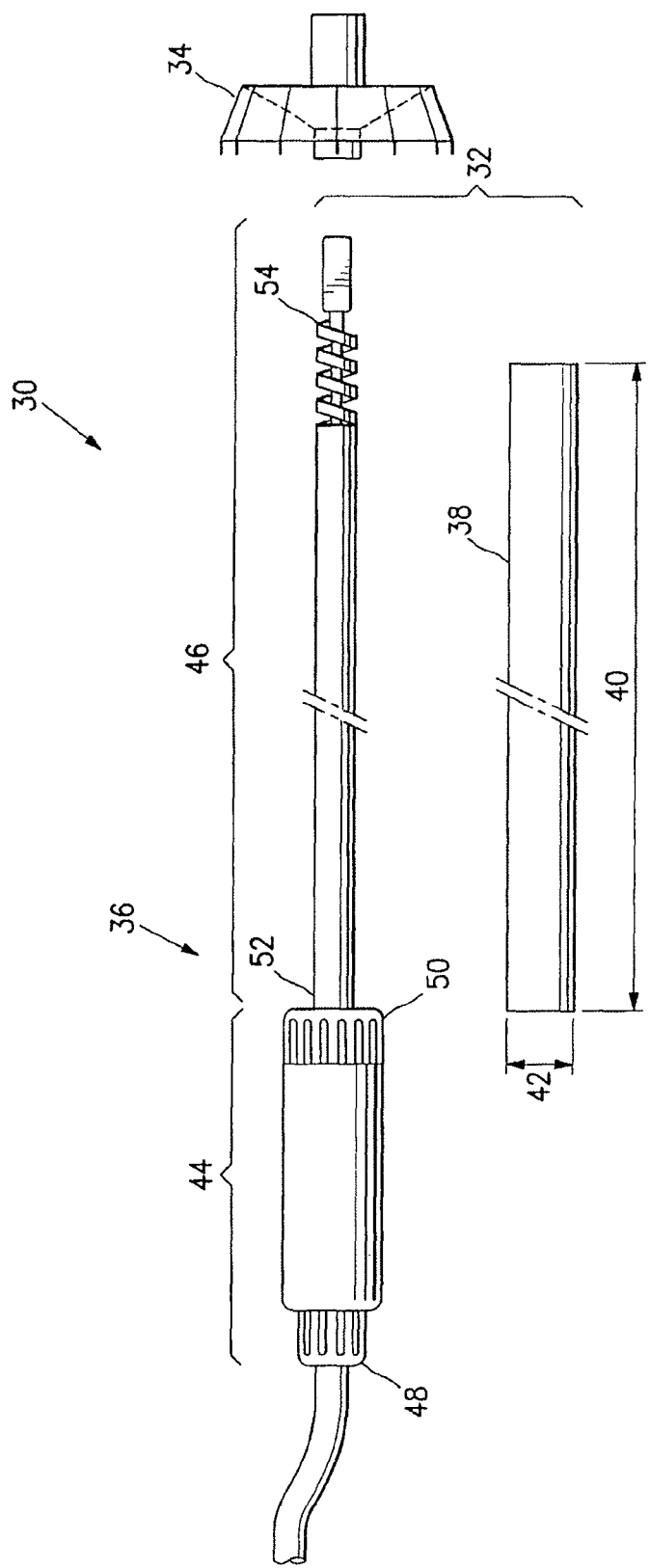
FIG. 1 is an exploded side view of a system for improving cardiac function, according to one embodiment of the invention, including a cardiac device and a deployment system, the deployment system including a deployment mechanism and a catheter tube.

FIG. 1 illustrates a system 30 for improving cardiac function according to one embodiment of the invention. The system 30 includes a deployment system 32 and a cardiac device 34. The deployment system 32 includes a deployment mechanism 36 and a catheter tube 38.

The catheter tube 38 is cylindrical with a length 40 of 110 cm and a diameter 42 of 5 mm. The catheter tube 38 has a circular cross-section and is made of a soft, flexible material.

The deployment mechanism 36 includes a handle 44 and a deployment member 46. The handle 44 has a proximal end 48 and a distal end 50. The deployment member 46 has a proximal end 52 and a distal end 54. The proximal end 52 of the deployment member 46 is secured to the distal end 50 of the handle 44.

Figure 2:
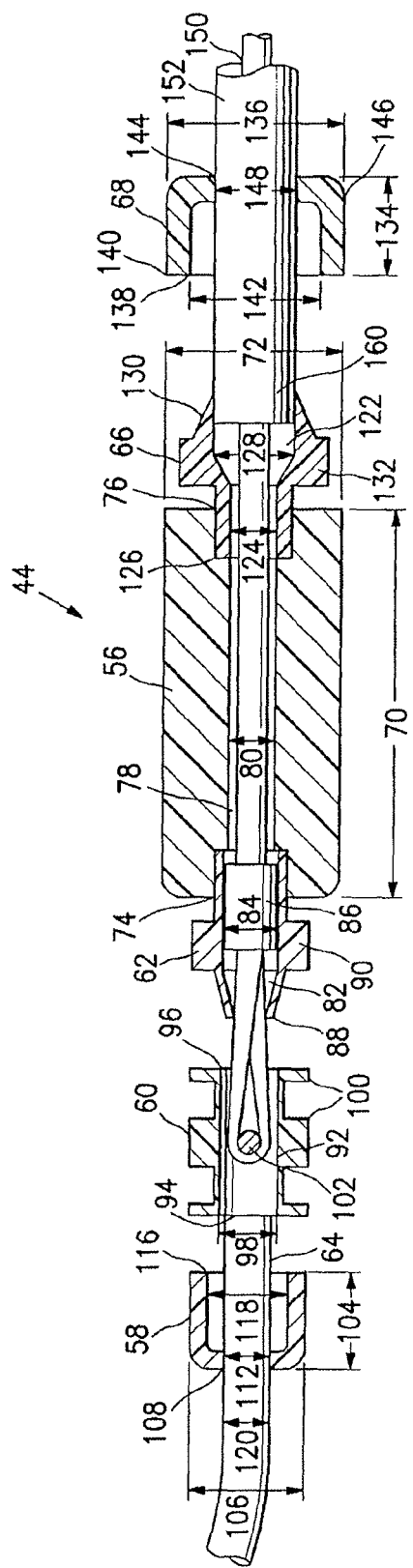
FIG. 2 is a cross-sectional side view of a handle of the deployment mechanism and a proximal end of a deployment member of the deployment mechanism.
Figure 4:
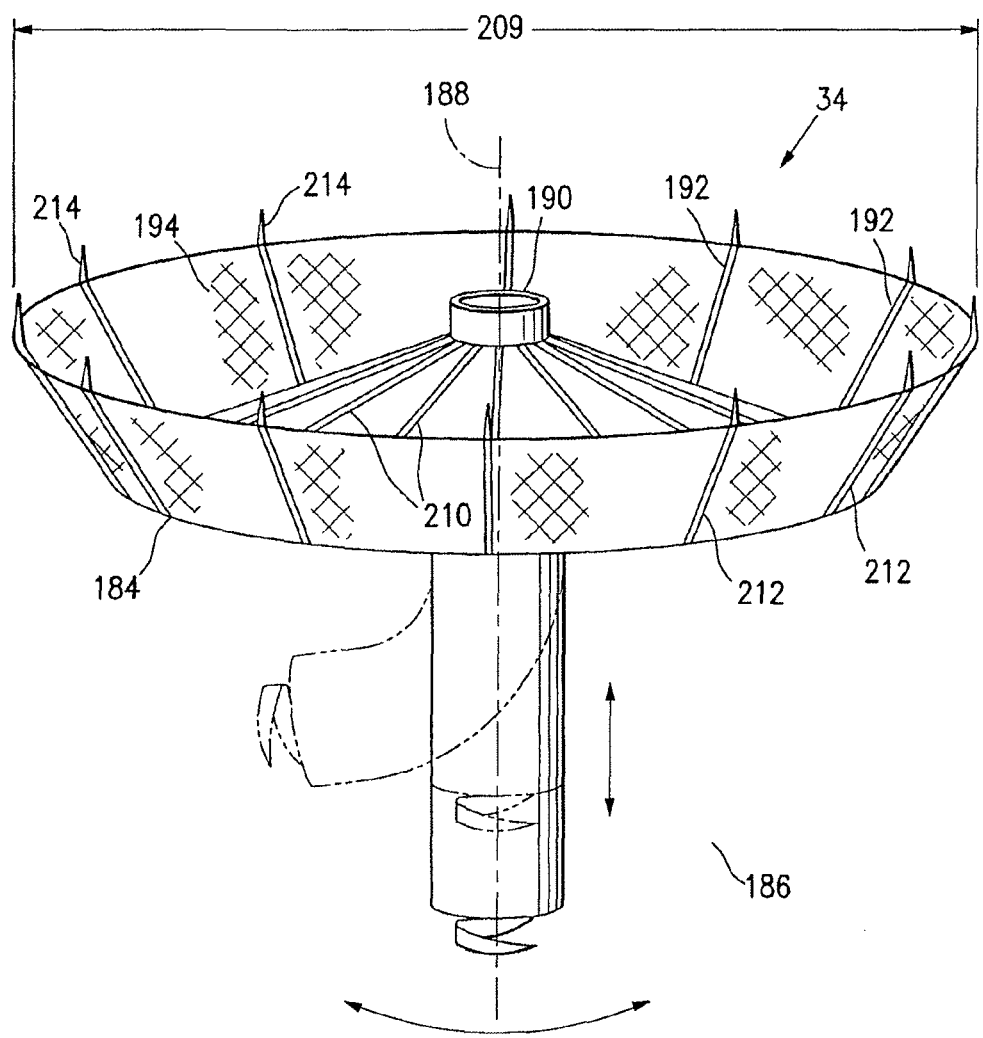
FIG. 4 is a perspective view of the cardiac device including a hub, a frame, and a stem thereof.
Figure 5A:
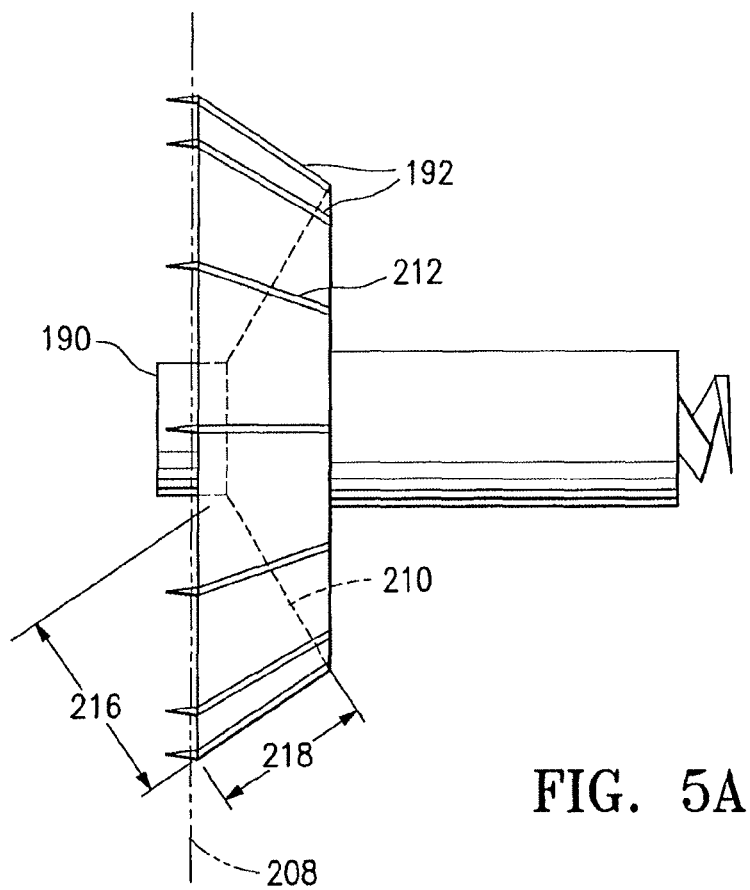
FIG. 5A is a side view of the cardiac device.
Figure 5B:
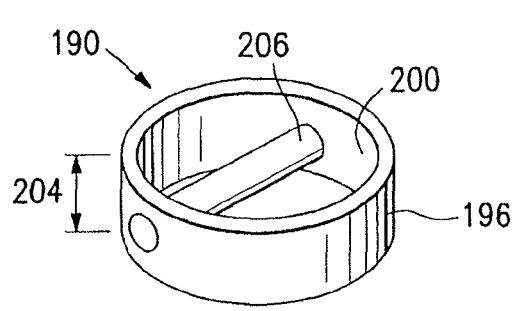
FIG. 5B is a perspective view of the hub.
Figure 5C:
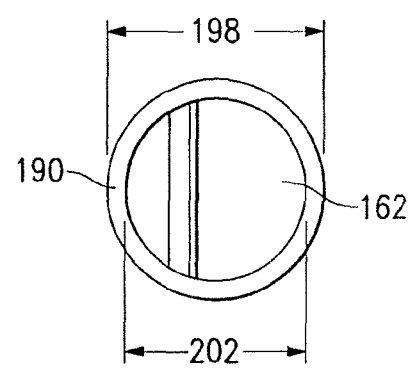
FIG. 5C is a top plan view of the hub.

FIGS. 2, 3A, 3B, and 3C illustrate the deployment mechanism 36 in more detail. FIG. 2 illustrates the handle 44 while FIGS. 3A, 3B, and 3C illustrate components at the distal end 54 of the deployment member 46. The components of the deployment mechanism 36 are primarily circular with center lines on a common axis.

The handle 44 is made of molded plastic and includes a main body 56, an anchor knob 58, an end piece 60, a proximal rotating hemostatic valve 62, a fluid line 64, a distal rotating hemostatic valve 66, and a detachment knob 68. The main body 56 is cylindrical with a length 70 of 80 mm and a diameter 72 of 25 mm. The main body 56 has a proximal 74 and a distal 76 opening at the respective ends thereof and a passageway 78 there through connecting the openings with an inner diameter 80 of 4 mm.

The proximal rotating hemostatic valve 62 is a cylindrical body with a passageway 82 there through having an inner diameter 84 of 4 mm, a locking hypo tube 86 within the passageway, a tapered outer end 88, and a raised formation 90 at a central portion thereof. The proximal rotating hemostatic valve 62 is rotationally secured to the proximal opening 74 of the handle 44. The locking hypo tube 86 is a cylindrical body secured within the passageway 82 of the proximal rotating hemostatic valve 62.

The end piece 60 is a cylindrical body with a passageway 92 there through connecting a proximal 94 and distal 96 opening at respective ends and having an inner diameter 98 of 5 mm. Raised formations 100 stand proud from respective central and outer portions of the end piece. A cylindrical end piece pin 102 is connected to an inner surface and extends across the inner diameter 98 of the passageway 92. The end piece pin 102 is made of stainless steel and has a length of 5 mm and a diameter of 2 mm. The distal opening 96 of the end piece 60 mates with the tapered outer end 88 of the proximal rotating hemostatic valve 62.

The anchor knob 58 is a cap-shaped body with a length 104 of 20 mm and an outer diameter 106 of 10 mm. The anchor knob 58 has a small opening 108 at a proximal end 110 with a diameter 112 of 4 mm and a large opening 114 at a distal end 116 with a diameter 118 of 6 mm. The anchor knob 58 fits over and is secured to both the end piece 60 and the proximal rotating hemostatic valve 62.

The fluid line 64 enters the handle 44 through the small opening 108 of the anchor knob 58 and is secured to the proximal opening 94 of the end piece 60. The fluid line 64 has an outer diameter 1 mm.

The distal rotating hemostatic valve 66 is a cylindrical body with a passageway 122 there through having a proximal inner diameter 124 of 4 mm at a proximal end 126 thereof and a distal inner diameter 128 of 5 mm at a distal end 130 thereof. The distal end 130 is tapered, and a raised formation 132 lies at a central portion thereof. The distal rotating hemostatic valve 66 is rotationally secured to the distal opening 76 of the main body 56.

The detachment knob 68 is a cap-shaped body with a length 134 of 20 mm and an outer diameter 136 of 20 mm. The detachment knob 68 has a large opening 138 at a proximal end 140 with a diameter 142 of 8 mm and a small opening 144 at a distal end 146 with a diameter 148 of 5 mm. The detachment knob 68 fits over and is secured to the distal rotating hemostatic valve 66.

Referring to FIGS. 3A-3C, the deployment member 46 includes an inner torque shaft 150 and an outer torque shaft 152. The inner torque shaft has a diameter 154 of 2 mm and is made of surgical stainless steel. The outer torque shaft is a hollow, cylindrical body with an inner diameter 156 of 3 mm and an outer diameter 158 of 5 mm. The outer torque shaft 152 is a polymer.

Referring again to FIG. 2, the inner torque shaft 150 passes through the detachment knob 68, through the distal rotating hemostatic valve 66, into and out of the passageway 78 of the main body 56, through the proximal rotating hemostatic valve 62, and into the end piece 60. The proximal end of the inner torque shaft 150 is wrapped around the end piece pin 102, reenters the proximal rotating hemostatic valve 62, and is attached to the locking hypo tube 86 within the proximal rotating hemostatic valve 62.

The outer torque shaft 152 is coaxial with and surrounds the inner torque shaft 150. A proximal end 160 of the outer torque shaft 152 passes into the distal hemostatic valve 66 and is secured thereto.

The distal end 54 of the deployment member 46 includes a key 162, a detachment screw 164, and a securing mechanism 166. A distal end 168 of the inner torque shaft 150 extends out of a distal end 170 of the outer torque shaft 152, and the key 162 is attached thereto. The key 162 is rectangular with a length 171 of 7 mm and a height 172 of 3 mm. The key 162 has a semi-circular cross section with a radius 174 of 1.5 mm. The detachment screw 164 is attached to the distal end 170 of the outer torque shaft 152, extends to a length 176 of 7 mm, and has a diameter 178 of 5 mm.

The securing mechanism 166 includes an inner component 180 and an outer component 182. The inner component 180 is a raised cylindrical portion coaxial with and on the inner torque shaft 150. The inner component 180 stands proud of the inner toque shaft 150 by 0.5 mm. The outer component 182 is a hollow, cylindrical body secured to an inner surface of the outer torque shaft 152 and has proximal and distal openings with diameters of 2.25 mm so that the inner toque shaft 150 cannot move axially relative to the outer torque shaft 152.

FIGS. 4, 5A-5C, and 6 illustrate the cardiac device 34 in more detail. The cardiac device 34 includes a frame 184 and a stem 186, or flexible body, and has a vertical axis 188.

The frame 184 includes a frame hub 190, a plurality of main segments 192, and a membrane 194. The hub 190 is a ring-shaped body with an outer surface 196 with a diameter 198 of 5 mm, an inner surface 200 with a diameter 202 of 4 mm, a thickness 204 of 3 mm, and a pin 206 extending off-center across the inner surface 200 creating a smaller and a larger gap. The pin 206 has a length of 3.5 mm and a diameter of 1 mm and is located in a plane 208. The frame 184 has a diameter 209 of approximately 25 mm; however, other embodiments may have diameters of between 10 mm and 100 mm. The entire hub 190 is made of nickel titanium.

The main segments 192 include first portions, or central segments, 210, second portions, or outer segments, 212, and passive anchors 214. The first portions 210 are connected to the hub 190 at a central portion of the outer surface 196 and extend radially from the hub 190 at an angle away from the plane 208 of the pin 206 to a length 216 of 8 mm. The second portions 212 of the segments 192 are connected to ends of the first portions 210 and further extend radially from the hub 190 but at an angle towards the plane 208. The second portions 212 each have a length 218 of 5 mm. The passive anchors 214 are formed at an end of each of the second portions 212. The passive anchors 214 have sharp ends that point slightly radially from the hub 190. The segments 192 are made from nickel titanium, which after a prescribed thermal process, allows for the segments 192 to hold their shape as illustrated, for example, in FIG. 4. The entire frame 184, or just portions of the frame 184, may also be made of stainless steel.

The membrane 194 is stretched over the first 210 and second 212 portions of the segments 192 to give the frame 184 a disk like shape. The membrane 194 is made of expanded Poly Tetra Fluoro Ethylene (ePTFE) and has a thickness of 0.08 mm. Other embodiments may use a mesh membrane.

Figure 6:
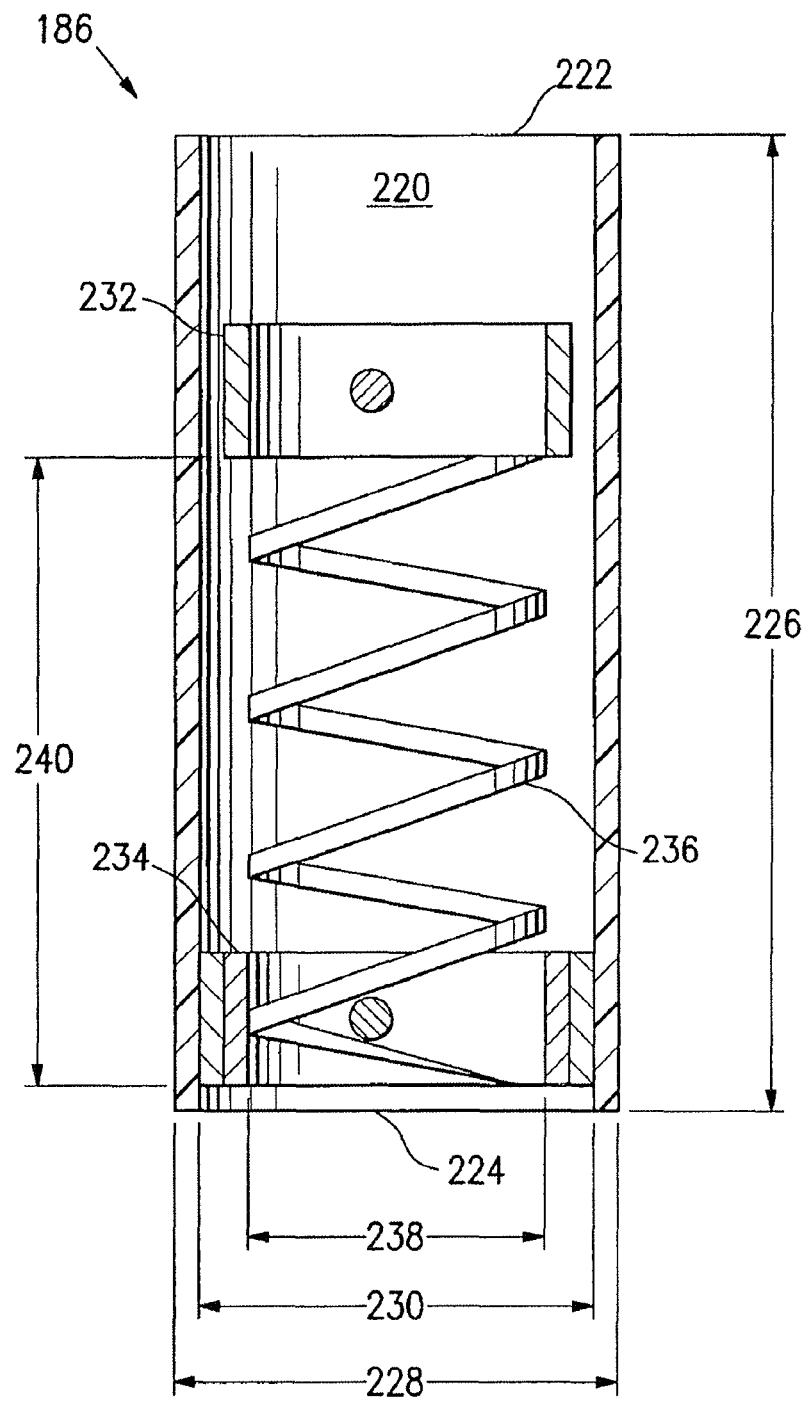
FIG. 6 is a cross-sectional side view of the stem.
Figure 7A:
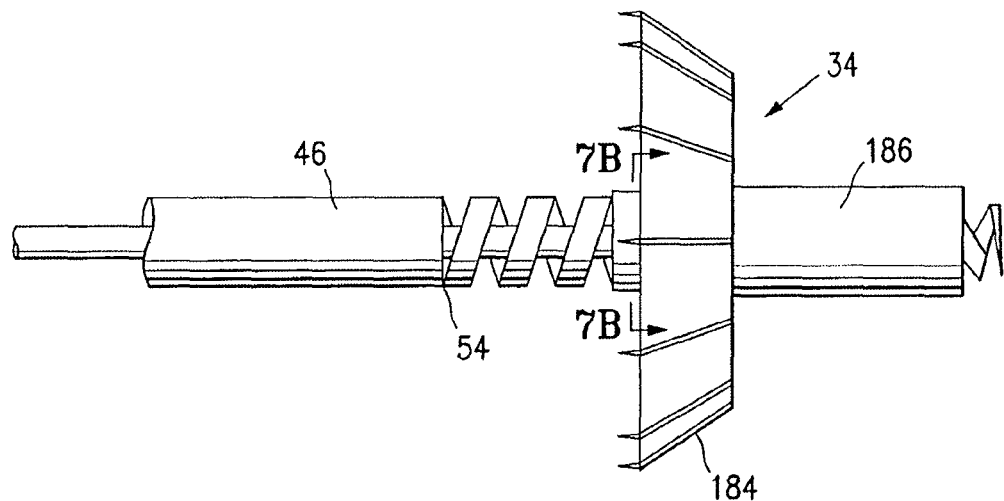
FIG. 7A is a side view of the distal end of the deployment member connected to the cardiac device.
Figure 7B:
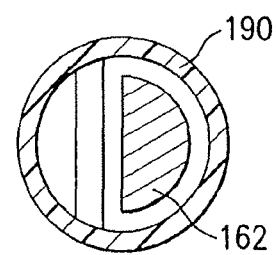
FIG. 7B is a cross-sectional view on 7B-7B in FIG. 7A of the cardiac device.

FIG. 6 illustrates the stem 186 unattached to the frame 184. The stem 186 is a hollow, cylindrical body with a passageway 220 there though connecting a proximal 222 and a distal 224 opening. The stem 186 has a height 226 of 9 mm, an outer diameter 228 of 5 mm, and an inner diameter 230 of 4 mm. The stem 186 includes a first hub 232 and a second hub 234, both similar to the hub 190 on the frame 184. The second hub 234 is secured within the passageway 220 near the distal opening 224 of the stem 186. The first hub 232 is loose within the stem 186 so that it may move, and has an active anchor 236, in the shape of a screw, attached. The active anchor 236 spirals from the first hub 232 to engage with the pin on the second hub 234. The active anchor 236 has a diameter 238 of 3.5 mm and a length 240 of 7 mm.

The stem 186 is made of Poly Tetra Fluoro Ethylene (PTFE) and is thus expandable and flexible. Referring again to FIG. 4, the stem 186 can be compressed or stretched by 30% of its length and can be bent from the vertical axis 188 of the device 34 by 120 degrees in any direction. The first hub 232, second hub 234, and active anchor 236 are made of nickel titanium. In other embodiments, the hubs may be made of stainless steel.

FIGS. 7A, 7B, 8, and 9 illustrate the system 30 with the stem 186 connected to the cardiac device 34 and the cardiac device 34 connected to the deployment mechanism 36. The stem 186 is fused to the frame hub 190 thus securing the stem 186 to the device 34.

Figure 8:
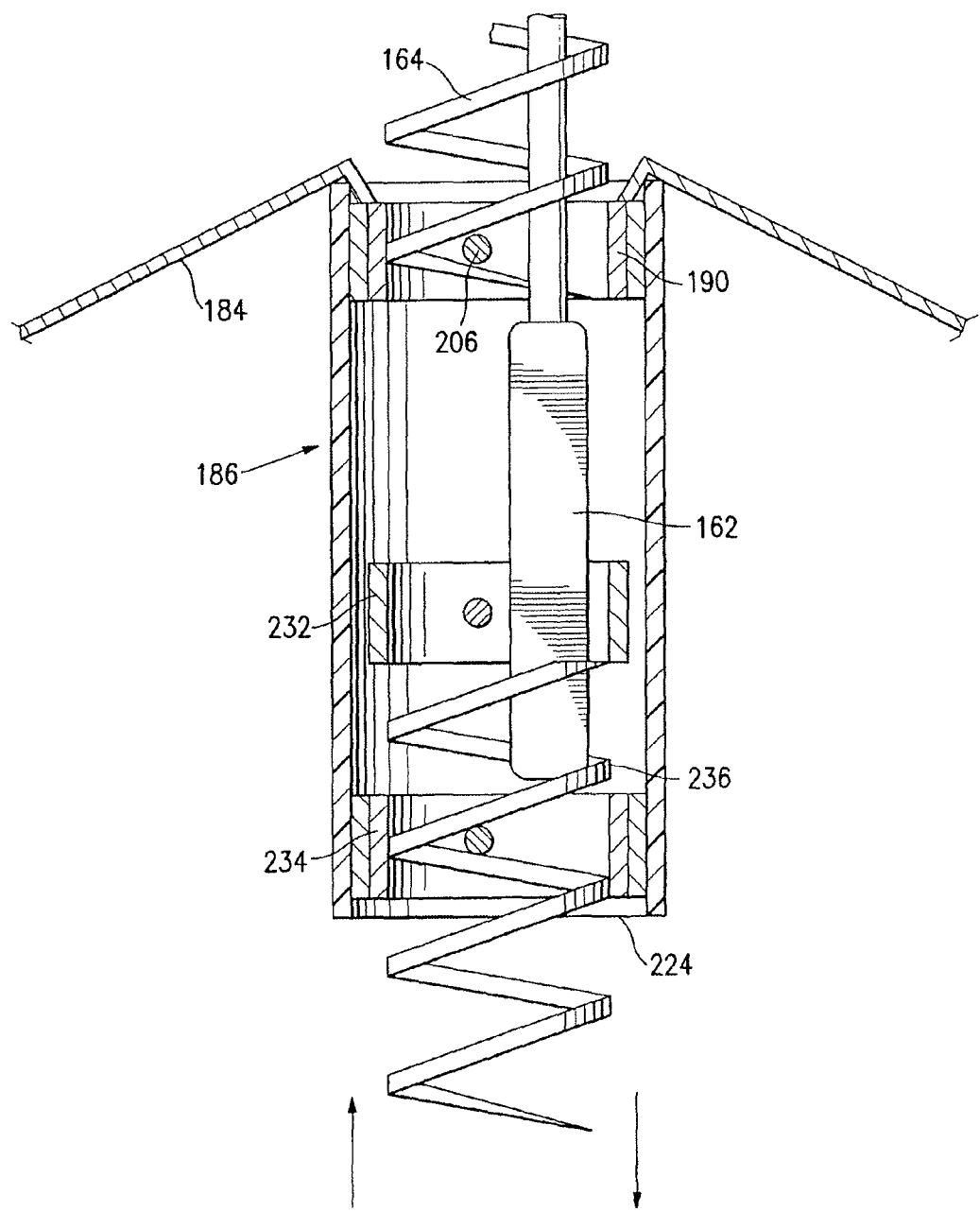
FIG. 8 is a cross-sectional side view of the cardiac device with the key connected thereto.
Figure 9:
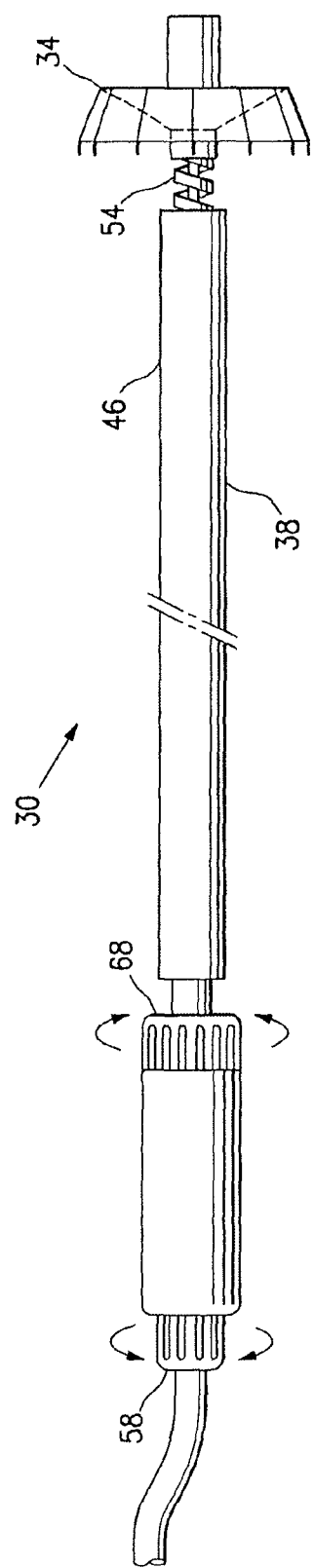
FIG. 9 is a side view of the system of FIG. 1 with the components integrated with and connected to one another.

In use, the deployment member 46 is inserted through the catheter tube 38 so that the distal end 54 of the deployment member 46 exits the distal end of the tube 38. As shown is FIGS. 7A and 7B, the deployment member 46 connects to the cardiac device 34 such that the key 162 engages the hub 190 of the frame 184*by* passing through the larger gap in the hub 190. As shown in FIG. 8, the key 162 passes through the hub 190 of the frame 184 to engage with the first hub 232 of the stem 186, but does not reach the second hub 234. Once the key 162 is fully inserted into the stem 186, the detachment knob 68 is turned which rotates the outer torque shaft 152 and thus the detachment screw 164 because the detachment screw 164 is attached to the outer torque shaft 152. The rotation thereof causes the detachment screw 164 to engage with the pin 206 of the frame hub 190, securing the cardiac device 34 to the deployment mechanism 36.

Rotation of the anchor knob 58 in a first direction causes the active anchor 236 to be deployed from the distal opening 224 of the stem 186 because the anchor knob 58 is connected to the inner torque shaft 150 which, in turn, is connected to the key 162. Rotation of the key 162 causes the first hub 232 to rotate and because the active anchor 236 is connected to the first hub 232 and engaged with the pin of the second hub 234, the active anchor 236 "twists" out of the distal opening 224 of the stem while the first hub 232 is pulled toward the distal opening 224. Rotation of the anchor knob 58 in a second direction causes the active anchor 236 to reenter the distal opening 224 of the stem 186.

As illustrated in FIGS. 10A and 10B, the distal end 54 of the deployment member 46 is then pulled into the distal end of the catheter tube 38. As a proximal section of the frame 184 enters the catheter tube 38, the first portions 210 of the segments 192 begin to collapse towards the stem 186. The segments 192 collapse, or fold, against a spring force that is created by the resilient nature of the nickel titanium material from which they are made. At the same time, the second portions 212 fan out radially away from the hub 190.

As illustrated in FIGS. 11A and 11B, by the time a distal section of the frame 184 and the second portions 212 of the segments 192 begin to enter the tube 38, the second portions 212 have been bent back to collapse towards the stem 186 similarly to the first portions 210.

FIGS. 12A and 12B illustrate the system 30 with the cardiac device 34 completely contained within the catheter tube 38.

FIGS. 13A-13J illustrates a human heart 242 while the cardiac device 34 is being deployed. The heart 242 contains a right ventricle 244 and a left ventricle 246 with papillary muscles 248 and an akinetic portion 250 with an apex 252. The distal end of the catheter 38 has been inserted through the aorta and aortic valve into the left ventricle 246 to a selected position where the cardiac device 34 can be deployed. The catheter tube 38 is then partially pulled off of the cardiac device 34 exposing the stem 186.

The active anchor 236 is then deployed by rotating the anchor knob 58 in a first direction. The active anchor 236 penetrates the myocardium of the heart 242 to secure the cardiac device 34 in the selected position at the apex 252 of the akinetic portion 250 of the left ventricle 246.

The catheter 38 is then completely removed from the distal end 54 of the deployment member 46, exposing the cardiac device 34. As the cardiac device 34 expands, due to the resilient nature of the segments 192 and the pre-set shape of the frame 184, the passive anchors 214 on the segments 192 penetrate the myocardium in a first direction. The membrane 194 seals a portion of the ventricle 246 and separates the ventricle 246 into two volumes.

If the cardiac device 34 has not been properly positioned, or if it is of the wrong size or shape for the particular heart, the device 34 may be repositioned or completely removed from the heart 242.

Rotation of the anchor knob 58 in a second direction will cause the active anchor 236 to be removed from the apex 252 of the akinetic portion 250 of the left ventricle 246 thus releasing the cardiac device 34 from the heart 242. The distal end 54 of the deployment member 46 may be retracted into the catheter 38 to once again fold the cardiac device 34 into the position shown in FIG. 12B, from where it can again be deployed. The passive anchors 214 are removed from the myocardium in a second direction which is approximately 180 degrees from the first direction so that minimal damage is done to the myocardium.

Figure 13A:
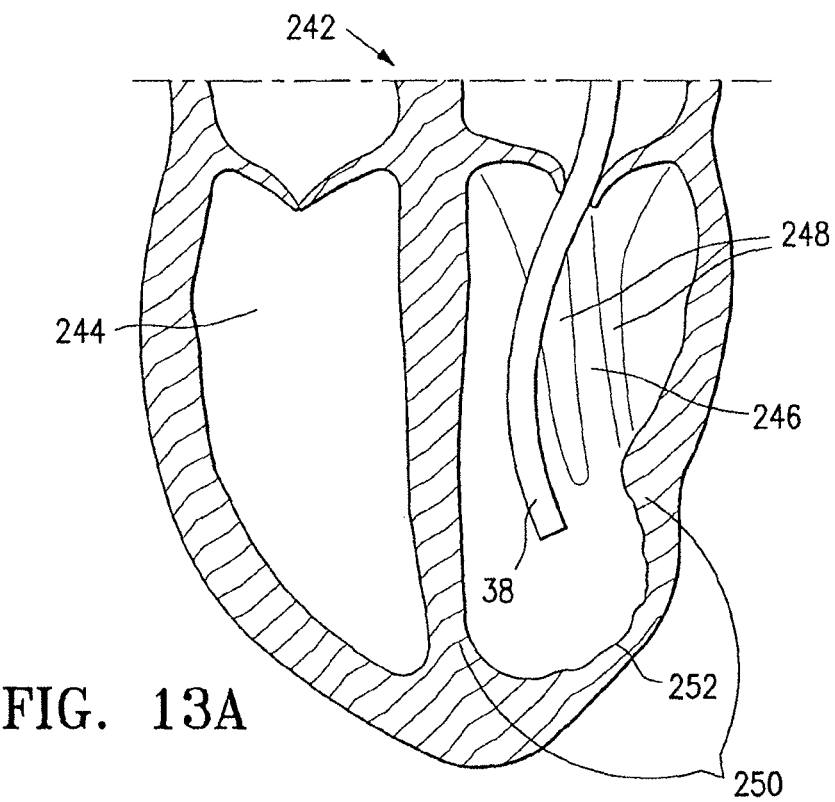
FIG. 13A is a cross-sectional side view of a human heart with the catheter inserted therein.
Figure 13B:
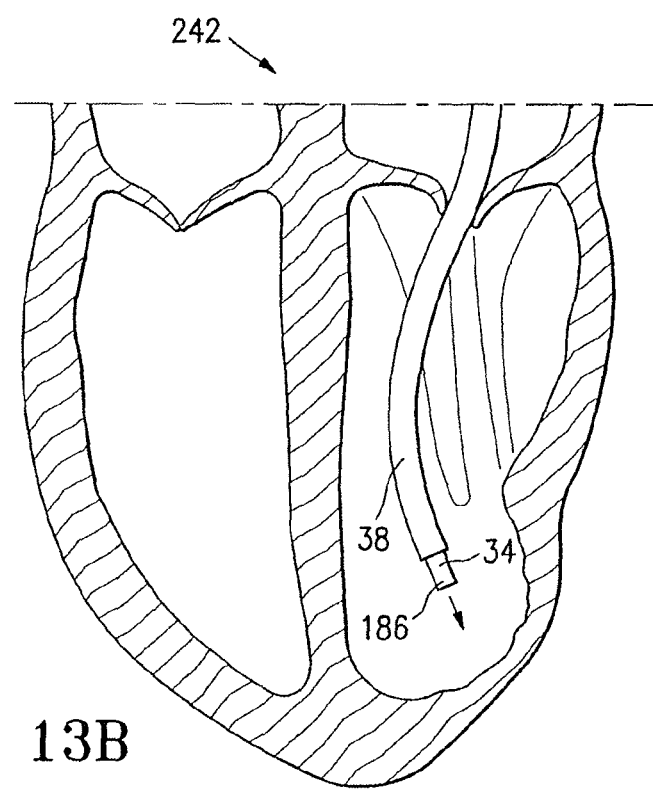
FIGS. 13B-13K are cross-sectional side views of the human heart illustrating installation (FIGS. 13B-13E), removal (FIGS. 13E-13H), and subsequent final installation (FIGS. 13I-13K) of the cardiac device.
Figure 13C:
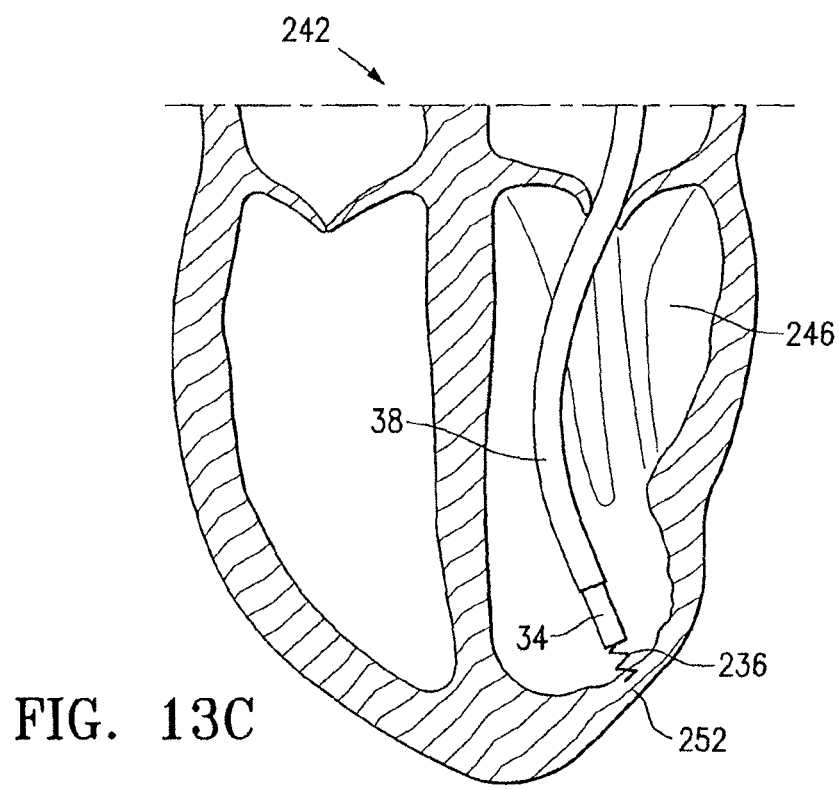
Figure 13D:
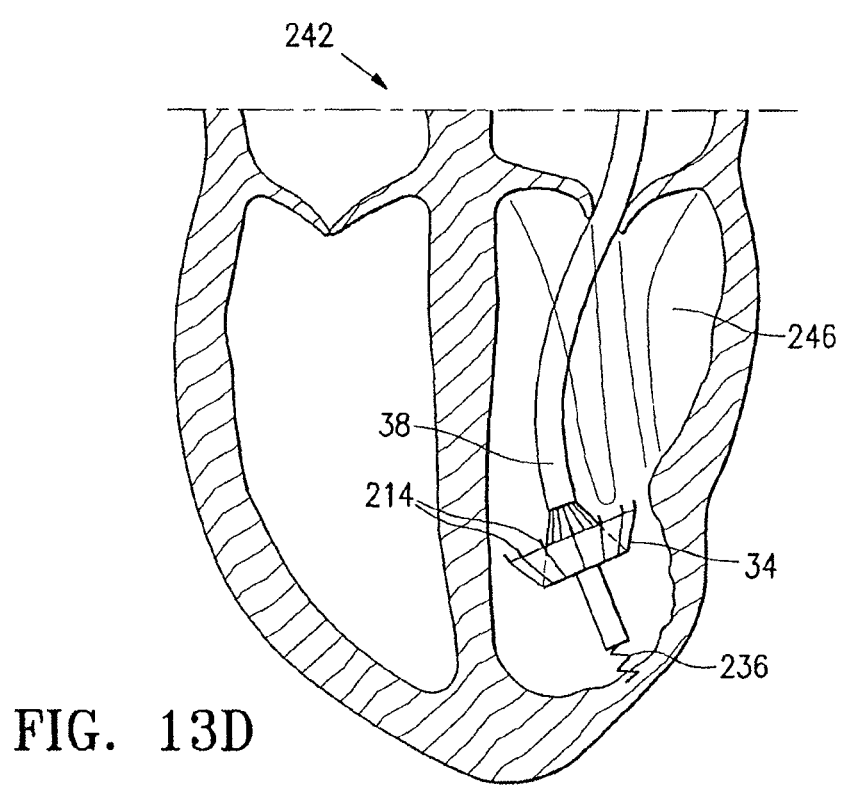
Figure 13E:
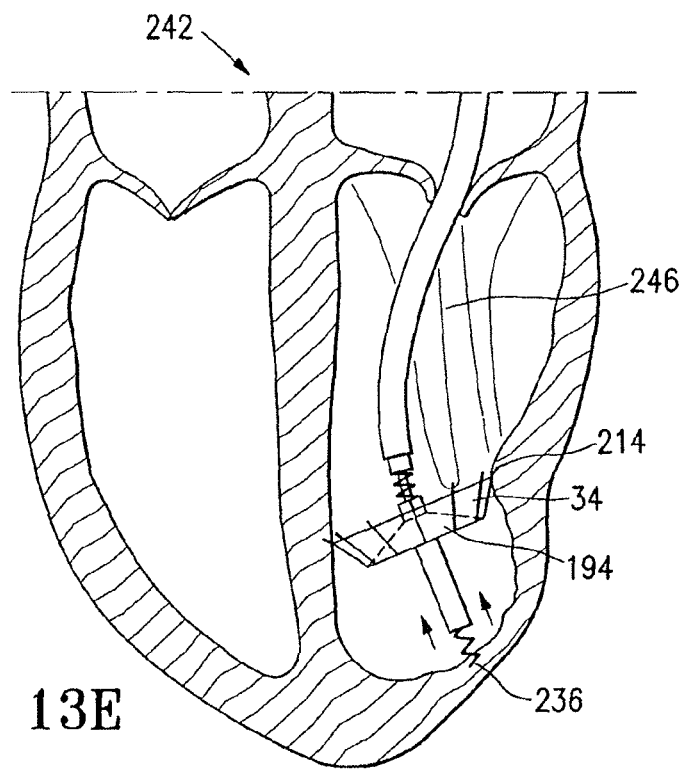
Figure 13F:
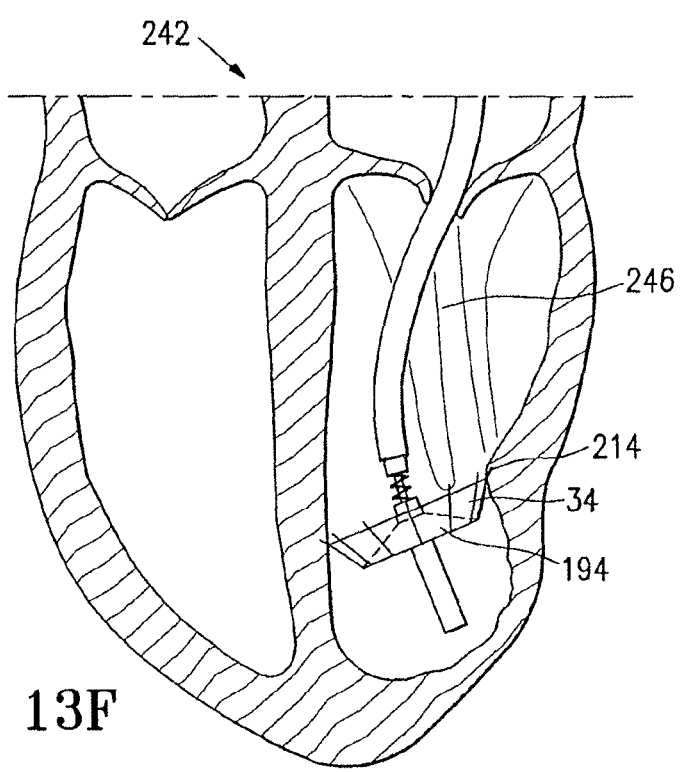
Figure 13G:
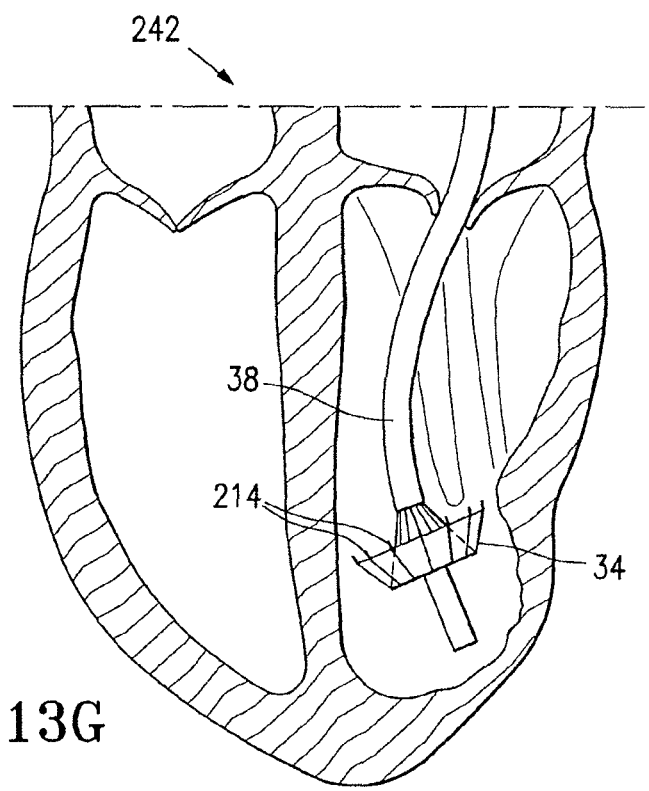
Figure 13H:
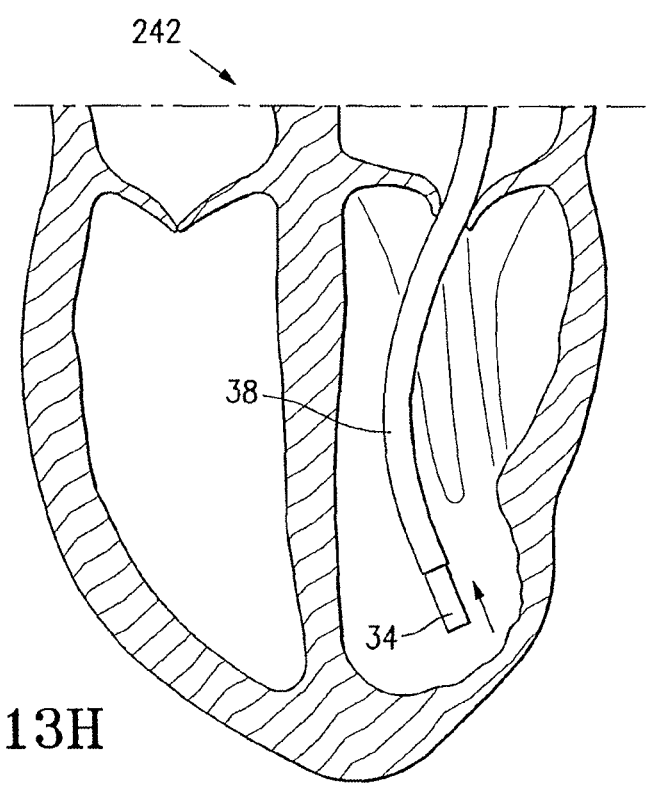
Figure 13I:
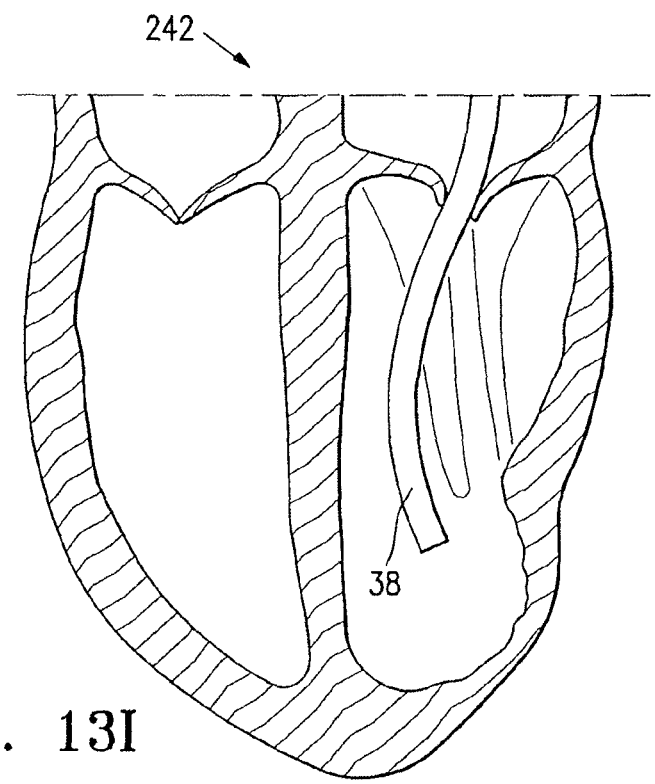
Figure 13J:
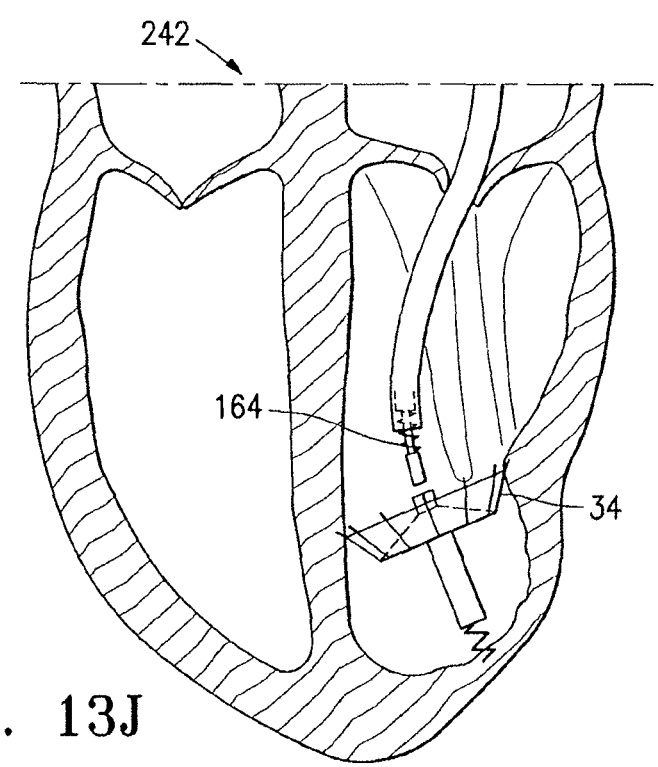
Figure 13K:
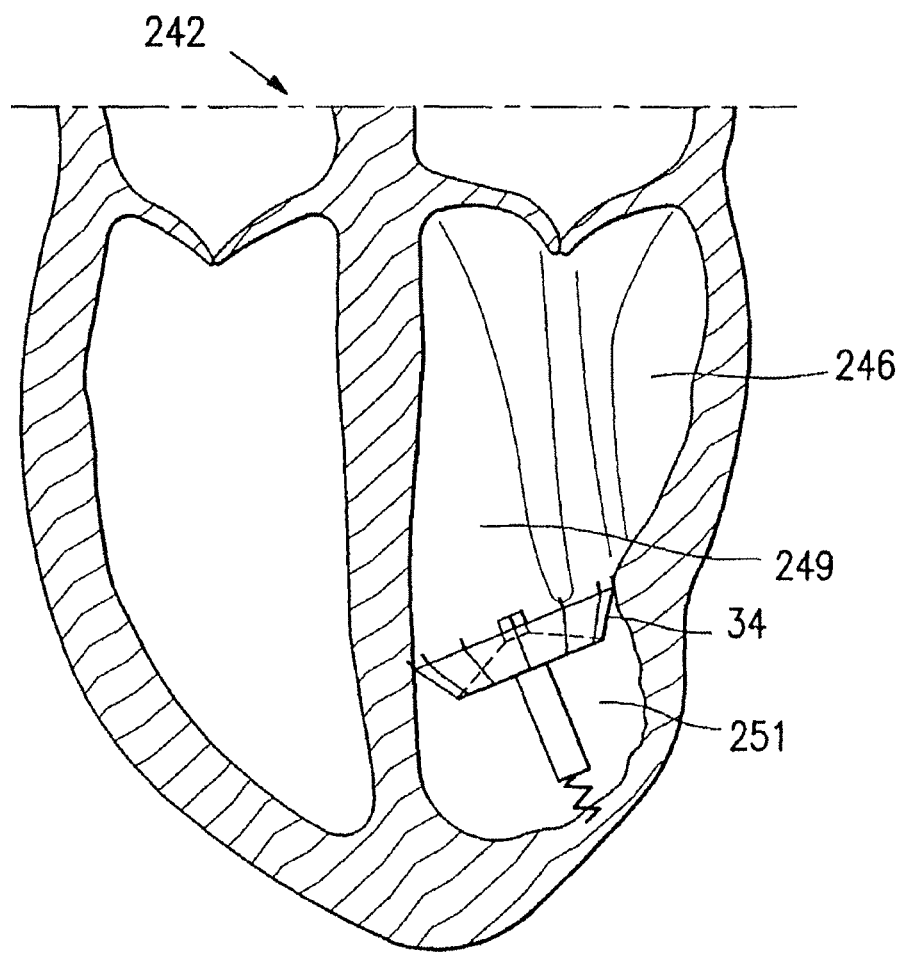

However, if the cardiac device 34 has been properly positioned and is of the proper size and shape, rotation of the detachment knob 68 in a second direction will cause the detachment screw 164 at the distal end 170 of the outer torque shaft 152 to disengage the pin 206 in the frame hub 190, thus releasing the deployment member 46 from the cardiac device 34 to allow removal of the deployment member 46 from the heart 242. FIG. 13K illustrates the heart 242 with the cardiac device 34 installed and the deployment mechanism 36 removed from the heart 242.

One advantage of this system is that the shape of the frame 184 allows the device 34 to be retrieved as long as the deployment member 46 is still connected to the device 34. When the device 34 is retrieved, the passive anchors 214 withdraw from the myocardium in a direction that is approximately 180 degrees from, or opposite, the first direction to minimize the amount of damage done to the myocardium. The device 34 also provides support for the akinetic region 250, minimizes the bulging of the akinetic region 250, and reduces stress on the working parts of the myocardium. A further advantage is that the ePTFE membrane 194 is biocompatible, has a non-thrombogenic surface, promotes healing, and accelerates endothelization.

Figure 14A:
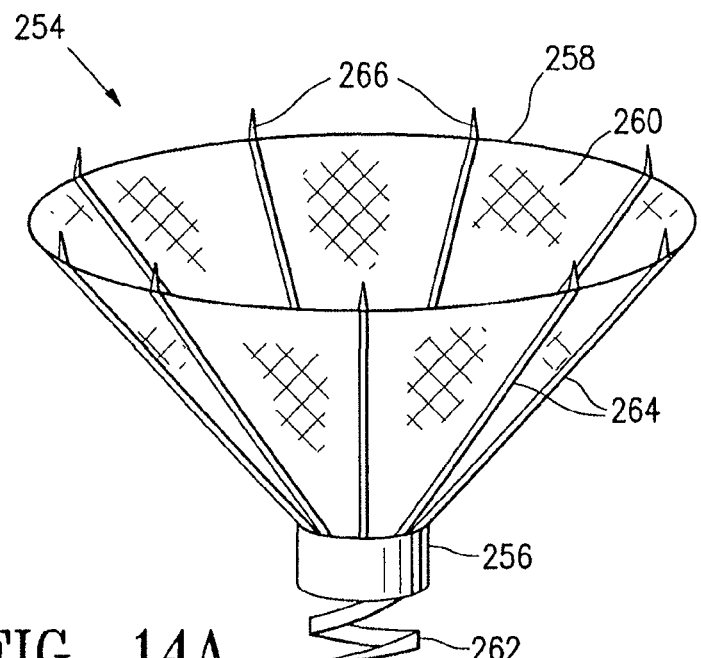
FIG. 14A is a perspective view of a cardiac device according to another embodiment of the invention.

FIG. 14A illustrates a cardiac device 254 according to another embodiment of the invention. The cardiac device includes a hub 256, a frame 258, and a membrane 260. The hub 256 lies at a central portion of the frame 258 and an active anchor 262 is connected to the hub 256 and extends downwards there from. The frame 258 includes a plurality of segments 264 which extend radially and upwardly from the hub 256. A sharp passive anchor 266 lies at the end of each of the segments 264. The membrane 260 is stretched between the segments 264 to form a cone-shaped body.

Figure 14B:
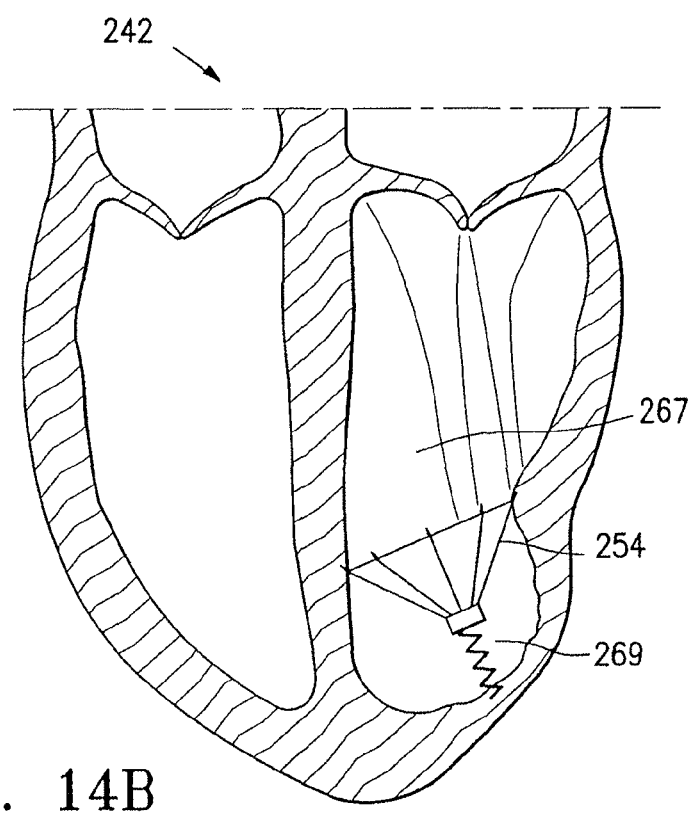
FIG. 14B is a cross-sectional side view of the human heart with the cardiac device of FIG. 14A installed.

FIG. 14B illustrates a human heart with the cardiac device 254 of FIG. 14A having been secured to an akinetic portion thereof.

Figure 15A:
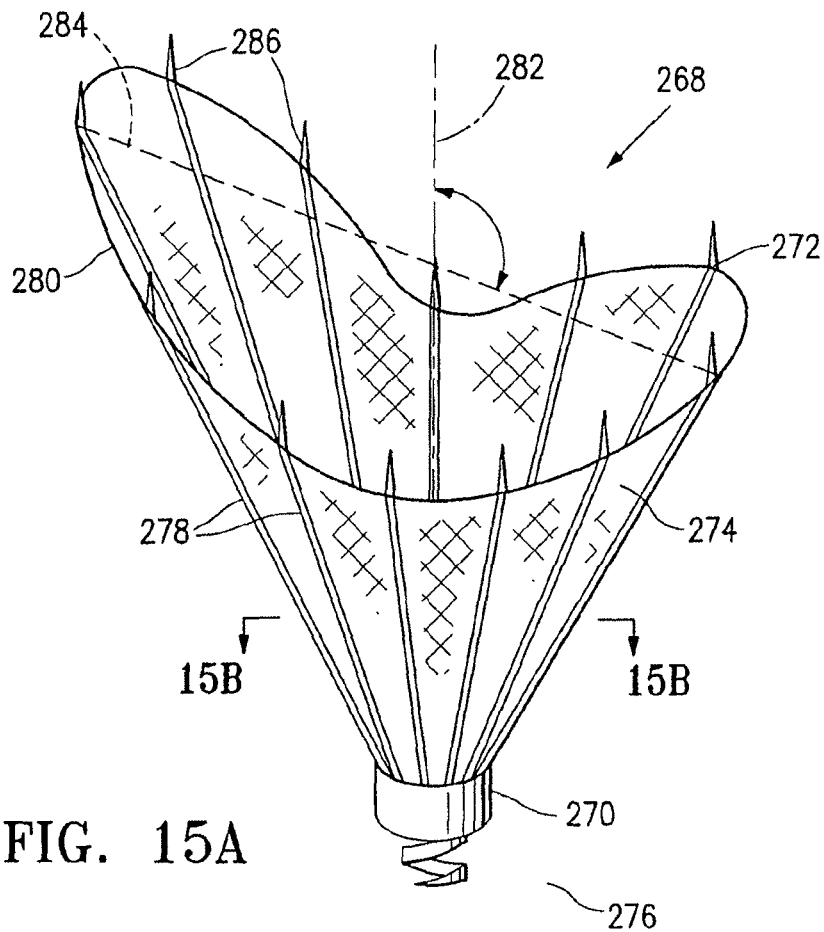
FIG. 15A is a perspective view of a cardiac device according to a further embodiment on the invention.
Figure 15B:
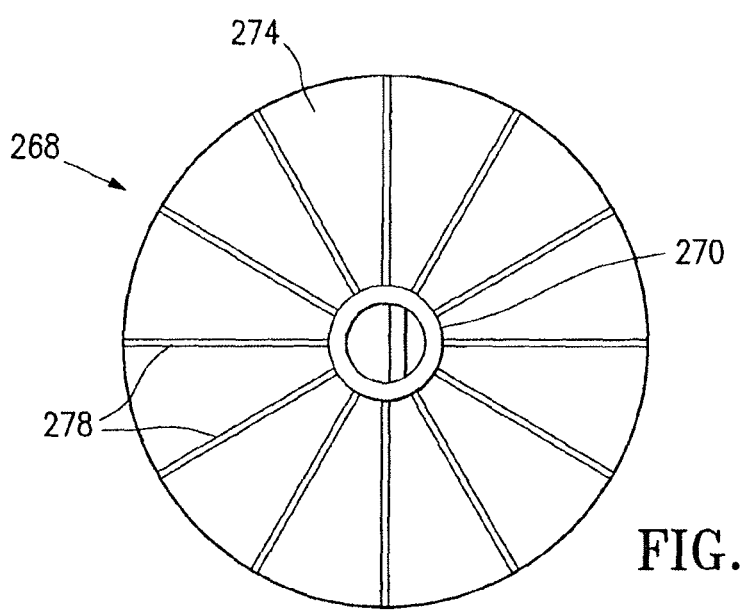
FIG. 15B is a cross-sectional top plan view of the cardiac device on 15B-15B in FIG. 15A.

FIG. 15A and FIG. 15B illustrate a cardiac device 268 according to a further embodiment of the invention. The cardiac device includes a hub 270, a frame 272, and membrane 274. The hub 270 lies at a central portion of the frame 272 and an active anchor 276 extends downwardly from the hub 270. The frame 272 includes a plurality of segments 278 which extend radially and upwardly from the hub 270. The segments 278 are of different lengths such that an outer edge 280 of the cardiac device 268 is not planar. The device 268 has a vertical axis 282 which intersects a diameter 284 across the outer edge 280 of the device 268 at an angle other than 90 degrees. A sharp passive anchor 286 lies at the end of each of the segments 278. The membrane 274 is stretched between the segments 278 to form a cone-shaped body. Referring specifically to FIG. 15B, a cross-section perpendicular to the vertical axis 282 of the device 268 is circular.

Figure 15C:
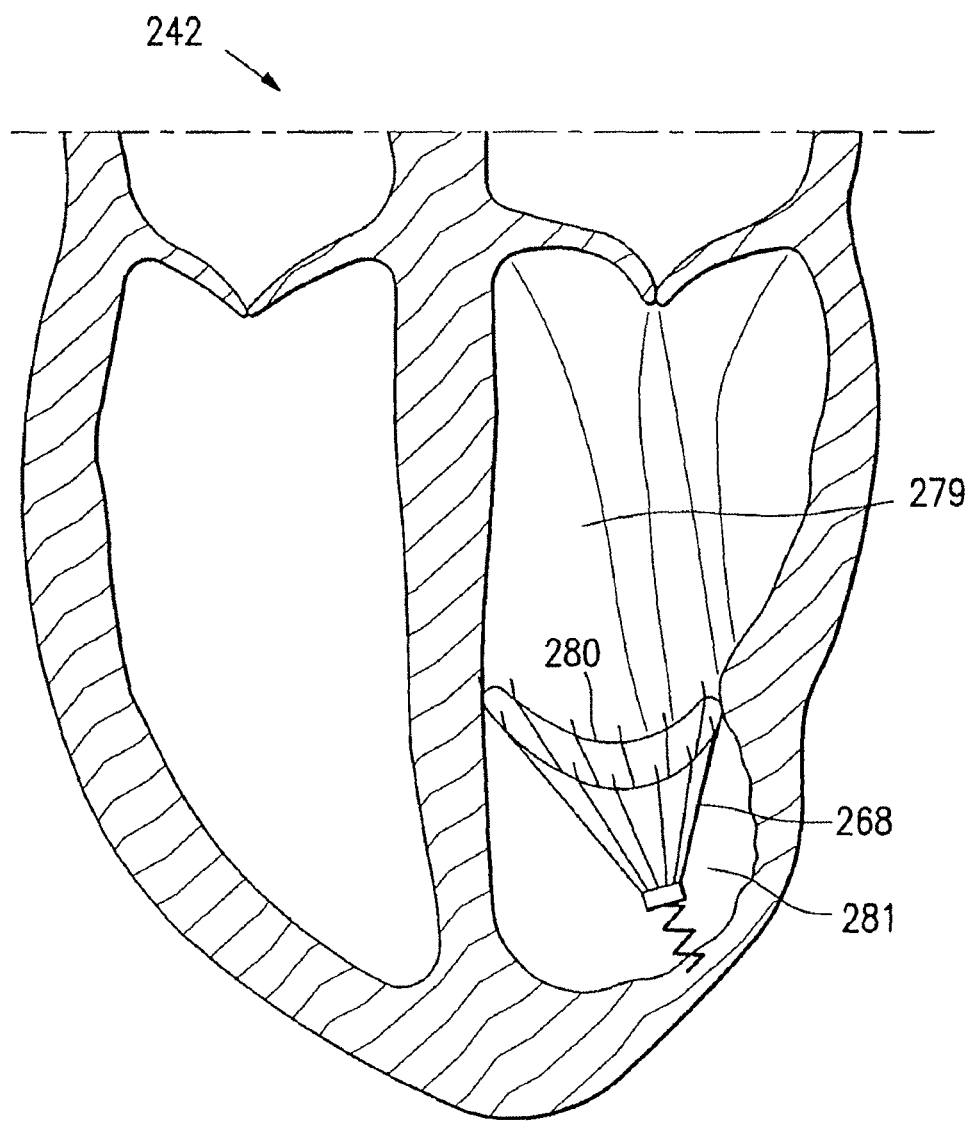
FIG. 15C is a cross-sectional side view of the human heart with the cardiac device of FIG. 15A installed.

FIG. 15C illustrates a human heart with the cardiac device 268 of FIG. 15A having been secured to an akinetic portion thereof. The outer edge 280 of the cardiac device 268 defines a non-planar cross-section of an inner surface of the left ventricle.

A further advantage of this embodiment is that the device 268 can be sized and shaped for use on a wider variety of akinetic portions in left ventricles.

Figure 16A:
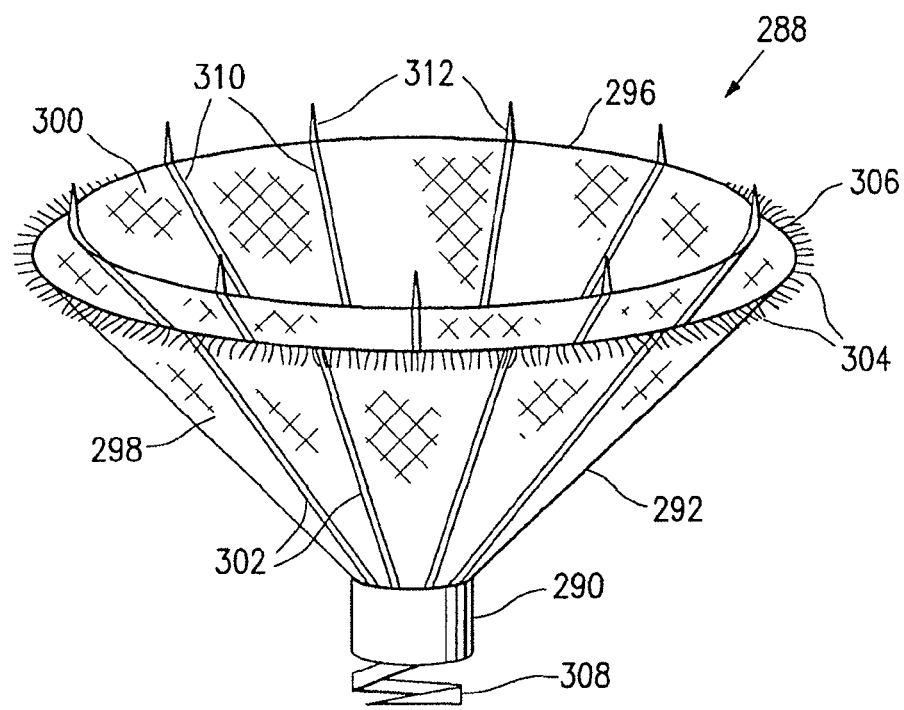
FIG. 16A is a perspective view of a cardiac device according to a further embodiment of the invention.
Figure 16B:
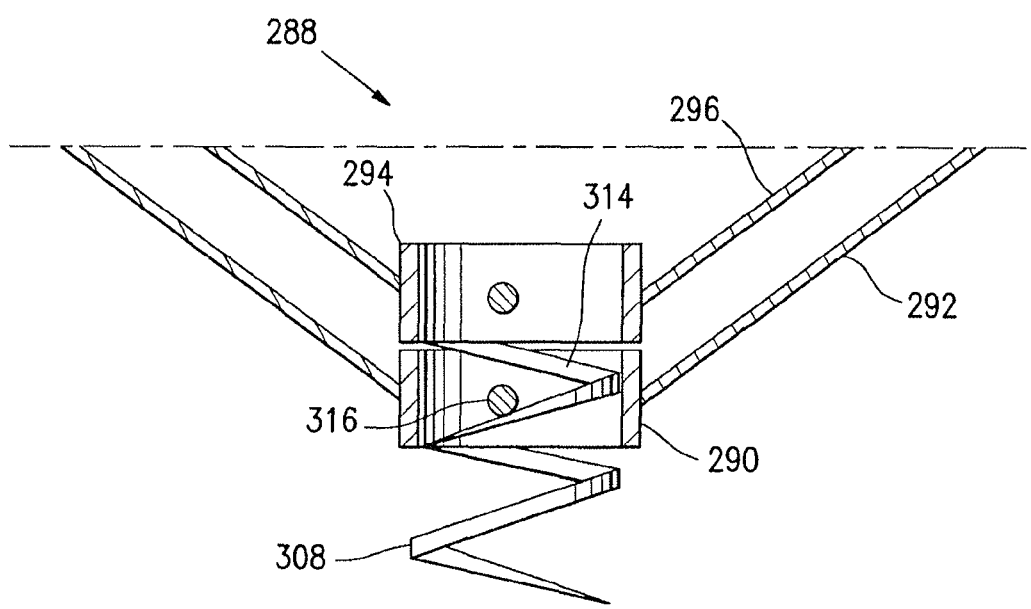
FIG. 16B is a cross-sectional side view of the cardiac device of FIG. 16A.

FIG. 16A and FIG. 16B illustrate a cardiac device 288 according to a further embodiment of the invention. The cardiac device 288 includes a first hub 290, a first frame 292, a second hub 294, a second frame 296, a first membrane 298, and a second membrane 300. The first hub 290 is attached to a central portion of the first frame 292. A plurality of segments 302 extend radially from and upwards from the first hub 290. The first membrane 298 is occlusive and made of a thrombogenic material and stretched between the segments 302 to form a first cone-shaped body. A plurality of fibers 304 extend radially from an outer edge 306 of the first cone-shaped body. An active anchor 308 extends down from the first hub 290.

The second frame 296 includes a plurality of segments 310 extending radially and upwardly from the second hub 294 and end in sharp passive anchors 312. An attachment screw 314, similar to the detachment screw 164, extends downwards from the second hub 294. Referring specifically to FIG. 16B, the attachment screw 314 is rotated so that it engages a pin 316 within the first hub 290, similarly to the frame hub 190 already described, to secure the second frame 296 to the first frame 292. The second membrane 300 is made of ePTFE and stretched between the segments 310 to form a second cone-shaped body.

Figure 16C:
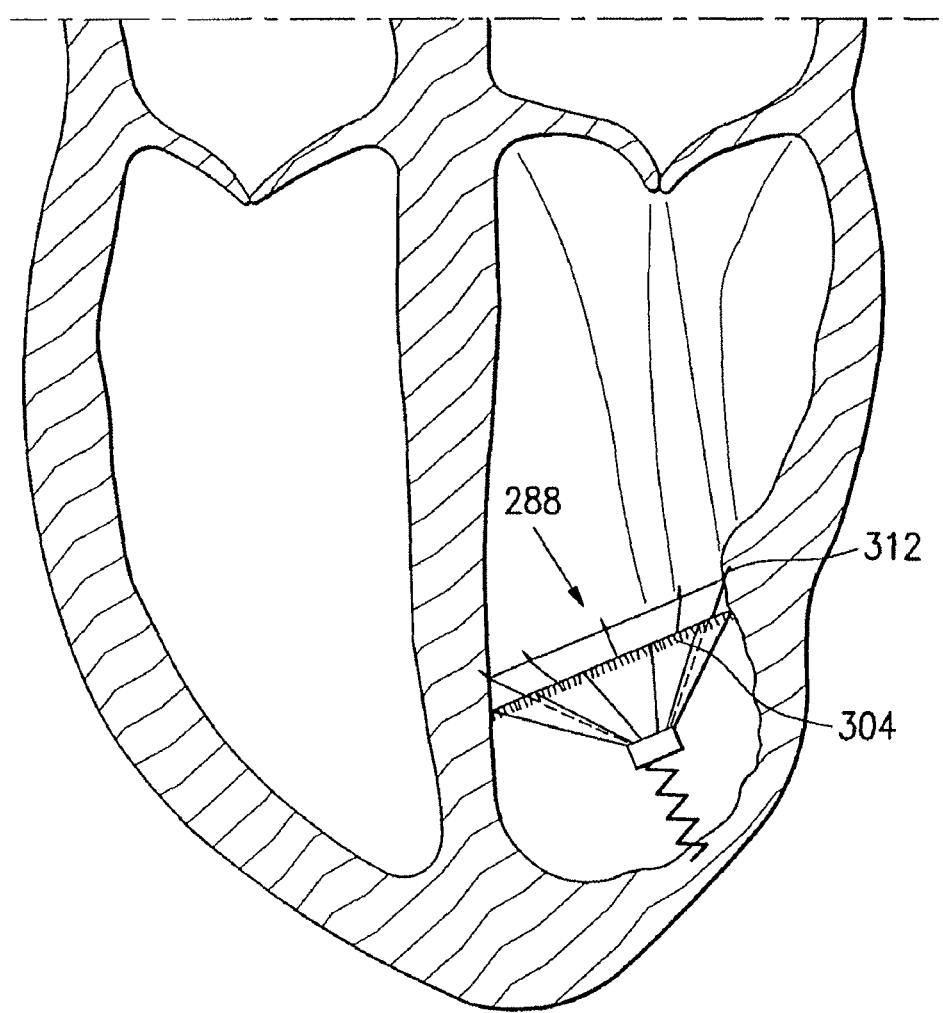
FIG. 16C is a cross-sectional side view of the human heart with the cardiac device of FIG. 16A installed.

FIG. 16C illustrates a human heart with the cardiac device 288 of FIG. 16A secured to an akinetic portion thereof. The fibers 304 on the outer edge 306 of the first frame 292 are interacting with an inner surface of the left ventricle to seal off the volume below the outer edge 306 of the first frame 292. The passive anchors 312 on the ends of the segments 310 of the second frame 296 have penetrated the myocardium to hold the device 288 in place.

A further advantage of this embodiment is that the fibers 304 of the first membrane 298 interface with trabeculae and further block the flow of blood into the apex of the akinetic portion.

Figure 17A:
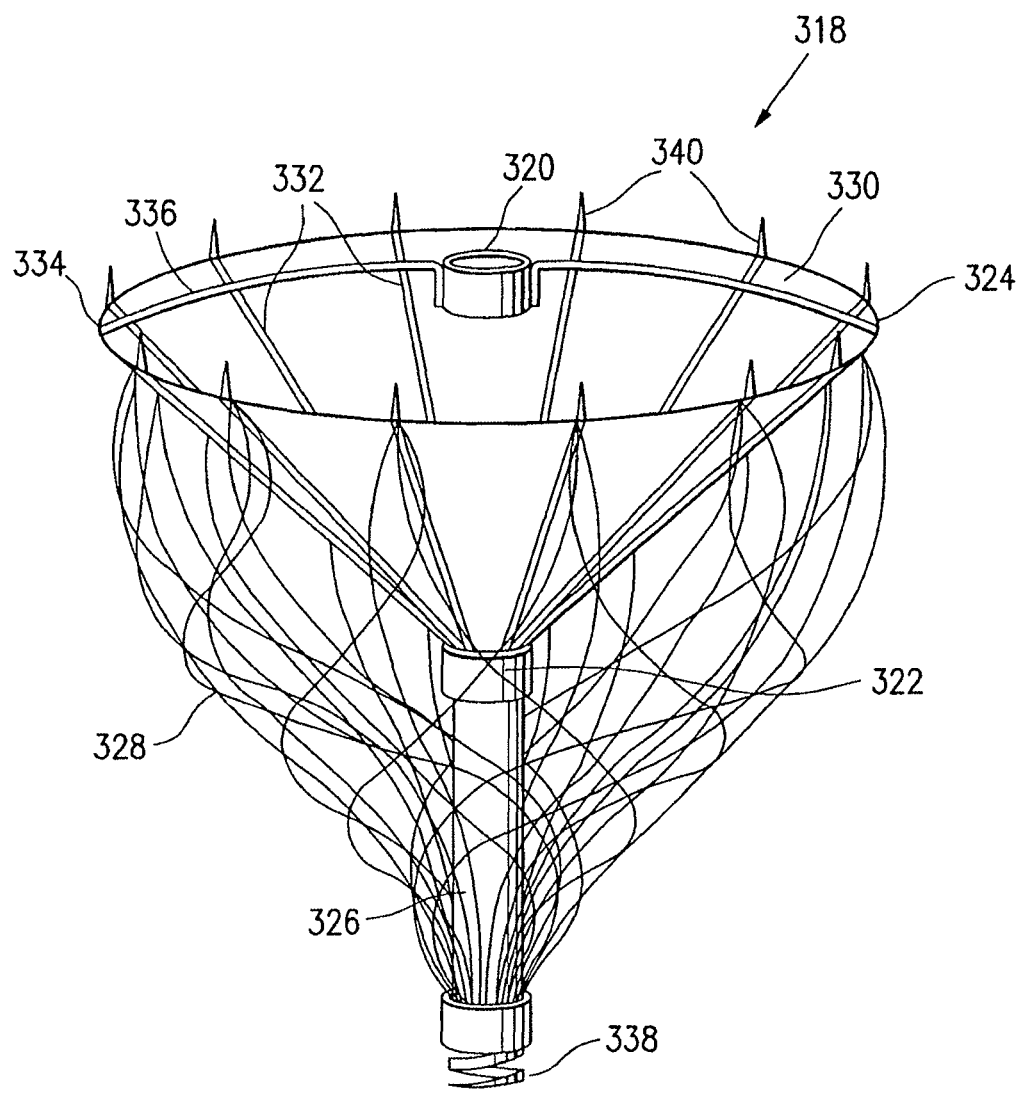
FIG. 17A is a perspective view of a cardiac device according to a further embodiment of the invention.

FIG. 17A illustrates a cardiac device 318 according to a further embodiment of the invention. The cardiac device 318 includes proximal 320 and distal 322 hubs, a frame 324, a stem 326, a braided structure 328, and a membrane 330. The frame 324 includes a plurality of segments 332 extending radially and upwards from the distal hub 322, and the membrane 330 is stretched between the segments 332 to form a cone-like body having an outer edge 334. Two extra segments 336 extend across the outer edge 334 of the cone-like body and are connected to and support the proximal hub 320 above the distal hub 322. The stem 326, including an active anchor 338, extends downwards from the distal hub 322. The braided structure 328 is made of nickel titanium and is connected to a distal end of the stem 326 into the ends of the segments 332. The segments 332 end in sharp passive anchors 340. The braided structure 328 may also be made of a biodegradable material or a polymer.

Figure 17B:
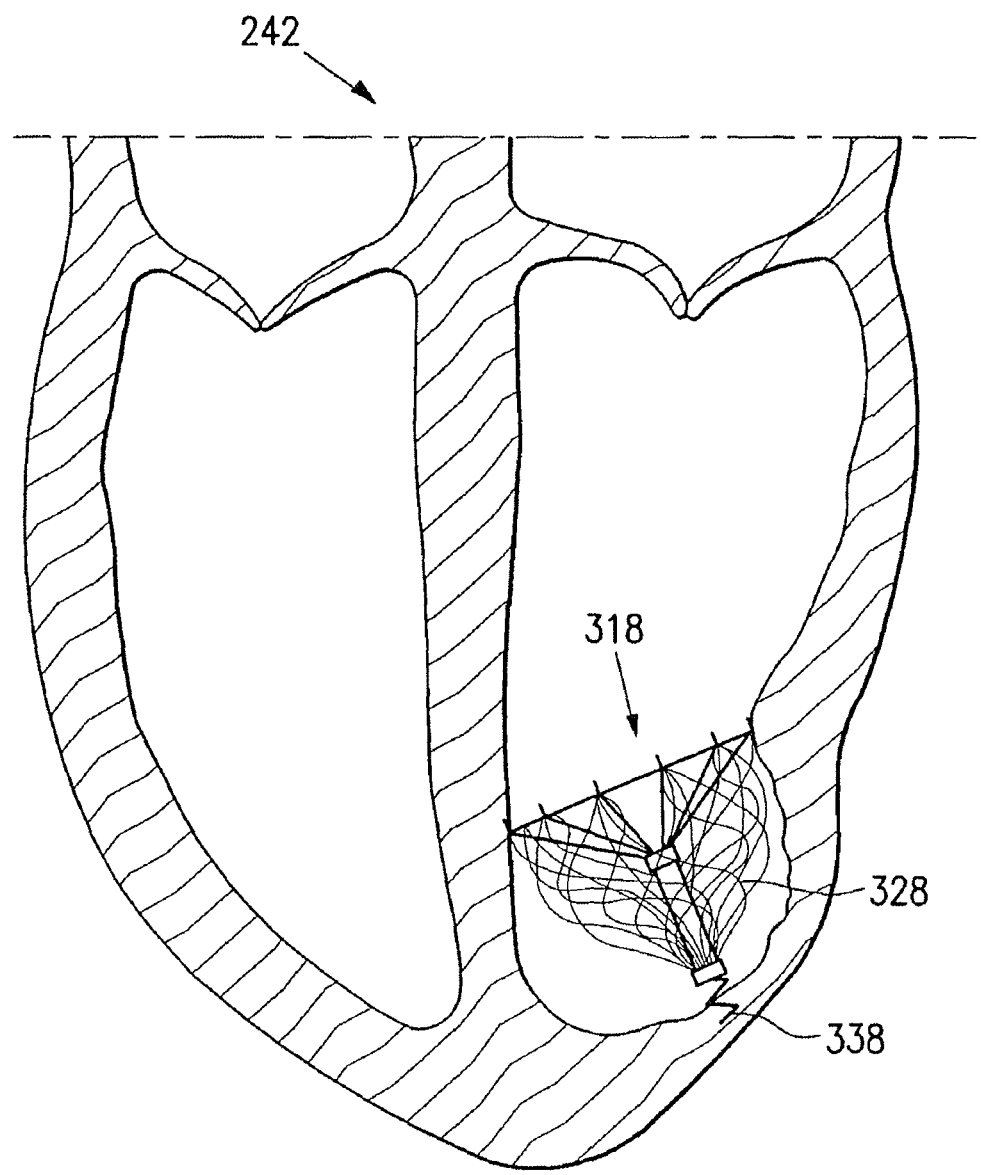
FIG. 17B is a cross-sectional side view of the human heart with the cardiac device of FIG. 17A installed.

FIG. 17B illustrates a human heart with the cardiac device 318 of FIG. 17A having been secured to an akinetic portion thereof. The braided structure 328 presses against an inner surface of the left ventricle.

A further advantage of this embodiment is that the braided structure 328 allows the device to "nestle" into position before the active anchor 338 is deployed to secure the device 318 in place. Further advantages are that the braided structure 328 adds structural stability to the device 318 and the nickel titanium of the braided structure 328 provides a mechanism for containing thrombi in the static chamber.

Figure 18A:
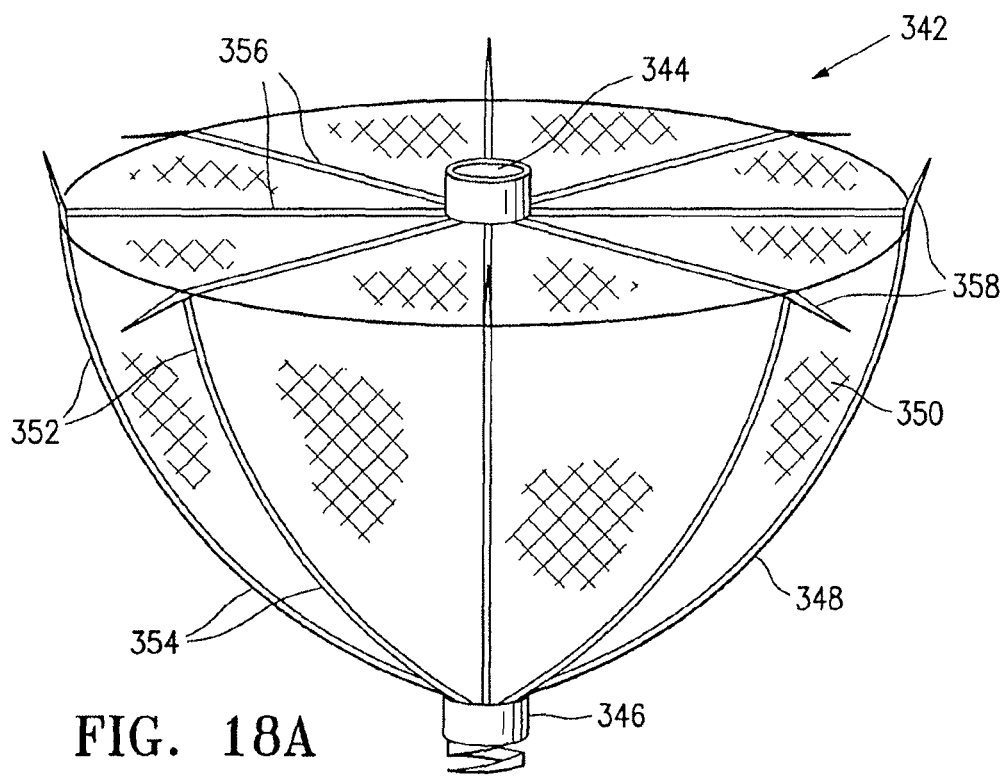
FIG. 18A is a perspective view of a cardiac device according to a further embodiment of the invention.

FIG. 18A illustrates a cardiac device 342 according to a further embodiment of the invention. The cardiac device 342 includes proximal 344 and distal 346 hubs, a frame 348, and a membrane 350. A plurality segments 352, having first 354 and second 356 portions, extend upwardly and radially from the distal hub 346 in a curved fashion and are bent and extend inwards to meet at the proximal hub 344. The membrane 350 is stretched across the segments 352 to form a semi-circular or basket-shaped body. Sharp passive anchors 358 extend from the segments 352 between the first 354 and second 356 portions.

Some of the passive anchors 358 extend in a primarily axial direction with a small radial component, and some of the passive anchors 358 extend in a primarily radial direction with a small axial component. Other embodiments may have both types of passive anchors on a single segment.

Figure 18B:
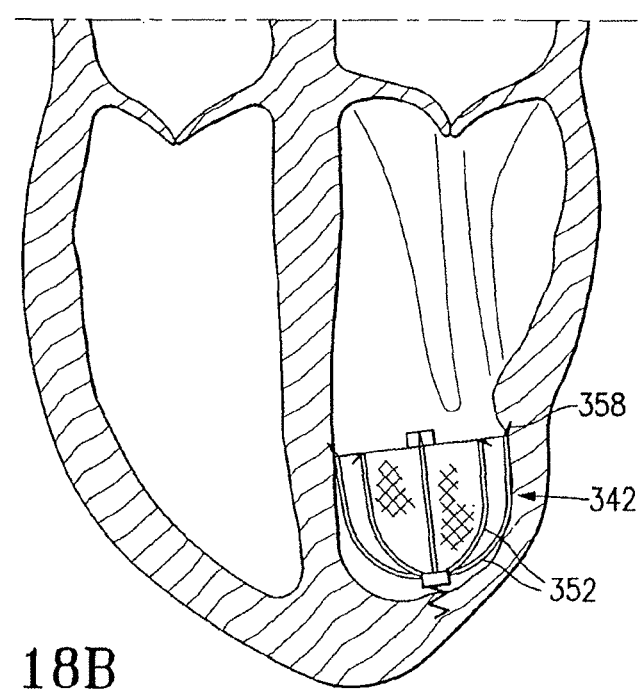
FIG. 18B is a cross-sectional side view of the human heart with the cardiac device of FIG. 18A installed.

FIG. 18B illustrates a human heart with the cardiac device 342 of FIG. 18A having been installed into an akinetic portion thereof. The segments 352 are pressed against the myocardium because the device is slightly oversized.

A further advantage of this embodiment is that because of the size of the device 342 and shape of the segments 352, the passive anchors 358 are assisted in penetrating the myocardium. A further advantage is that because of the shape of the frame 348, the device 342 can be retrieved from the left ventricle as long as the device 34 is still attached to the deployment member 46. A further advantage is that because the entire frame 348 is covered with the membrane 350, the flow of blood to the apex of the akinetic portion is even further blocked.

Figure 19A:
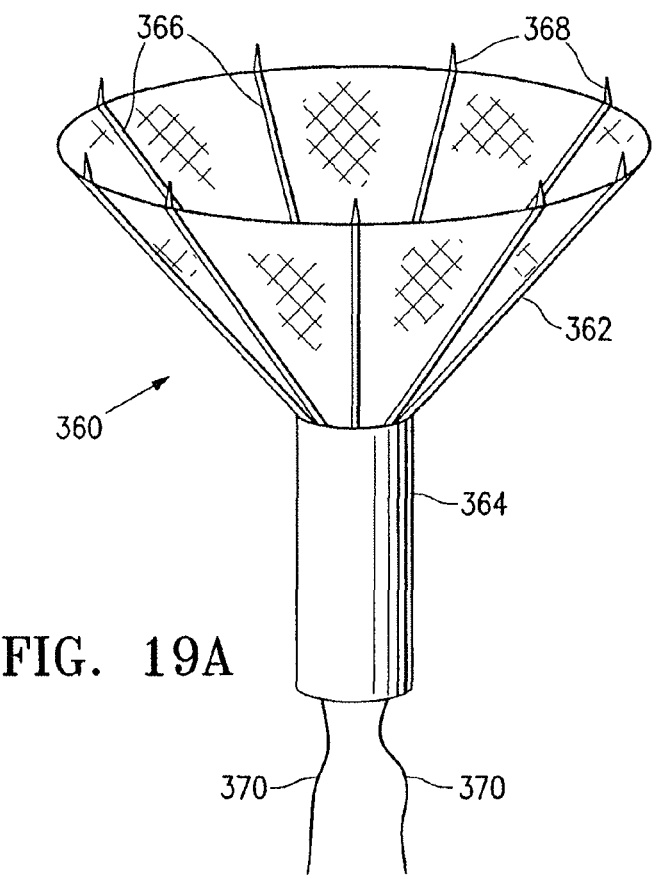
FIG. 19A is a perspective view of a cardiac device according to a further embodiment of the invention.

FIG. 19A illustrates a cardiac device 360 according to a further embodiment of the invention. The cardiac device 360 includes a frame 362 and a stem 364. The frame 362 includes a plurality of segments 366 which extend upwardly and radially from the stem 364 and end in a plurality of sharp passive anchors 368. The stem 364 extends downwards from the frame 362 and includes two suture strands 370 at a distal end thereof.

Figure 19B:
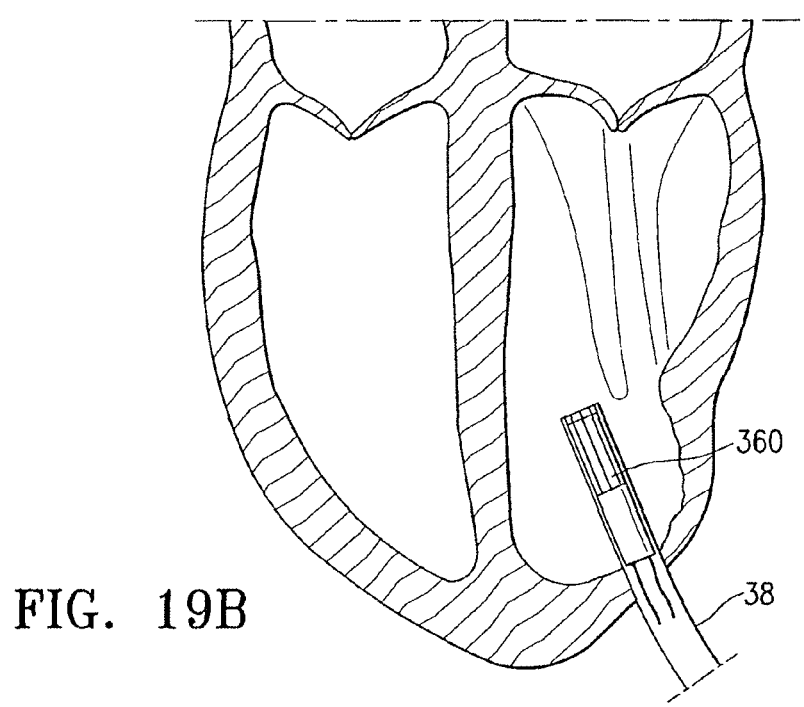
FIG. 19B is a cross-sectional side view of the human heart while the cardiac device of FIG. 19A is being installed.
Figure 19C:
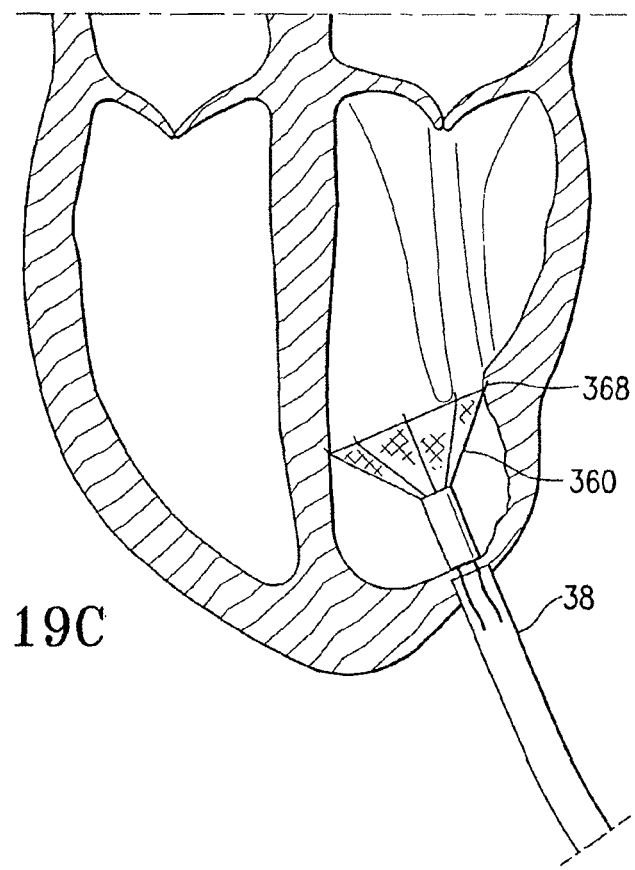
FIG. 19C is a cross-sectional side view of the human heart while the cardiac device of FIG. 19A is being installed.
Figure 19D:
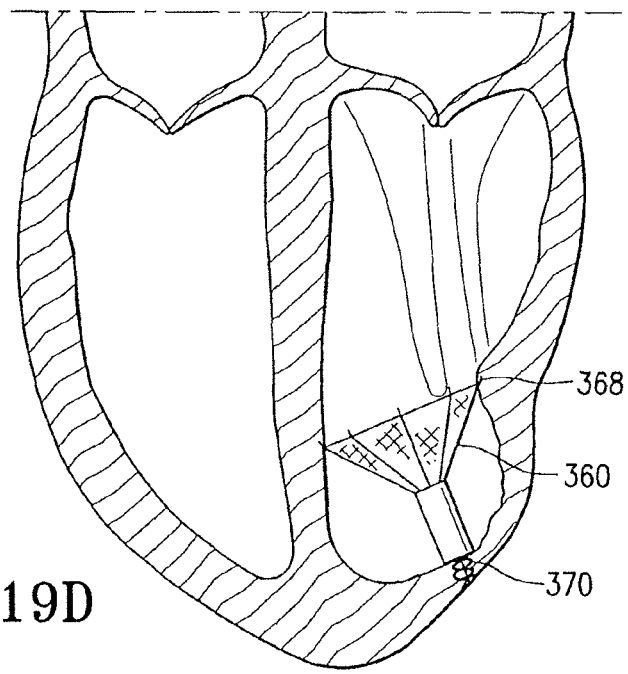
FIG. 19D is a cross-sectional side view of a human heart with the cardiac device of FIG. 19A installed.

FIGS. 19B, 19C, and 19D illustrate the installation of the cardiac device 360 of FIG. 16. While a high pressure is maintained in the left ventricle the catheter tube 38 is inserted through the outer wall into the left ventricle with the cardiac device 360 inserted in the distal end thereof. The catheter 38 is removed from the cardiac device 360, and the cardiac device 360 expands such that the passive anchors 368 are inserted into the inner surface of the left ventricle. The catheter 38 is then completely removed and the sutures 370 are used to close the insertion made by the catheter 38 and to secure the cardiac device 360 to the akinetic portion.

Figure 20A:
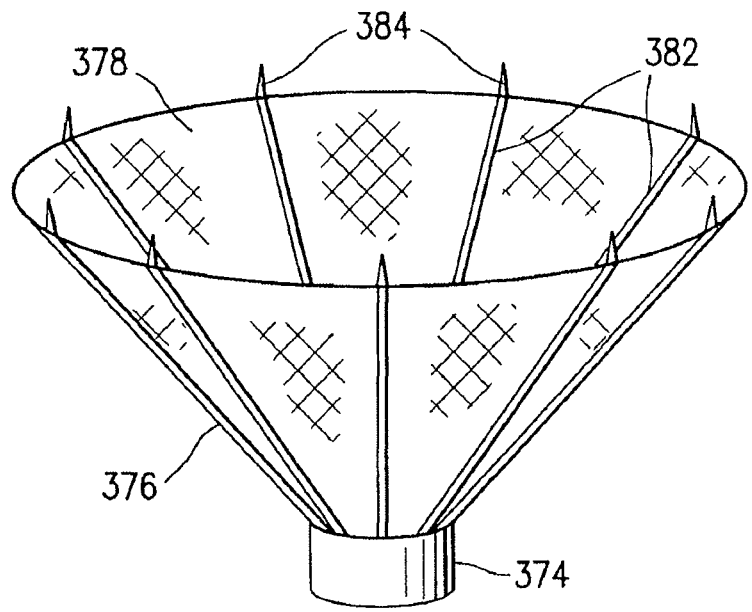
FIG. 20A is a perspective view of a frame of a cardiac device according to another embodiment of the invention.
Figure 20B:
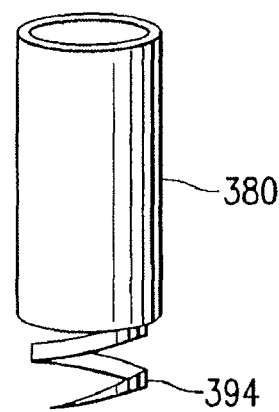
FIG. 20B is a perspective view of a stem of the cardiac device of FIG. 20A.
Figure 20C:
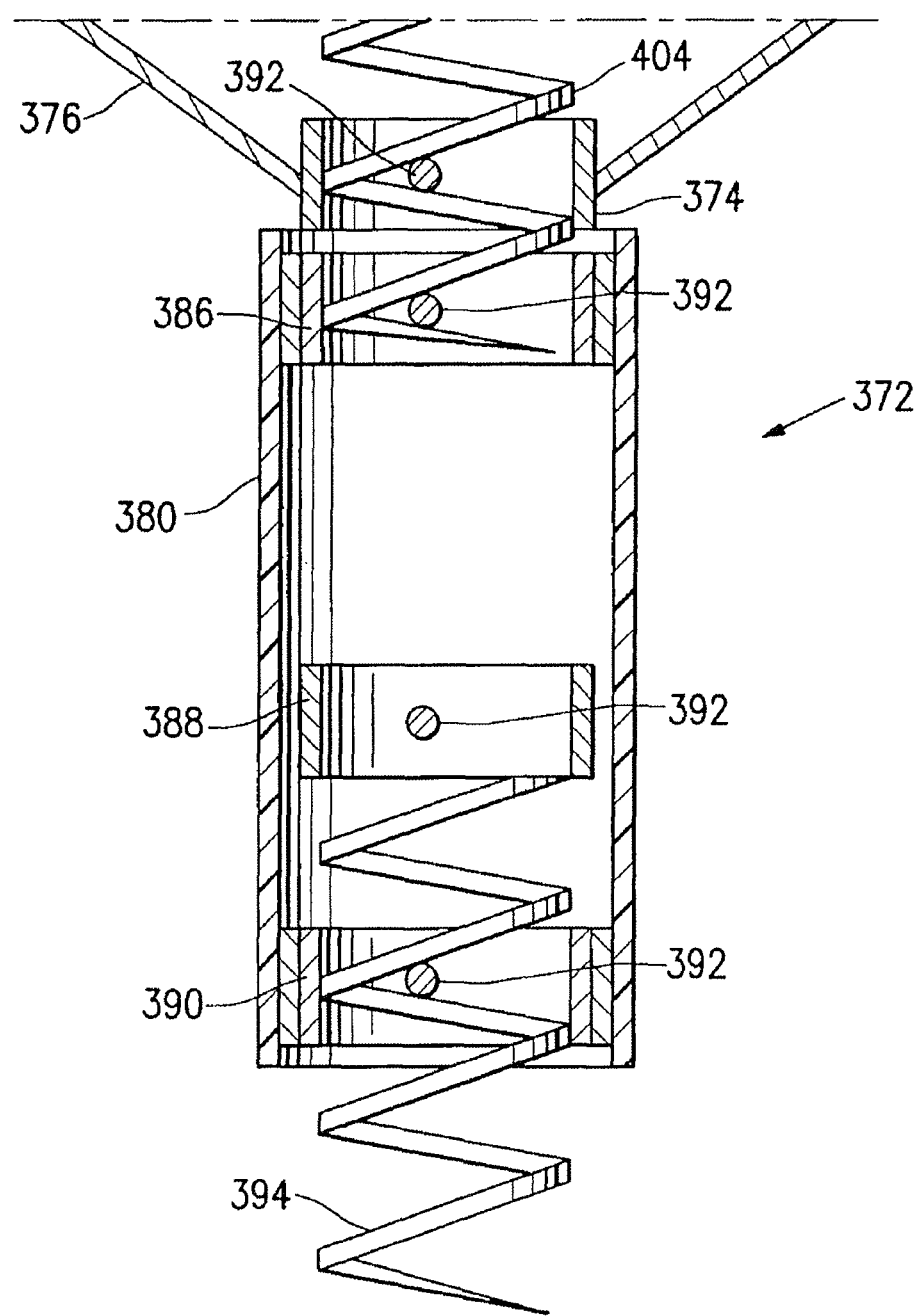
FIG. 20C is a cross-sectional side view of the cardiac device of FIG. 20A and FIG. 20B with the stem attached to the frame.

FIGS. 20A, 20B, and 20C illustrate a cardiac device 372 according to a further embodiment of the invention. The cardiac device 372 includes a frame hub 374, a frame 376, a membrane 378, and a stem 380. The frame hub 374 lies at a central portion of the frame 376. The frame 376 includes a plurality of segments 382 which extend radially and upwardly from the frame hub 374. A sharp passive anchor 384 lies at the end of each of the segments 382. The membrane 378 is stretched between the segments 382 to form a cone-shaped body. Before installation, the stem 380 is unattached to the frame hub 374 and includes a proximal hub 386, an anchor hub 388, and a distal hub 390, each having a pin 392 extending across an inner surface thereof, similar to that of the frame hub 190. The proximal 386 and distal 390 hubs are frictionally held near their respective ends in the stem 380, and the anchor hub 388 is loose within the stem 380 so that it may move. An active anchor 394 extends downwards from the anchor hub 388.

Figure 20D:
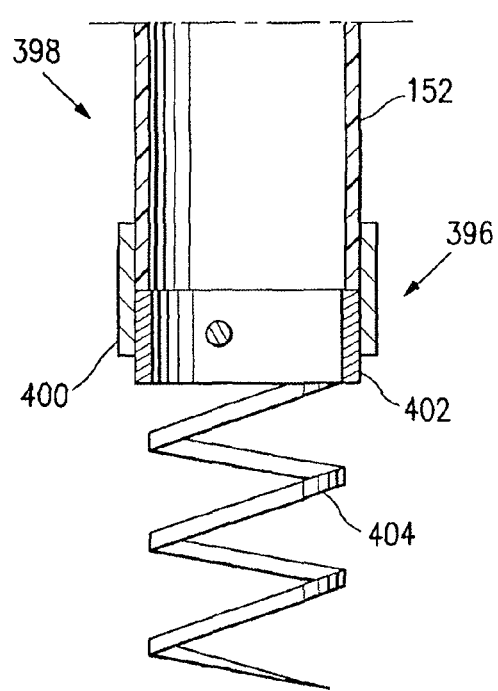
FIG. 20D is a cross-sectional side view of a distal end of a deployment member of a deployment mechanism according to another embodiment of the invention.
Figure 20E:
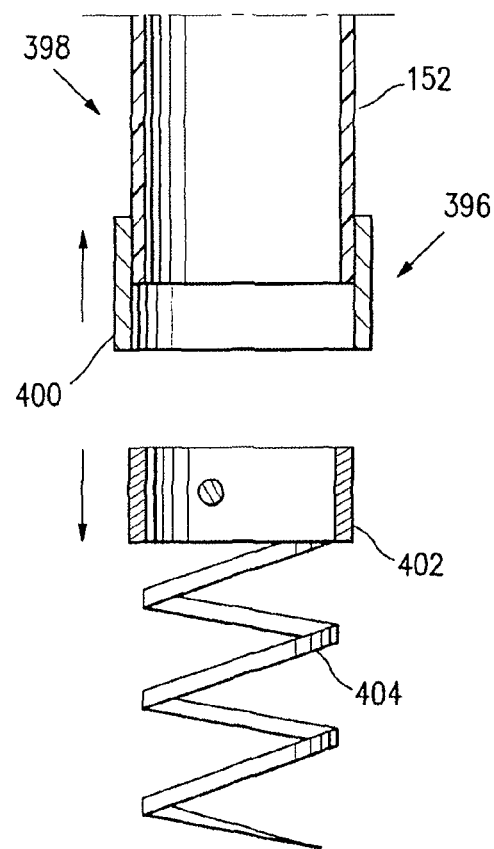
FIG. 20E is a cross-sectional side view of the distal end of the deployment member of a deployment mechanism of FIG. 20D.
Figure 20F:
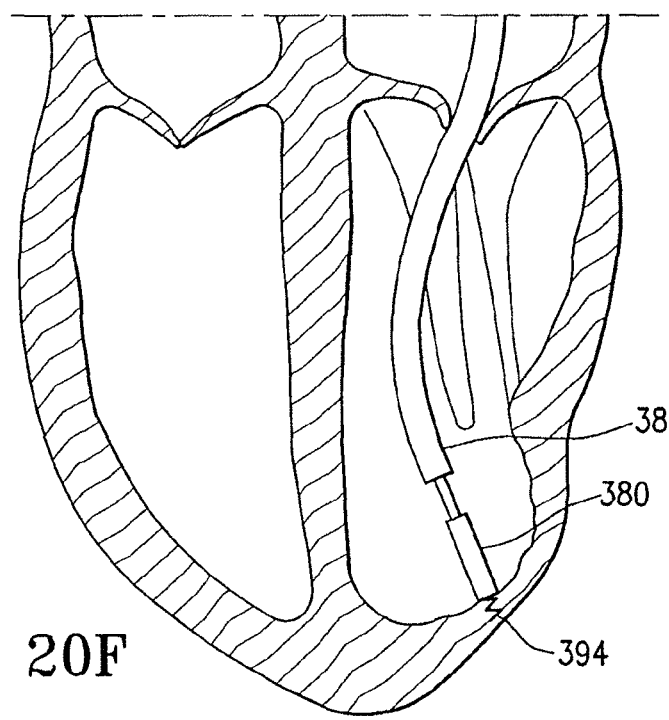
Figure 20G:
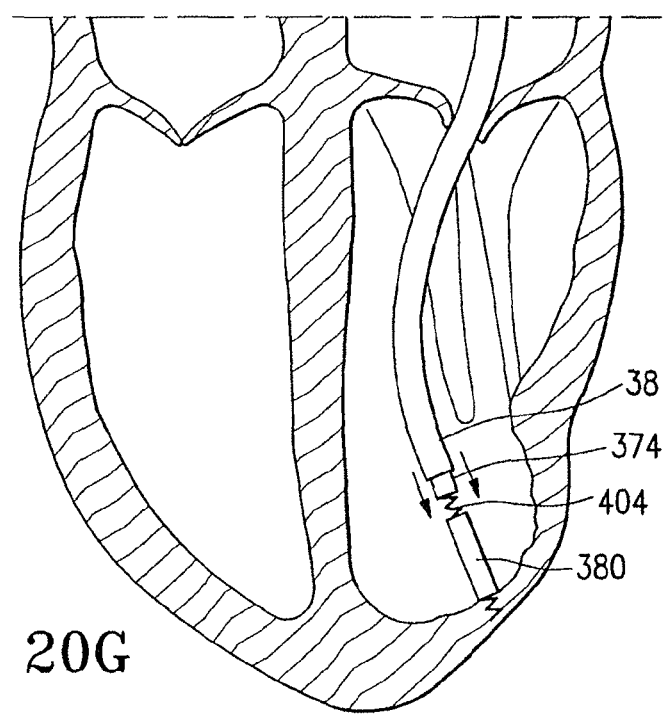
Figure 20H:
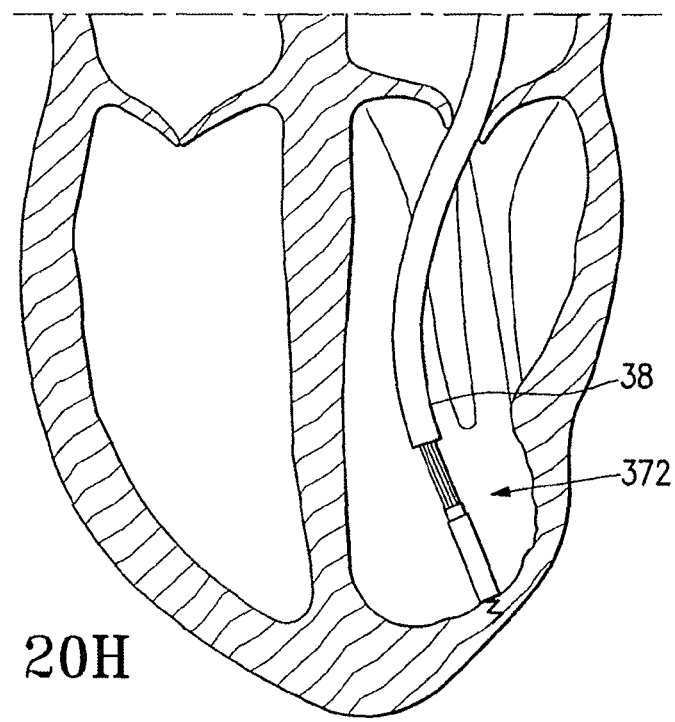

FIGS. 20D and 20E illustrate another embodiment of a distal end 396 of a deployment member 398. The distal end 396 includes a detachment piece 400 and an attachment hub 402. The detachment piece 400 has been added to the distal end of the outer torque shaft 152. The detachment piece 400 is a ring shaped body made of stainless steel with a length of 3 mm and an inner diameter suitable to frictionally hold the attachment hub 402, which is similar to the frame hub 190. An attachment screw 404, similar to the detachment screw 164, extends downwards from the attachment hub 402. Referring specifically to FIG. 20E, forces along the length of the deployment member 398 will, by design, cause the attachment hub 402 to become dislodged from the detachment piece 400.

FIGS. 20E-20H illustrate installation of the cardiac device 372 of FIGS. 20A and 20B into a human heart. In this embodiment, the deployment member used does not include the securing mechanism 166 so that the inner and outer torque shafts may move axially relative to one another.

Before the device 372 and stem 380 are inserted into a heart, the inner torque shaft is passed through the frame hub 374, the proximal hub 386, and the anchor hub 388, and the outer torque shaft is positioned and rotated so that the attachment screw 404 engages both the pins 392 of the frame 374 and proximal 386 hubs, securing the cardiac device 372 to the stem 380. The device 372 and the stem 380 are then retracted into the catheter 38 and steered into a left ventricle. The stem 380 is secured to an apex of an akinetic portion of a left ventricle of the heart by rotating the inner torque shaft, causing the active anchor 394 to penetrate the myocardium. Rotation of the outer torque shaft then causes the attachment screw 404 to disengage the pin 392 of the proximal hub 386, and the device 372 is released from the stem 380. However, the inner torque shaft remains engaged with the hubs in the stem 380.

Figure 20I:
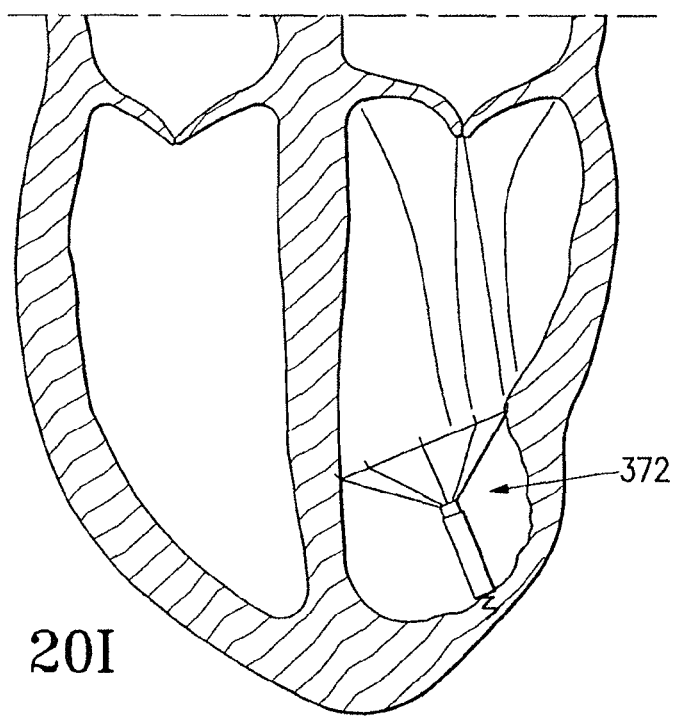

If it is determined that the stem 380 has been properly positioned, the cardiac device 372, secured to the outer torque shaft, is pushed over the inner torque shaft to meet the stem 380. The outer torque shaft is again rotated so that the attachment screw 404 reengages the pin 392 on the proximal hub 386 of the stem, thus re-securing the stem 380 to the frame 376. The deployment member 398 is then forcibly pulled away from the device 372 and the detachment piece 400 releases the attachment screw 404. FIG. 20I illustrates the human heart with the cardiac device 372 of FIGS. 20A and 20B installed.

The invention provides an apparatus for improving cardiac function comprising at least one external actuator, an elongate manipulator connected to the external actuator, a manipulator-side engagement component on a distal end of the elongate manipulator, a collapsible and expandable frame, a frame-side engagement component releasably engageable with the manipulator side-engagement component so that the external actuator can steer the frame when collapsed into a ventricle of a heart where after the frame is expanded, and at least one anchor connected to the frame, movement of the external actuator allowing for (i) insertion of the anchor and (ii) a myocardium ventricle, (iii) subsequent withdrawal of the anchor of the myocardium, (iv) subsequent reinsertion of the anchor into the myocardium, said insertion securing the frame to the myocardium in a selected position, and (v) subsequent disengagement of the manipulator-side engagement component from the frame-side engagement component, said disengagement for releasing the frame from the elongate manipulator.

The frame may have a small cross-dimension when collapsed suitable for being inserted into the ventricle of the heart through a tubular passage in a large cross-dimension when expanded in the ventricle.

The frame may comprise plurality of segments extending from a central portion of the frame.

The frame may be made of nickel titanium or stainless steel.

The apparatus may further comprise a membrane stretched between the segments, the membrane dividing the ventricle into at least two volumes. The membrane may be made of ePTFE. The membrane may be a mesh.

The segments may further comprise first and second portions connected at ends thereof such that the second portions are at an angle to the first portions.

The frame may have proximal and distal sections. The frame may have a diameter of between 10 mm and 100 mm when expanded.

The apparatus may further comprise at least one active anchor and at least one passive anchor. Said insertion of the passive anchor may be in a first direction and said withdrawal of the passive anchor may be in a second direction, the second direction being substantially 180 degrees from the first direction.

The apparatus may further comprise a first passive anchor extending in the first direction and a second passive anchor extending in a third direction. The active and passive anchors may have sharp ends that penetrate the myocardium.

The apparatus may further comprise a tubular passage with a distal end suitable to be inserted into the ventricle.

The elongate manipulator may further comprise a frame member with proximal and distal ends and an anchor member with proximal and distal ends, the frame and anchor members being moveable through the tubular passage.

The manipulator side-engagement component may further comprise a frame formation on the distal end of the frame member and an anchoring formation on the distal end of the anchor member The apparatus may further comprise an external frame actuator connected to the proximal end of the frame member and an external anchor actuator connected to the proximal end of the anchor member.

When the distal end of the elongate manipulator is in the selected position, a first movement of the external anchor actuator may cause the active anchor to be inserted into the myocardium to secure the frame to the myocardium and a second movement of the external anchor actuator may cause the active anchor to withdraw from the myocardium, said withdrawal releasing the frame from the myocardium.

A first movement of the external frame actuator may cause the frame formation to engage the frame-side engagement component, said engagement securing the frame to the distal end of the elongate manipulator and a second movement of the external frame actuator may cause the frame formation to disengage the frame-side engagement component, said disengagement releasing the frame from the elongate manipulator.

The frame may be shaped such that entry of the proximal section of the frame into the tubular passage causes the frame to partially collapse such that the passive anchor withdraws from the myocardium in the second direction and entry of the distal section of the frame into the tubular passage causes the frame to collapse to the small cross-section so that the distal end of the elongate manipulator and the frame can be removed from the heart.

The elongate manipulator and the frame may be insertable into the heart simultaneously and the frame may be shaped such that exposure of the distal section of the frame from the distal end of the tubular passage allows the frame to partially expand and exposure of the proximal section of the frame from the distal end of the tubular passage allows the frame to expand to a large cross-section, said expansion causing the passive anchors to penetrate the myocardium to secure the frame to the myocardium.

The invention also provides an apparatus for improving cardiac function comprising a frame which includes a plurality of central segments surrounding a central axis, the central segments having first and second ends, the first ends being pivotally connected to one another, and a plurality of outer segments having first and second ends, the first ends being pivotally secured to the second ends of the central segments, a membrane secured to the frame such that movement of the second ends of the central segments away from the central axis causes the membrane to unfold, the unfolding of the membrane causing the outer segments to pivot relative to the respective central segments away from the central axis and movement of the second ends of the central segments toward the central axis causes the membrane to fold, the folding of the membrane causing the outer segments to pivot relative to their respective central segments toward the central axis, and an anchor connected to the frame, the anchor being insertable into a myocardium of a heart to secure the cardiac device to the myocardium in a ventricle of the heart.

The frame may include at least three central segments and at least three outer segments.

The membrane may be stretched between the central and the outer segments

The anchor may be secured directly to the frame.

The invention further provides an apparatus for improving cardiac function comprising a frame, a membrane, having an inner surface, secured to the frame, the membrane and the frame jointly forming a cardiac device being moveable between a collapsed and an expanded state, in a collapsed state at least a portion of the inner surface of the membrane facing a vertical axis of the cardiac device and the cardiac device being insertable into a ventricle of a heart, in the expanded state the portion of the inner surface of the membrane facing away from the vertical axis and being in contact with a myocardium and the cardiac device being in a selected position in the ventricle, and an anchor connected to the cardiac device, the anchor being insertable into the myocardium of the heart to secure the cardiac device to the myocardium in the selected position in the ventricle.

The cardiac device may collapse toward the vertical axis and expand away from the vertical axis.

The membrane may fold towards the vertical axis when the cardiac device collapses and may unfold away from the vertical axis when the cardiac device expands.

The frame may be at least one of nickel titanium and stainless steel.

The membrane may be made of ePTFE.

The anchor may have a sharp end.

The invention further provides an apparatus for improving cardiac function comprising a frame being expandable in a selected position to a pre-set shape in a ventricle of a heart, a formation on the frame, and an anchoring device having an anchor, the anchoring device being engaged with and rotatable relative the formation to rotate the anchor relative to the frame, said rotation causing the anchor to be inserted into a myocardium of the heart, said insertion securing the frame in the selected position in the ventricle.

The anchoring device may engage the formation such that a first rotation of the anchoring device causes the anchor to move away from the frame and a second rotation of the anchoring device causes the anchor to move toward the frame.

The formation may be a pin, and the anchor may be a screw.

The invention further provides an apparatus for improving cardiac function comprising at least a primary expandable frame being in a selected position in a ventricle of a heart when expanded, an anchor connected to the frame, the anchor being insertable into a myocardium of the heart to secure the primary frame within the ventricle, a frame-side engagement component connected to the primary frame, a membrane, and a membrane-side engagement component being engageable with the frame-side engagement component, said engagement securing the membrane to the frame.

The apparatus may further comprise a secondary expandable frame being in a selected position in the ventricle of the heart when expanded, the secondary frame being secured to the membrane and connected to the membrane-side engagement component thereby interconnecting the membrane to the membrane-side engagement component.

The anchor may be connected to the at least one frame.

The frame-side engagement component may be connected to the primary frame at a central portion of the primary frame.

The membrane-side engagement component may be connected to the secondary frame at a central portion of the secondary frame.

The apparatus may further comprise an active anchor being connected to the frame-side engagement component such that a first m. movement of the frame-side engagement component causes the active anchor to enter the myocardium and a second movement of the frame-side engagement component causes the active anchor to withdraw from the myocardium.

The apparatus may further comprise a passive anchor being connected to at least one of the frames such that the passive anchor enters the myocardium when the frame expands.

The invention further provides an apparatus for improving cardiac function comprising a flexible liner, a membrane secured to the liner, the membrane and the liner jointly forming a cardiac device being moveable between a collapsed and an expanded state, in the collapsed state the cardiac device being insertable into a ventricle of a heart. In the expanded state the cardiac device being in a selected position in the ventricle, the liner covering a wall in the ventricle and the membrane separating the ventricle into two volumes, and an anchor connected to the cardiac device, the anchor being insertable into a myocardium of the heart to secure the cardiac device to the myocardium in the selected position in the ventricle.

The flexible liner may comprise a plurality of lengths of strands being connected at endpoints thereof.

The apparatus may further comprise a frame secured to the cardiac device and connected to the anchor thereby interconnecting the cardiac device and the anchor.

The apparatus may further comprise a frame-side engagement component being connected to the cardiac device and an active anchor being connected to the frame-side engagement component such that a first movement of the frame-side engagement component causes the active anchor to enter the myocardium and a second movement of the frame-side engagement component causes the active anchor to withdraw from the myocardium.

The apparatus may further comprise a passive anchor being connected to the cardiac device such that the passive anchor enters the myocardium when the cardiac device expands.

The invention further provides an apparatus for improving cardiac function comprising an expandable frame being in a selected position in a ventricle of the heart and having an outer edge when expanded, the outer edge defining a non-planar cross-section of an inner wall of a ventricle and an anchor connected to the frame, the anchor being insertable into the myocardium of the heart to secure the frame to the myocardium in the selected position in the ventricle.

The apparatus may further comprise a membrane being secured to a frame, the membrane separating the ventricle into two volumes.

The frame may have a vertical axis and the outer edge may have a diameter, the diameter intersecting the vertical axis at an angle other than 90 degrees.

The invention further provides an apparatus for improving cardiac function comprising an anchor being insertable into a myocardium of a heart to secure the anchor to the myocardium within a ventricle of the heart, an anchor-side engagement component being secured to the anchor, an expandable frame being in a selected position in the ventricle when expanded, and a frame-side engagement component being secured to the frame, the frame-side engagement component being engageable with the anchor-side engagement component, said engagement securing the frame to the anchor in the selected position in the ventricle.

The apparatus may further comprise a membrane being secured to the frame.

A first movement of the anchor-side engagement component may cause the anchor to enter a myocardium and a second movement of the anchor-side engagement component may cause the anchor to withdraw from the myocardium.

A first movement of the frame-side engagement component may cause the frame-side engagement component to engage the anchor-side engagement component and a second movement of the frame-side engagement component may cause the frame-side engagement component to disengage the anchor-side engagement component.

Said engagement may release the frame from the anchor.

The invention further provides an apparatus for improving cardiac function comprising a flexible body, a membrane connected to the flexible body, the membrane and flexible body jointly forming a cardiac device being movable between a collapsed and an expanded state, in the collapsed state the cardiac device being insertable into a ventricle of the heart, in the expanded state the cardiac device being in a selected position in the ventricle, and an anchor connected to the cardiac device, the anchor being insertable into the myocardium of the heart to secure the cardiac device to the myocardium in the selected position of the ventricle.

The apparatus may further comprise a frame having a distal end, the membrane may be secured to the frame, and the body may have proximal and distal ends, the proximal end of the body being secured to the distal end of the frame, and the distal end of the body being connected to the anchor.

The body may be cylindrical with a diameter of between 0.5 mm and 6 mm and a height of between 1 mm and 100 mm.

The cardiac device may have a vertical axis.

The body may have a proximal opening at the proximal end, a distal opening at the distal end, and a passageway there through connecting the proximal and distal openings.

The body may be able to bend between 0 and 120 degrees from the vertical axis.

The invention further provides a device for improving cardiac function comprising a collapsible and expandable frame having first and second portions, the frame being insertable into a ventricle of a heart when collapsed, when expanded the frame being in a selected position in the ventricle and the second portion of the frame covering a wall in the ventricle, a membrane secured to the frame such that the membrane divides the ventricle into at least two volumes when the frame is expanded, the frame and the membrane jointly forming a cardiac device, and an anchor connected to the cardiac device, the anchor being insertable into a myocardium of the heart to secure the cardiac device in the selected position in the ventricle.

The frame may further comprise a plurality of segments, each segment having an inner and outer portion being connected at ends thereof, the outer portions being at an angle to the inner portions.

The membrane may be secured to the inner and outer portions of the segments.

The device may further comprise a plurality of anchors being connected to at least one segment such that when the frame expands the anchors enter the myocardium in a first direction, and when the frame collapses the anchors withdraw from the myocardium in a second direction approximately 180 degrees from the first direction.

The invention further provides a system for improving cardiac function comprising a collapsible and expandable frame, when collapsed the frame being insertable into a selected position in a ventricle of the heart through an opening in the heart having a small cross-dimension, when expanded in the selected position, the frame having a large cross-dimension, and an anchor connected to the frame, being insertable into a myocardium of the heart to secure the frame to the myocardium in the selected position.

The opening may be an incision in the myocardium.

The anchor may further comprise a plurality of strands woven through the myocardium such that the opening is closed.

The invention further provides a system for improving cardiac function comprising an external actuator, an elongate manipulator having a tube suitable to be inserted into a ventricle of a heart to a selected position and a deployment member positioned therein slidable between a first and second position, the deployment member having proximal and distal ends, the distal end being within the tube when the deployment member is in the first position and out of the tube when the deployment member is in the second position, the deployment member being connected to the external actuator at the proximal end thereof, a deployment-side engagement component on the distal end of the deployment member, a frame-side engagement component being engageable with the deployment-side engagement component, said engagement securing the deployment-side engagement component to the frame-side engagement component such that a movement of the external actuator causes the engagement components to disengage, said disengagement releasing the deployment-side engagement component from the frame-side engagement component, a frame being connected to the frame-side engagement component, the frame being moveable between a collapsed and an expanded state, the frame being connected to the deployment member in the collapsed state with a small cross-dimension when the deployment member is in the first position and the frame is within the tube, the frame being shaped such that when the deployment member is moved to the second position and the frame exits the tube, the frame expands to the expanded state with a large cross-dimension and when the deployment member is moved back to the first position, the frame collapses to the collapsed state as the frame enters the tube, and an anchor connected to the frame being insertable into a myocardium of the heart to secure the frame to the myocardium of the heart, such that the deployment mechanism can be removed from the heart, the anchor entering the myocardium in a first direction when the frame expands and withdrawing from the myocardium in a second direction when the frame collapses, said withdrawal releasing the frame from the myocardium The external manipulator may further comprise an anchor deployment knob and a detachment knob.

The deployment member may further comprise an anchor shaft having proximal and distal ends and a detachment shaft having proximal and distal ends, the proximal end of the anchor shaft being connected to the anchor deployment knob, the proximal end of the detachment shaft being connected to the detachment knob.

The deployment-side engagement component may further comprise a deployment-side anchor formation connected to the distal end of the anchor shaft and a deployment-side detachment formation connected to the distal end of the detachment shaft.

The frame-side engagement component may further comprise a frame-side anchor formation being connected to the anchor and a frame-side detachment formation on the frame, the frame-side anchor formation being engageable with the deployment-side anchor formation, the frame-side detachment formation being engageable with the deployment-side detachment formation, a first movement of the detachment knob causing the deployment-side detachment formation to engage the frame-side detachment formation, said engagement securing the frame to the deployment member, a first movement of the anchor deployment knob causing the anchor to enter the myocardium and a second movement of the anchor deployment knob causing the anchor to withdraw from the myocardium, a second movement of the detachment knob causing the deployment-side detachment formation to disengage the frame-side detachment formation, said disengagement releasing the frame from the deployment member.

The anchor shaft and the detachment shaft may be coaxial.

The anchor shaft may be an inner torque shaft and the detachment shaft may be an outer torque shaft.

The present invention is directed to devices and methods for the treatment of a patient's organ such as a heart. In some cases the heart is susceptible to or experiencing diastolic dysfunction, mitral valve regurgitation or heart failure.

Diastole is the phase of cardiac cycle during which relaxation of the heart muscles occurs after ejecting blood into general circulation and is governed by active and passive properties of the myocardium, geometrical characteristics of the chamber and external forces.

In the cardiac cycle left ventricular diastolic filling begins with opening of the mitral valve as pressure in the ventricle falls below pressure in the atrium. As the ventricle begins to contract the pressure in the ventricle soon exceeds that of the atrium and the mitral valve closes, which marks the end of diastole. The ventricular pressure and volume at this point are referred to as end-diastolic pressure ("EDP") and end-diastolic volume ("EDV"), and the beginning of ventricular systole.

The rate and amount of left ventricular diastolic filling depends upon the positive pressure upstream of the left ventricle provided by venous return and decreasing pressure provided within the left ventricle by expansion of the ventricle during diastole. A reduction in ventricular compliance (i.e., increase in stiffness of ventricular heart wall) may result in less diastolic expansion of the ventricle, less ventricular filling (i.e. decreased end-diastolic volume EDV) and a greater diastolic pressure, resulting in a change in the ventricular diastolic pressure-volume characteristics. In a case of ventricular enlargement and/or the decrease of myocardial function, the left ventricular elastic recoil forces may be diminished, therefore leading to increase of the ventricular filling pressure.

Diastolic dysfunction may also be caused by changes in the rate and degree of left ventricular relaxation, which as stated above, in part is an active process. Several factors can affect left ventricular relaxation, including inotropic stimulation, fast heart rates, non-uniform heart activation and altered timing of all the forces that oppose ventricular ejection. Since calcium uptake by the sarcoplasmic reticulum is energy-dependent, any process that decreases the availability of high-energy phosphates, such as ischemia or hypoxia, also impairs myocardial relaxation.

Diastolic dysfunction is established, for example, by measurements of various echocardiographic parameters such as decreased peak filling velocity and prolonged relaxation time, signs of increased filling pressure and clinical symptoms of dyspnea and peripheral edema.

The devices and methods herein can be used to treat a patient's heart suffering from a diastolic dysfunction disorder or a condition exhibiting the characteristics of diastolic dysfunction. The devices and methods herein involve implanting within the ventricle a device whose shape elastically distorts during systole and recoils during diastole to augment the ventricle's natural recoil action. In one embodiment, the device also partitions the patient's ventricle into a functional portion and an excluded, non-functional portion. The method may be used to treat a heart, in particular the left ventricle, which is exhibiting signs of diastolic dysfunction. Diastolic dysfunction may evidence itself by portions of the chamber becoming dilated, dyskinetic or akinetic, depending on the particular pathology inducing damage to the heart.

A. Device

Figure 21:
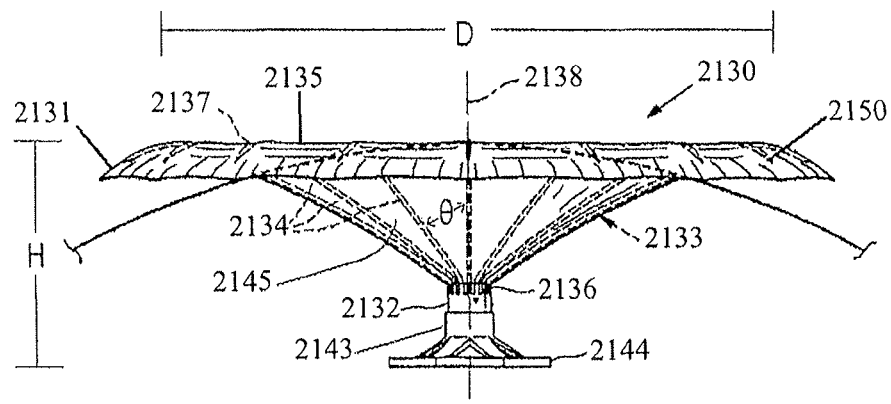
FIG. 21 is an elevational view of a partitioning device embodying features of the invention in an expanded configuration.

FIG. 21 illustrates a diastolic recoil device 2130 which embodies features of the invention and which may be utilized in practicing the methods herein. The device 2130 includes hub 2132, preferably centrally located on the diastolic recoil device, and a radially expandable reinforcing frame 2133 formed of a plurality of ribs 2134 connected at their distal end to the hub. Alternative embodiments of the devices herein include at least three ribs. The ribs form an elastic frame and can be made of material such as, for example, Nitinol stainless steel, titanium alloys, NiTi alloy, other metal alloys, or plastic composites. In some cases, the ribs/frame are made of a material which allows for compression of the free proximal ends towards the central axis during delivery and self expansion upon deployment (e.g. in the patient's heart). The ribs 2134 have distal ends 2136 which may be pivotally mounted to the hub 2132 and biased outwardly or fixed to the hub, and free proximal ends 2137 which are configured to curve or flare away from a center line axis 2138 at least upon expansion of the diastolic recoil device.

Proximal ends 2137 of ribs 2134 in their expanded configuration angle outwardly from the hub at an angle 0 of about 20-90° away from a centerline axis 2138 of the device. The free proximal ends 2137 curve outwardly so that the membrane when secured to the ribs of the expanded frame forms a trumpet-shaped concave pressure receiving surface.

Proximal ends 2137 of ribs 2134 can include anchors 2150 configured to engage, and preferably penetrate into, the target tissue (e.g. endocardium of heart chamber to be partitioned, i.e. a ventricle). This enables the securing of a peripheral edge of the diastolic recoil device to the heart wall and fixation of the diastolic recoil device within the chamber so as to partition the chamber into two portions. Anchors 2150 are configured to penetrate the tissue lining at an angle ranging from 30-120 degrees to the centerline axis 2138 of the partitioning device. Anchors 2150 can include barbs, hooks and the like which prevent undesired withdrawal of device 2130 from the target tissue.

A membrane 2131 can be attached to the ribs 2134 of the frame. Membrane 2131 can be made of a porous material, for example, expanded polytetrafluoroethylene (ePTFE, or GORE-TEX®, one commercially available product) or a non-porous material. When membrane 2131 is porous, it facilitates tissue ingrowth after deployment in the non-functional portion of the heart chamber. Membrane 2131 can also be formed from other mesh materials including metals, alloys, or composites. In some cases Membrane 2131 is formed from a biocompatible polymeric material such as nylon, polyethylene terephthalate (PET) or polyesters such as hytrel. While not shown in detail, the membrane 2131 has a first layer secured to the concave face of the frame formed by the ribs 2134, which creates a pressure receiving surface 2135. When the diastolic recoil device 2130 is deployed upon implantation, the pressure receiving surface 2135 is presented to the functional portion of the partitioned chamber. The membrane 2131 may have a second layer secured to the convex face of the frame formed by the ribs 2134, creating a non-pressure receiving surface 2145. When the diastolic recoil device 2130 is deployed, the non-pressure receiving surface 2145 is presented to the non-functional portion of the partitioned chamber. The manner of application of the layers of membrane to the ribs is described in co-pending application Ser. No. 10/913,608, filed on Aug. 5, 2004, entitled "Ventricular Partitioning Device", assigned to the assignee of the present invention, and incorporated herein by reference in its entirety.

The hub 2132 shown in FIG. 21 preferably has a distally extending stem 2143 with a non-traumatic support component 2144. The distally extending stem 2143 with non-traumatic support component 2144 together may extend a variable distance from the base of the hub 2132, in order to space the device a selected distance from the wall of the chamber where the device is to be seated, thus permitting variable partitioning of the volume of the chamber. The stem 2143 and support component 2144 together may extend from about 3 mm to about 15 mm from the central hub 2132 to isolate differing proportions of the chamber or to provide suitable fits for differing size hearts.

Diastolic recoil devices according to the present invention have several distinct configurations. The unconstrained configuration is measured prior to any constriction or installation within a patient, and represents the largest diameter possible. For example, the diameter (D) as shown in FIG. 21 of a device in its unconstrained configuration is at least 35 mm, up to about 100 mm, and its height (H) is at least 10 mm, to about 60 mm, as needed to fit within the heart of a patient as more fully discussed below. When in its collapsed configuration, a diastolic recoil device has a diameter of less than 12 mm, such that it fits in a catheter for endovascular delivery. Once a diastolic recoil device has been implanted into a chamber of the heart, the flexible and resilient nature of the frame yields two further configurations. The largest installed configuration occurs at the end of diastole, and is referred to as End Diastole Diameter (EDD). The smallest installed configuration occurs at the end of systole, when the chamber is compressed to its smallest size, and this diameter is referred to as the End Systole Diameter (ESD).

Prior to the implantation procedure (as described further below), the diastolic recoil device implant is matched to the size of the left ventricle (e.g., the chamber into which it will be implanted) by comparing the left ventricle end-diastolic diameter at the level of the base of the papillary muscles ("landing zone" diameter) to the unconstrained diastolic recoil device diameter. In order to maximize the occurrence of a permanent seal between the implant and the endocardium, the unconstrained diameter of the selected diastolic recoil device is oversized as compared to the diameter of the landing zone.

Implantation of the oversized diastolic recoil device results in storing compressive forces in the elastic NiTi frame of the device. The origin of compressive forces is a bending deformation of the resilient frame ribs. The decrease of the unconstrained frame diameter to the landing zone diameter is associated with a radial tip displacement of each frame rib while the opposite end of the rib is fixed to the hub of the frame, therefore causing a flexing deformation of the ribs and a rebounding force attempting to return the frame to the unconstrained diameter. These outward recoil forces are transmitted to the myocardium via proximal ends of the ribs implanted into the myocardium, thus applying pressure against the wall of the ventricle. In some embodiments, the unconstrained diameter of the diastolic recoil device is selected to be oversized by at least about 10% up to about 60% over the diameter of the landing zone. The diastolic recoil device is elastic and its configuration changes from a small diameter at end-systole (ESD) to a larger diameter (EDD) at end-diastole. The compression of the diastolic recoil device from end-diastolic to end-systolic configuration causes additional compressive forces to be stored in the elastic frame of the device and is preferably designed to be substantially equivalent at end systole to the elastic restoring forces that originate in the myocardium in a healthy heart. Thus the amounts of outward recoil forces that are transmitted to the walls of the ventricle during diastolic filling are enhanced and augment outward motion of the ventricular walls. The expansion of the ventricle is assisted by the expansion of the ribs to improve diastolic function of the ventricle. Resultantly, stress is decreased in the myocardium, which is beneficial for more efficient mechanical function. As stress is a major cause of dilation, implantation of a device and its contribution of recoil forces back to the heart wall may limit remodeling in the ventricle.

Figure 22:
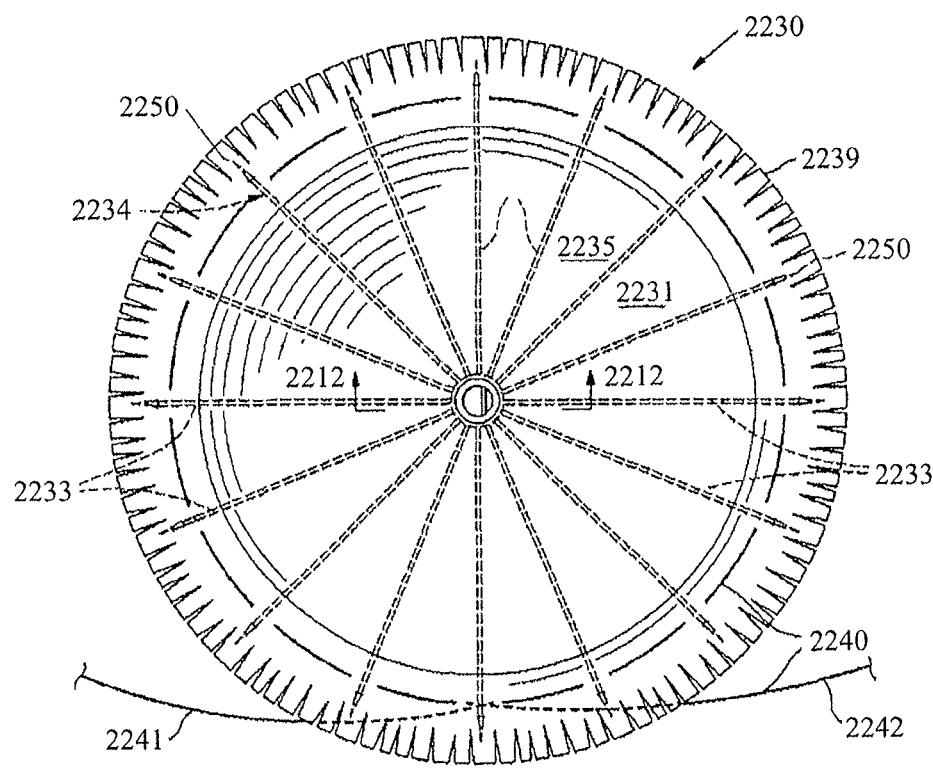
FIG. 22 is a plan view of the diastolic recoil device shown in FIG. 21 illustrating the upper surface of the device.

FIG. 22 illustrates a top view of a diastolic recoil device 2230 in its unconstrained configuration, as viewed from above the pressure receiving surface 2235. The diastolic recoil device 2230 of FIG. 22 has ribs 2234 which are radially expandable and connected at their distal end to a central hub. The ribs are adapted to provide an elastic recoil force to a wall of a chamber of a heart (e.g. a left or right ventricle). The ribs store energy during systole and release the stored energy back to the wall of the chamber of the heart in synchrony with the heart cycle. The device 2230 further comprises a membrane 2231 coupled to the radially expandable ribs 2234. At least part of membrane 2231 is secured to a pressure receiving side of the frame 2233, creating the pressure receiving surface 2235. Radial expansion of the free proximal ends 2237 unfurls the membrane 2231 secured to the frame 2233 so that the membrane presents the pressure receiving surface 2235 which defines the functional and nonfunctional portions of the chamber. A peripheral edge 2239 of the membrane 2231 may be serrated as shown in FIG. 22. A serrated edge of peripheral edge 2239 in this embodiment helps the membrane spread flat at the periphery. Anchors 2250 can include barbs, hooks and the like which prevent undesired withdrawal of device 2130 from the wall of the chamber of heart after implantation of the device 2230.

The ribs 2234 may be individually of variable length and the membrane 2231 may be of variable shape suitable to practice the present invention. In some embodiments the membrane 2231 and frame 2233 define a circular periphery and in other embodiments the membrane 2231 and frame 2233 define an eccentric or elliptical periphery.

In one embodiment, a strand 2240 extends around essentially the entire periphery of the membrane so that the flexible periphery of the membrane between each pair of ribs 2234 is effectively sealed against the heart wall. The effectiveness of the seal contributes to facile endothelialization of the pressure receiving surface of a porous membrane. Once endothelialized, the membrane supports regrowth of a new inner wall of the chamber. The expansive strand 2240 is formed from material which is stiffer than the flexible, unsupported material of the membrane to provide an outward expansive force or thrust to prevent formation of undesirable inwardly directed folds or wrinkles when the ribs of the diastolic recoil device are in a contracted configuration. A suitable strand 2240 is formed from materials such as polypropylene suture or super-elastic NiTi alloy wires. Such strands are typically about 0.005 to about 0.03 inch (about 0.13 to about 0.76 mm) in diameter to provide the requisite outward expansive force when placed in a circular position such as around the periphery of the membrane in less than completely expanded configuration. Ends 2241 and 2242 of the expansive strand 2240 are shown extending away from the diastolic recoil device in FIG. 22. The ends 2241 and 2242 may be left unattached or may be secured together, e.g. by a suitable adhesive, or to the membrane 2231 itself. When the diastolic recoil device is in the collapsed configuration for delivery, the outwardly biased strand 2240 ensures that there are no inwardly directed folds or wrinkles and that none are formed when the device is expanded for deployment within the heart chamber. The strand 2240 may be several strands of materials as above, rather than just one.

Figure 23:
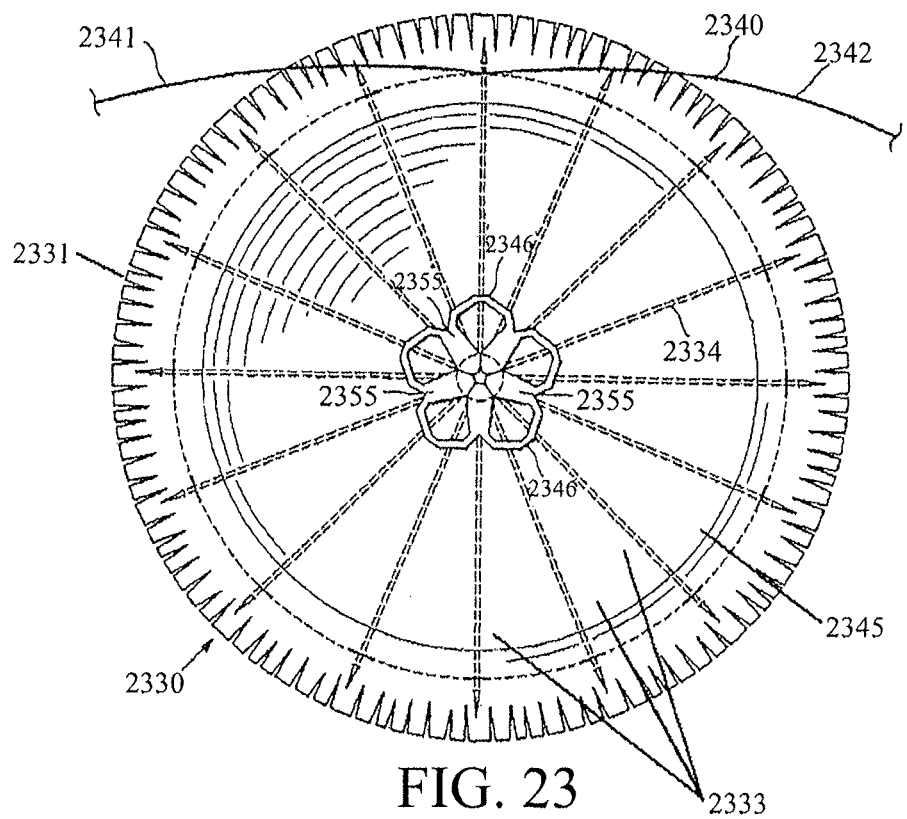
FIG. 23 is a bottom view of a diastolic recoil device.

FIG. 23 is a bottom view of a device 2330 herein. The nonpressure receiving surface 2345 of the membrane 2331 which is secured to the ribs 2334 (dotted lines) are illustrated in this view. Extending from the base of the frame 2333 are feet 2355 which support the device within the non-functional portion of the chamber being partitioned against a wall therein. Feet 2355 extend radially and preferably are interconnected by lateral supports 2346 which help distribute the force over an expanded area of the surface of the chamber. Feet 2355 and lateral supports 2346 are made of resilient material which can support the device without causing trauma to the wall of the chamber at contact points. This minimizes or avoids immediate or long term damage to the tissue of the heart wall. The diastolic recoil device can be used to support weakened tissue of damaged heart wall such as necrotic tissue caused by myocardial infarction (MI) and the like.

Figure 24:
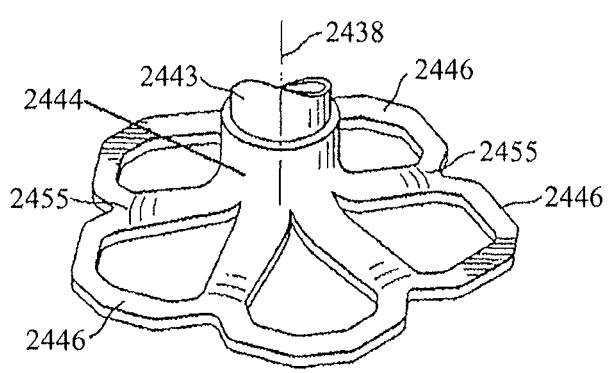
FIG. 24 is a perspective view of one embodiment of a non-traumatic tip of the distally extending stem of a diastolic recoil device.
Figure 25:
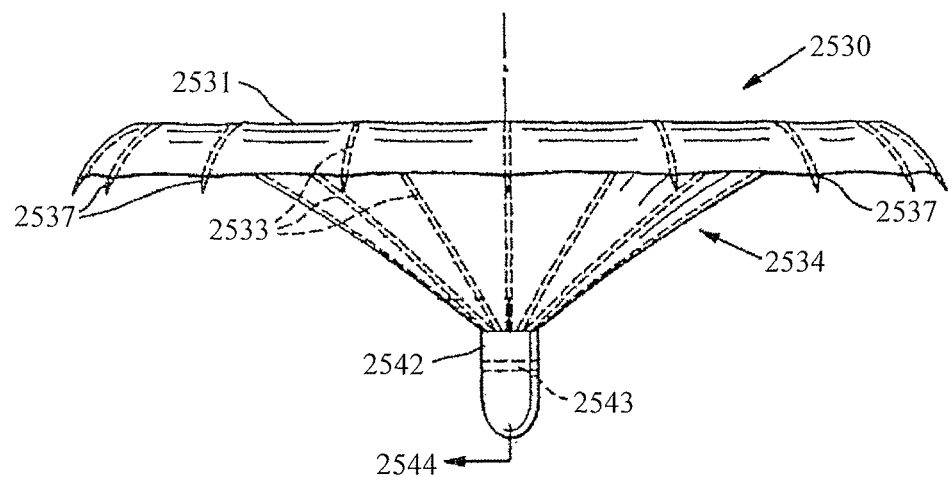
FIG. 25 is an elevational view of a diastolic recoil device embodying an alternative support component of the invention in an expanded configuration.

FIG. 24 is a side view of the support component of the device. The support component 2444 has a plurality of feet 2455, e.g., at least three or any variable number. The support component 2444 atraumatically contacts the wall of the ventricle within the nonfunctional portion of the partitioned ventricle, and distributes direct pressure on the wall to minimize stress on the cardiac wall in the nonfunctional portion of the partitioned ventricle through the feet 2455. Support component 2444 comprises a stem coupled to a non-traumatic base structure such as the plurality of feet 2455 and connected on its other extremity to the stem 2443 which extends distally from the non-pressure receiving side of the frame of the device. The support component 2444 can vary in length from about 3 mm to about 12 mm such that the non functional portion is sufficiently large in size/volume to partition necrotic tissue, such as tissue of a myocardial infarct (MI), a weakened cardiac wall, or the like. A web of material (not shown) may extend between adjacent feet 2445 to provide further support in addition to or in lieu of the supports 2446.

Figure 26:
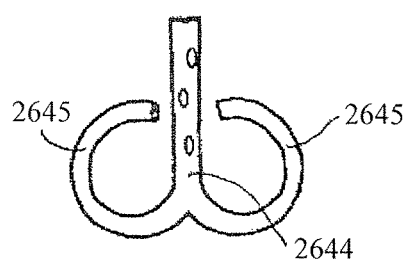
FIG. 26 is a partial elevational view of a diastolic recoil device embodying an alternative support component with curved bumper shaped feet.
Figure 27:
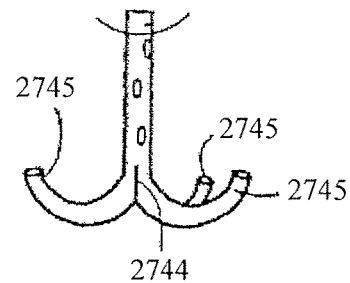
FIG. 27 is a partial elevational view of a diastolic recoil device embodying an alternative support component with J-shaped feet.
Figure 28:
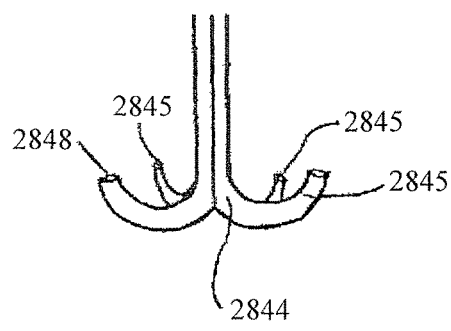
FIG. 28 is a partial elevational view of a diastolic recoil device embodying an alternative support component with J-shaped feet.
Figure 29:
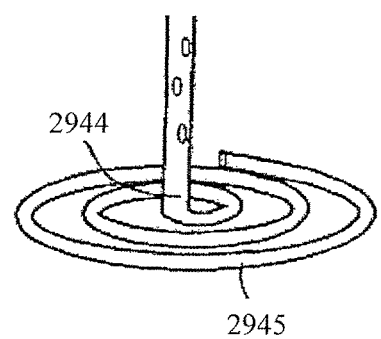
FIG. 29 is a partial elevational view of a diastolic recoil device embodying an alternative support component with J-shaped feet.

Alternative embodiments of the devices comprise feet as shown in FIGS. 25-29. FIG. 5 illustrates a diastolic recoil device 2530 comprising a frame 2533 with ribs 2534. The membrane 2531 is attached to the frame 2533 and the anchors 2537 contact the wall of the chamber to secure the device within the chamber in order to partition it. Device 2530 has a nontraumatic support component 2544 which has a simple rounded end which is connected to the stem 243. The stem 2543 is connected to the central hub 2532 which is connected to the frame 2533. FIG. 26 illustrates an alternative support component 2644 for the devices of the invention. Support component 2644 has a plurality of curved bumpers 2645 which act as "feet" and contact the wall of the chamber atraumatically. There may be a variable number of curved bumpers to distribute the force that the support component will deliver to the wall of the chamber. FIG. 27 illustrates an alternative support component 2744 which has feet such as the plurality of J-bumpers 2745. FIG. 28 illustrates a different embodiment of the support component 2844 which has a plurality of J-shaped bumpers 2845. FIG. 29 illustrates another embodiment of the support component 2944 which has a soft, non-traumatic coil 2945 which contacts the wall of the heart chamber, and distributes the force from a diastolic recoil device to a larger area of the wall of the heart, reducing strain on weakened or necrotic areas of the chamber.

Figure 30:
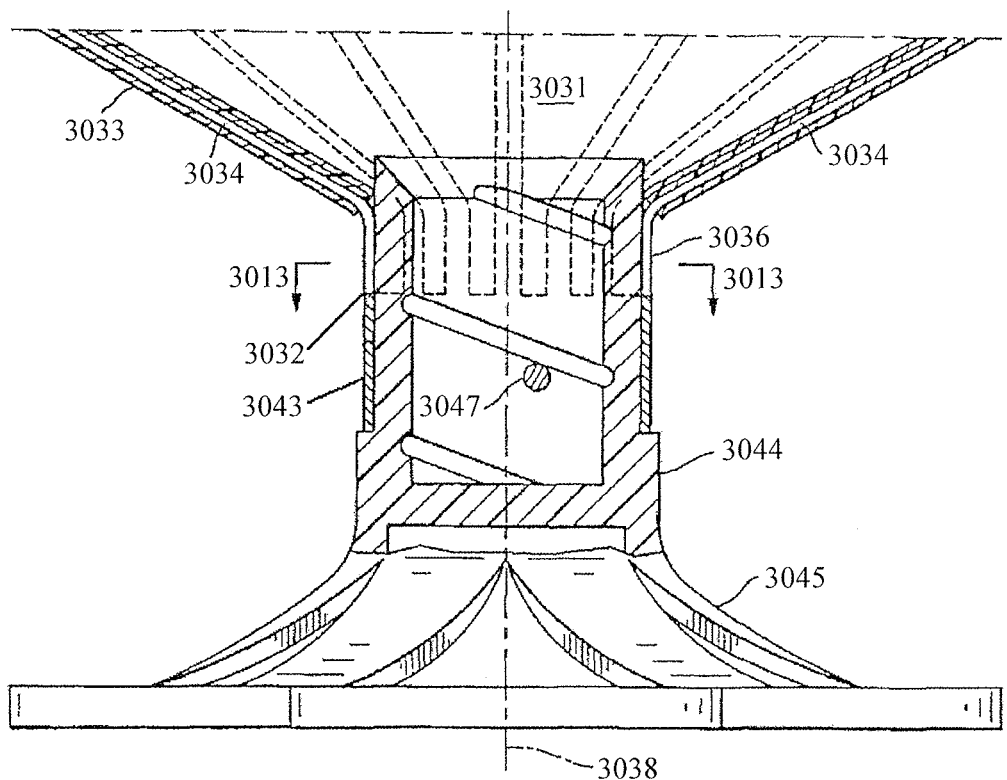
FIG. 30 is a partial cross-sectional view of a lower section of a diastolic recoil device as shown in FIG. 22 taken along the lines 2212-2212, showing details of connection of the ribs to the hub, the support component, and feet of a diastolic recoil device.
Figure 31:
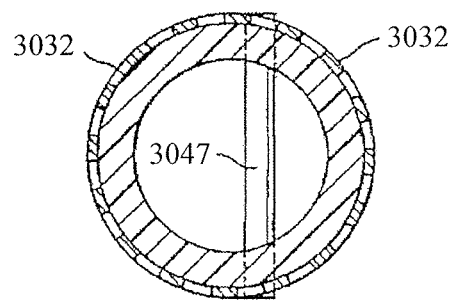
FIG. 31 is a detail cross sectional view of the hub of a diastolic recoil device as shown in FIG. 30, taken along lines 3013-3013.

As shown in FIG. 30 the distal ends 3036 of the ribs 3034 are secured within the hub 3032 and, as shown in the detail of FIG. 31, a transversely disposed connector bar 3047 is secured within the hub which is configured to secure the hub 3032 and thus the diastolic recoil device 3030 to a delivery system such as that described in co-pending applications referenced above. Ser. No. 10/913,608, filed on Aug. 5, 2004, entitled "Ventricular Partitioning Device", assigned to the assignee of the present invention, and incorporated herein by reference in its entirety. This connector bar permits selective connection of the diastolic recoil device to a delivery catheter for delivery within the ventricle, selective placement of the device once within the ventricle to partition the ventricle, selective deployment of the partitioning device and selective release of the diastolic recoil device from the delivery catheter. FIG. 30 also illustrates the connection between connector hub 3032, stem 3043, support component 3044, and feet 3045.

Figure 32:
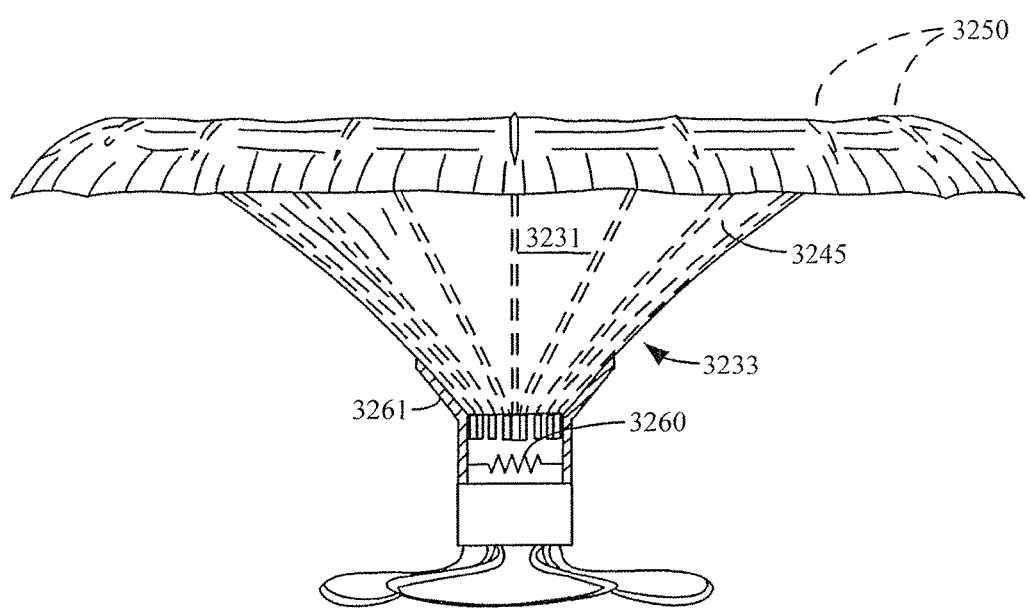
FIG. 32 is a plan view of a diastolic recoil device incorporating a delayed or damped spring release mechanism attached to the pressure bearing side of the frame of the device.

Another embodiment of the invention is envisioned wherein the device is utilized to deliver the recoil energy not throughout the phase of diastolic filling, but at selected time intervals during filling. A device 3230 further incorporating a delayed release spring 3260 as shown schematically in FIG. 32, can be utilized to assist diastolic function. In the top view of device 3230, delayed response spring 3260 is attached to restraint struts 3261 which in turn releasably contact the frame 3233 on the non-pressure bearing side 3245 of the membrane 3231. After installation by anchoring device 3230 to the ventricle walls with anchors 3250, the majority of the recoil force stored in the device is not freely releasable immediately at the end of systole. Instead, the ventricle begins an unassisted expansion while the device is partially secured from freely expanding. At a predetermined point during diastolic expansion, which may be customizable for each patient, the delayed release mechanism is triggered. The restraint struts are 3261 released from contact with the frame 3233, and the stored energy fully released at that point in the cardiac cycle. Thus, the majority of the recoil energy can be given back to the ventricular wall at a select point during diastole, as required for a particular patient. Another embodiment of this aspect of the invention may have a spring means including only a damped releasing mechanism. In these embodiments, the subsequent contraction of the ventricle during systole re-engages the delayed release spring mechanism or restores the damped spring to restore the contact between the restraint struts 3261 and the frame 3233 when the frame is in the compressed state for further cycles of delayed recoil assistance to the ventricle.

Figure 33:
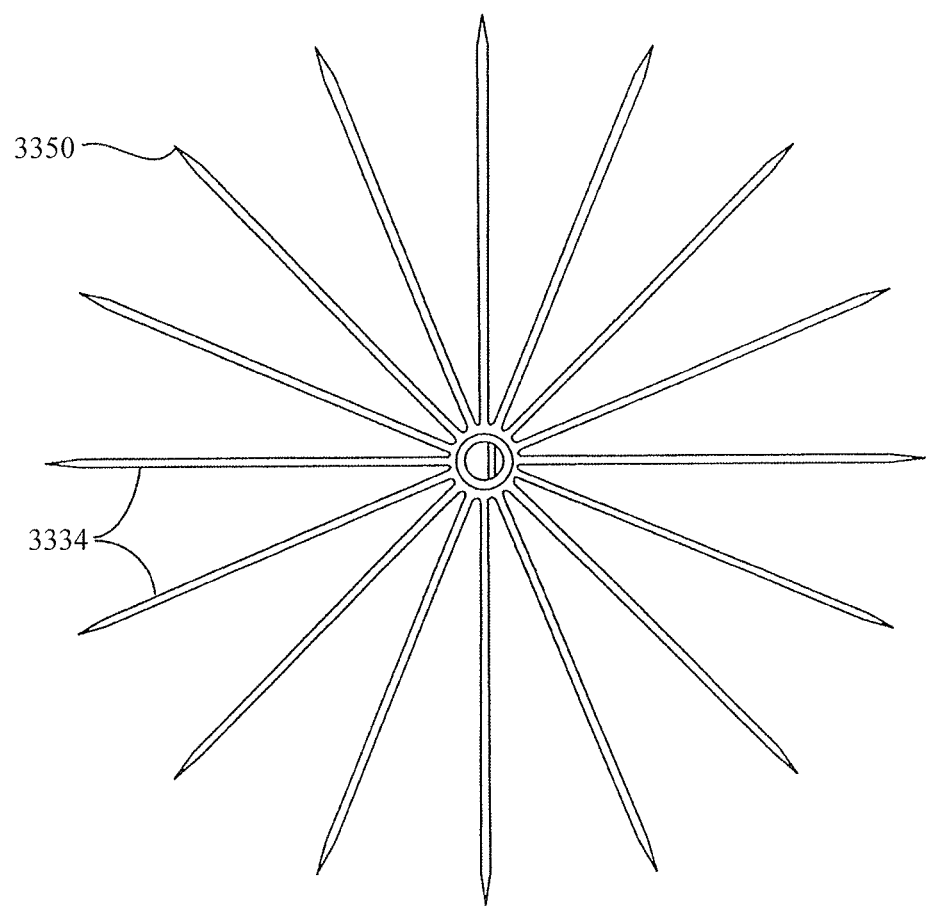
FIG. 33 is a plan view of a diastolic recoil device which includes a frame and a hub but no membrane.
Figure 34:
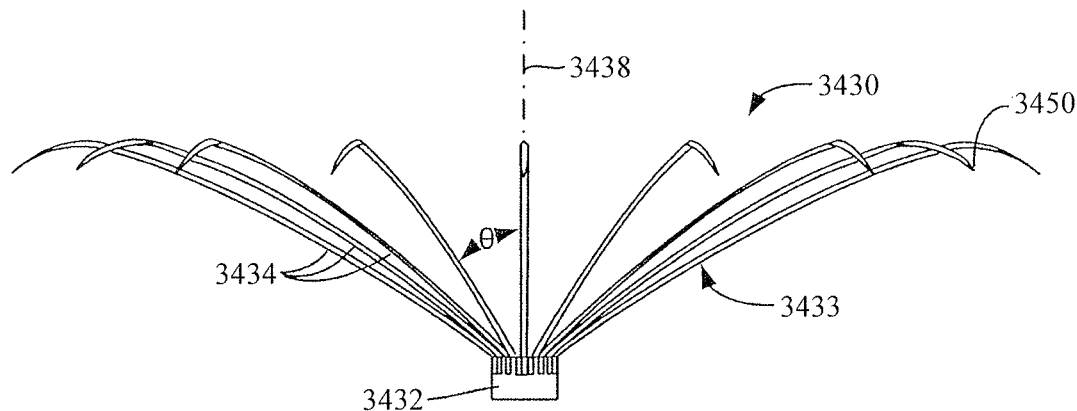
FIG. 34 is an elevational view of the device shown in FIG. 33.
Figure 35A:
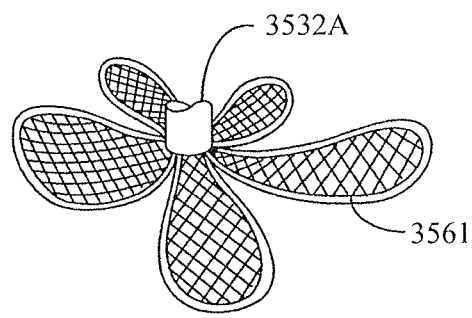
FIG. 35A is a partial elevational view of an alternate basal support for the device shown in FIGS. 33 and 34.
Figure 35B:
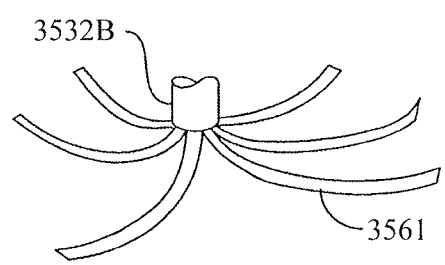
FIG. 35B is a partial elevational view of an alternate basal support for device shown in FIGS. 33 and 34.

Yet another embodiment of the invention can be envisioned for a patient population that has no systolic dysfunction but does have diastolic dysfunction. This population may not have dilation of the heart and partitioning the ventricle to reduce the volume of the ventricle is in this case not necessary. To gain more efficient diastolic filling, a device as shown in FIG. 33 may be utilized, which has a frame 3333 and central hub 3332 as previously described, but which has no membrane. The resilient frame provides force back to the walls of the ventricle and improves the diastolic function of the heart. The frame may need to be different from the frames of other embodiments of this invention, i.e. frame 2133 of FIG. 21. In this application, the ventricles of this population of patients may require more force to be applied back to the ventricular walls, which may be thickened and stiffened relative to healthy ventricular walls. It may also be necessary to increase the number of ribs, the thickness of the material of the ribs, the relative stiffness of the ribs, and/or use different alloys or material compositions to form the frame in order to manufacture a device with appropriate resiliency/stiffness properties. The device may seat lower in the ventricular chamber, and may thus require devices with smaller diameters relative to those used for patients with ventricular dilation. The size matching then is made for the end-diastolic diameter of a landing zone at a level further below the base of the papillary muscles. The unconstrained diameter of devices according to this embodiment of the invention may therefore be at least 25 mm up to about 90 mm. The central hub 3432, as shown in the side elevation view of a device depicted in FIG. 34, may not have any distal extension and may ends as a flat disk. A distal extension of hub 3432 may consist of a short rounded nub, or may connect to flexible basal supports which may stabilize the device in its seat in the apex of the ventricle. The basal supports may be configured in many ways. Two examples are given in FIGS. 35A and 35B respectively, shown as basal supports 3561A and 3561B.

Implantation of the devices herein can be accomplished endovascularly or intraoperatively in as little as one hour by a physician or appropriately trained personnel. Such implantation presents limited risk to the patient and requires the patient to be under a fluoroscope for a period of as little as 20 minutes.

Implantation of the diastolic recoil device in the ischemic and enlarged ventricle may bring back the ability of the ventricle to store elastic energy during systole and return this energy in the form of elastic recoil forces during diastole. In an embodiment, this return of energy in the form of elastic recoil may contribute to the improvement of the diastolic function, i.e., decrease of the filling pressure and increase in the magnitude of the early filling in patients with ischemic and/or dilated cardiomyopathy. Thus the ejection fraction of the chamber is increased by at least about a 5% change.

Suitable diastolic recoil device designs useful in the practice of the methods of the present invention have been described in co-pending applications, Ser. No. 11/151,164, filed Jun. 10, 2005, entitled "Peripheral Seal for a Ventricular Partitioning Device"; and Ser. No. 11/199,963, filed Aug. 9, 2005, entitled "Method for Treating Myocardial Rupture;" both of which are assigned to the assignee of the present invention, and incorporated herein by reference in their entirety. Diastolic recoil devices of the present invention are delivered percutaneously or intraoperatively. A suitable delivery device is described in co-pending application Ser. No. 10/913,608, filed on Aug. 5, 2004, entitled "Ventricular Partitioning Device", assigned to the assignee of the present invention, the full disclosure of which is incorporated herein by reference.

The diastolic recoil devices may be conveniently formed by the method described in above-referenced co-pending application Ser. No. 10/913,608 assigned to the assignee of the present invention and which is incorporated herein by reference in its entirety.

B. Uses of the Devices

Figure 36A:
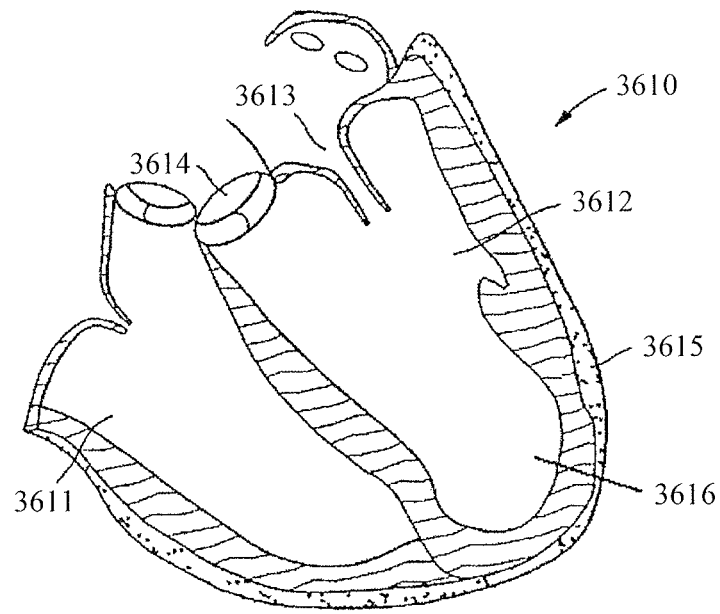
FIG. 36A is a schematic view of a patient's heart exhibiting characteristics of heart failure or incipient CHF.
Figure 36B:
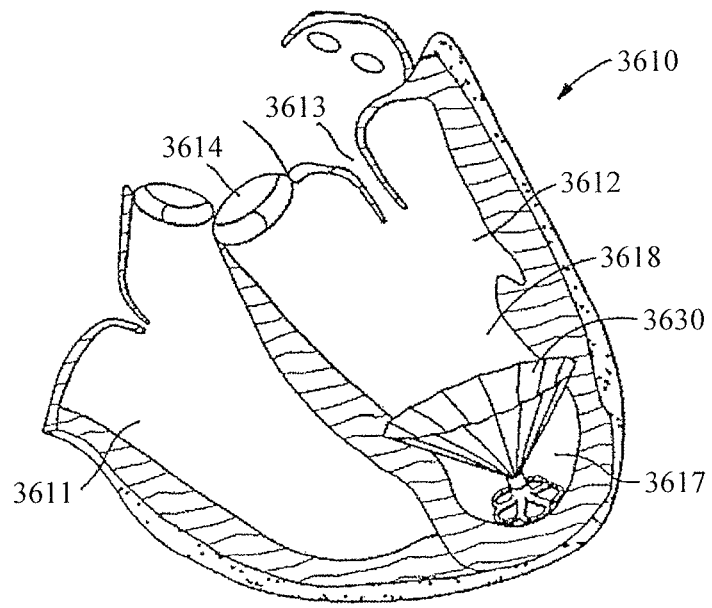
FIG. 36B is a schematic view of the patient's heart of FIG. 36A after treatment according to a method of the present invention using a round shaped diastolic recoil device.

FIG. 36A is a schematic illustration of a patient's heart 3610 showing the right ventricle 3611 and the left ventricle 3612 with the mitral valve 3613 and aortic valve 3614. A pericardium membrane 3615 is shown surrounding the heart 3610. FIG. 36A illustrates a patient's heart with apical dilatation (round enlarged apex 3616 of the LV) which can be found in patients exhibiting characteristics of congestive heart failure. FIG. 36B illustrates the left ventricle 3612 of FIG. 36A after it has been partitioned, with a diastolic recoil device 3630 having features according to the present invention and as described further below, into a main functional or operational portion 1618 and a secondary, essentially non-functional portion 3617.

In a diseased ventricle, the flow pattern of blood through the left ventricle 3612 can be abnormal due to both the abnormal geometry of the ventricle and from the lack of contraction in the akinetic portion of the ventricle, which is often located around the apex 3616 of the ventricle. The shape of the membrane, which can be trumpet or cone shaped as described herein, can also help restore a more normal flow surface to the ventricle which may result in a more normal flow pattern. Other shapes may also work, such as bowl shaped. By partitioning off the akinetic region and by restoring a more normal flow surface to the ventricle, abnormal flow patterns in the ventricle can be reduced. In addition, as shown in FIG. 36B, the device 3630 can be aligned with the left ventricular outflow path, which is the portion of the left ventricle 3612 that extends between the apex 3616 or apical portion of the left ventricle and the aortic valve 3614, such that the membrane of the device receives flow from the left atrium exiting the mitral valve 3613 and redirects it towards the aortic valve 3614 to exit the left ventricle, thereby restoring a more normal flow pattern within the ventricle. In some embodiments, the device 3630 can be additionally or alternatively aligned with the aortic valve such that at least a portion of the pressure or flow receiving surface of the membrane generally faces the aortic valve. In some embodiments, the a central axis extending through the hub of the device 3630 can aligned with the left ventricular outflow tract and/or aortic valve.

In some embodiments, the frame and membrane of the device can provide a trampoline effect where the frame and membrane move relative to the ventricle wall during diastole and systole. This relative movement and trampoline effect can be facilitated by separating or offsetting a portion of the frame and membrane, such as the central portion of the device, from the ventricle wall, while the peripheral portion of the frame and membrane are anchored to the ventricle wall. In some embodiments, the hub for foot of the device functions to provide the separation or offset from the ventricle wall. The length of the hub or foot can be selected to provide a predetermined amount of separation or offset from the ventricle wall. In addition, the membrane in conjunction with the frame can interact with the blood and transfer energy from and to the blood.

In some embodiments, the frame of the implant can be anchored in the healthy portion of the ventricular tissue in order to harness the motion from the healthy portion of the ventricle to create motion in the unhealthy, akinetic portion of the ventricle, thereby restoring some flow to the akinetic portion of the ventricle. As the healthy portion of the ventricle moves, the motion is transmitted or translated through the frame and membrane of the implant, by movement of the frame and membrane, to the akinetic portion of the ventricle where the implant extends. Typically, the akinetic portion may be located at or around the apex or apical region of the ventricle, and the motion of the healthy portion can be transmitted to the apex or apical region of the ventricle, thereby improving or restoring in part flow in the apical region of the ventricle. Flow from the apical region that contributes to the overall ejection fraction may be referred to as the apical ejection fraction. Therefore, the motion of the implant can improve or restore in part the apical ejection fraction.

In addition, the diseased, akinetic portion of the ventricle can be formed of relatively stiff and rigid scar tissue, as compared to healthy ventricular tissue. The flexible frame and membrane of the device can be placed over the diseased tissue to provide a more compliant and naturally behaving surface capable of deformation, which is also facilitated by the separation or offset from the ventricle wall. The frame can also exert an outward force that both anchors the device to the ventricle wall and assists the expansion of the ventricle during diastole, by storing energy during systole and releasing the energy during diastole to assist in diastolic filling of the ventricle, as further described herein.

Figure 37:
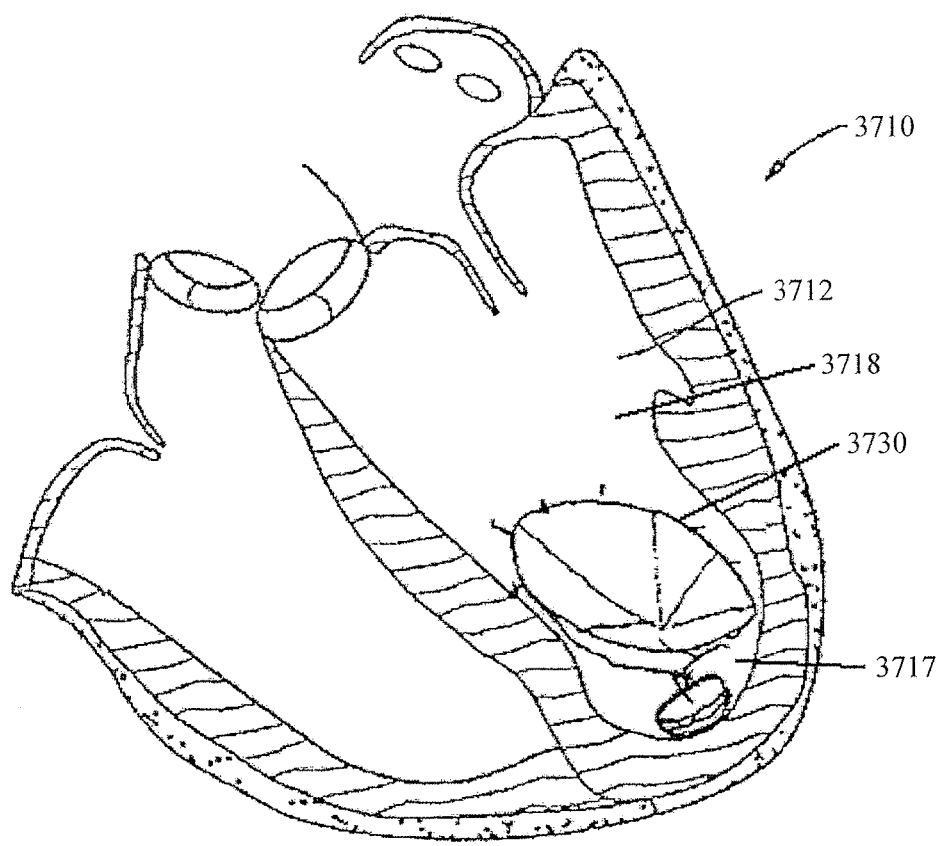
FIG. 37 is a schematic view of the patient's heart of FIG. 36A after treatment according to a method of the present invention using an elliptical shaped diastolic recoil device.

FIG. 37 is a schematic view of the patient's heart of FIG. 36A after treatment according to a method of the present invention using an elliptical shaped diastolic recoil device 3730. The device 3730 is implanted into the left ventricle 3712 of the heart 3710, creating a functional portion 3718 and nonfunctional portion 3717.

FIGS. 38A and 38B are drawings of echocardiograph images of a patient's heart at end-diastole, and end-systole, respectively. The contours of the diastolic recoil device implanted in the left ventricle are visible as fine white lines in the base of the ventricle. Portions of the ribs and periphery can be seen in FIGS. 38A and 38B.

As can be seen from FIGS. 38A and 38B, the diameter of the elastic diastolic recoil device is at its maximal implanted diameter (FIG. 38A) at end-diastole, and at its minimal implanted diameter at end-systole (FIG. 38B). End-systolic diameters (ESD) can be in the range from about 25 mm to about 55 mm. End-diastolic diameters (EDD) can be in the range of about 45 mm to about 70 mm. The compression of the partitioning device from end-diastolic to end-systolic configuration causes elastic recoil forces to be stored in the elastic frame of the device, and to be transmitted to the myocardium during ventricular filling in the outward direction thus enhancing outward motion of the ventricular walls. This storing and release of energy by the frame occurs in synchrony with the action of the heart. This transfer of energy may decrease the ventricular pressure in diastole, increase the atrio-ventricular pressure gradient, increase filling, and thus improve ejection fraction Dyskinetic or aneurystic ventricular walls result in dyssynchronous behavior during the cardiac cycle, leading to inefficient pumping function. Installation of a device of the invention can remove those dyssynchronous contributions to heart rhythms, restoring overall synchrony in the cardiac cycle, and thus improve ejection fraction. In one embodiment of the invention the partitioning device is substantially circular but another embodiment of the invention utilizes an elliptical shaped partitioning device as shown in FIG. 37. Other configurations of the partitioning device are compatible with the construction as described above and with methods to partition a chamber of a heart as set forth here.

The devices herein can be used to treat a patient suffering from a heart condition. Such heart conditions can include, for example, mitral valve regurgitation, myocardial infarction, or scar tissue or akinetic tissue in a heart chamber. A patient can be screened for treatment by the a devices herein by any means known in the art including, but not limited to, measurements of echocardiographic parameters may be such as decreased peak filling velocity and prolonged relaxation time, signs of increased filling pressure, clinical symptoms of dyspnea and peripheral edema, as well as low ejection fraction and a distance a patient can walk in 6 minutes.

Prior to the implantation procedure (as described further below), the diastolic recoil device implant may be matched to the size of the chamber where it is to be inserted (e.g. left ventricle) when the device is to be inserted into the left ventricle this can be accomplished by comparing the left ventricle end-diastolic diameter at the level of the papillary muscles base. This diameter is referred to hereinafter as the landing zone diameter. Measurement of landing zone diameter may be made by any method known in the art including; echocardiography, fluoroscopy, PET, MRI, contrast angiography, and the like, the landing zone diameter is the compared to the relaxed deployed/device diameter. When a device is to be implanted in a ventricle, the ventricle may be dilated such that its end diastolic diameter is greater than 45 mm or even greater than 65 mm. In some cases, to maximize the occurrence of a permanent seal between the implant and the endocardium, the relaxed diameter of the selected diastolic recoil device is oversized as compared to the diameter of the landing zone. The relaxed diameter of the device can be oversized by at least about 10% and up to 60% over the landing zone diameter.

The diastolic recoil device implanted thus decreases the LV volume by at least about 10% up to about 40%. The ratio of the nonfunctional portion to the functional portion, created by partitioning the ventricle by a method of the invention is at least 1:10 or up to about 1:3.

The diastolic recoil device frame is elastic and its diameter changes from a small diameter at end-systole to a larger diameter at end-diastole. The compression of the diastolic recoil device from end-diastolic to end-systolic configuration causes additional compressive forces to be stored in the elastic frame of the device, thus enhancing the ejection fraction of the chamber by at least about 10%, or up to about 90%.

Figure 39:
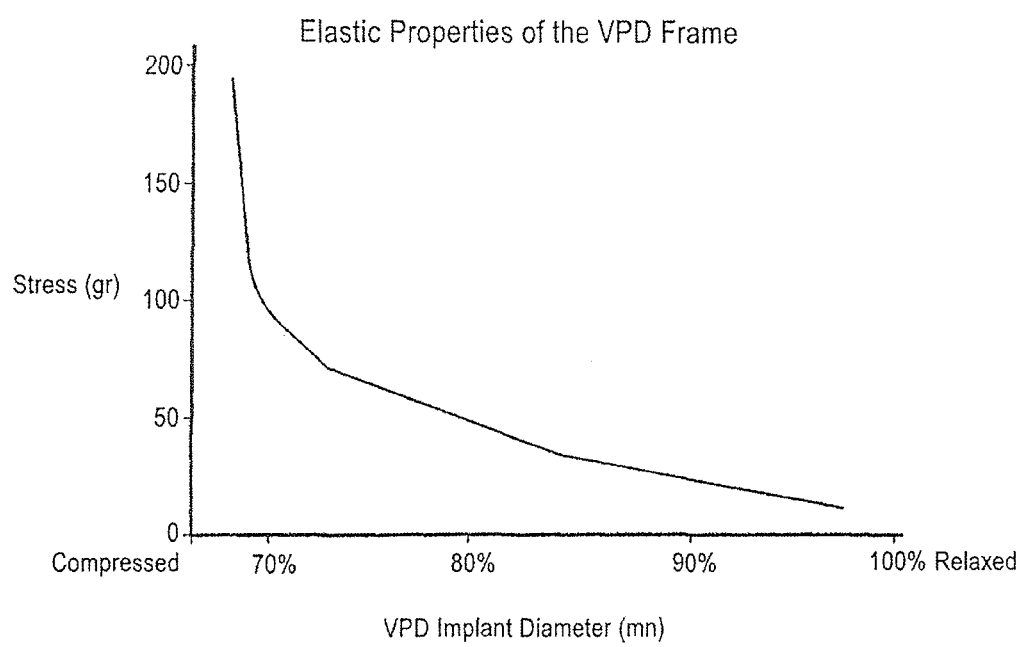
FIG. 39 is a diagrammatical illustration of the elastic characteristics of an embodiment of a diastolic recoil device implant.

The elastic characteristics of the diastolic recoil device implant may be determined by a tensile/compression test, an example of which is diagrammatically shown in FIG. 39. To conduct the test, the diastolic recoil device is positioned inside a custom designed fixture which was connected to a force transducer. The fixture was designed to create substantially equal compressive radial force (compatible and corresponding to physiological range of forces developed by normal myocardial fibers) on all ribs (as described below) of the implant, thus determining the compression stress-diameter relationship for the frame (as described below) of the device. FIG. 39 shows an exemplary elastic property of the diastolic recoil device. As can be noted from the figure, the magnitude of the elastic recoil forces stored in the diastolic recoil device implant increases as the diastolic recoil device diameter decreases under compression.

It can further be noted that the stiffness of the implant increases in a non-linear fashion as the diameter of the implant decreases as it is compressed to less than 50% of the diameter of the fully relaxed implant.

Figure 40:
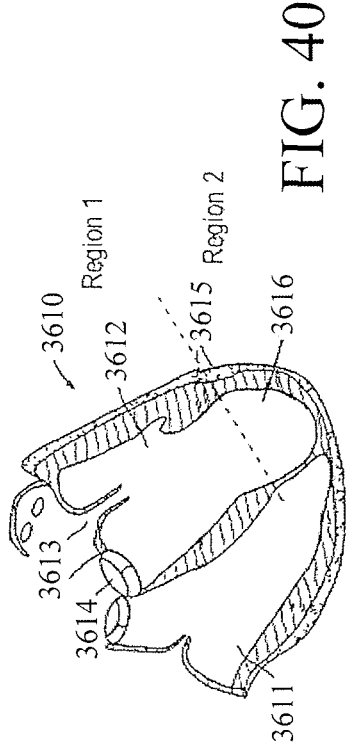
FIG. 40 is a schematic representation of a heart with a ventricle having two distinct regions of myocardium with different contractile properties, Region 1 and Region 2.
Figure 41:
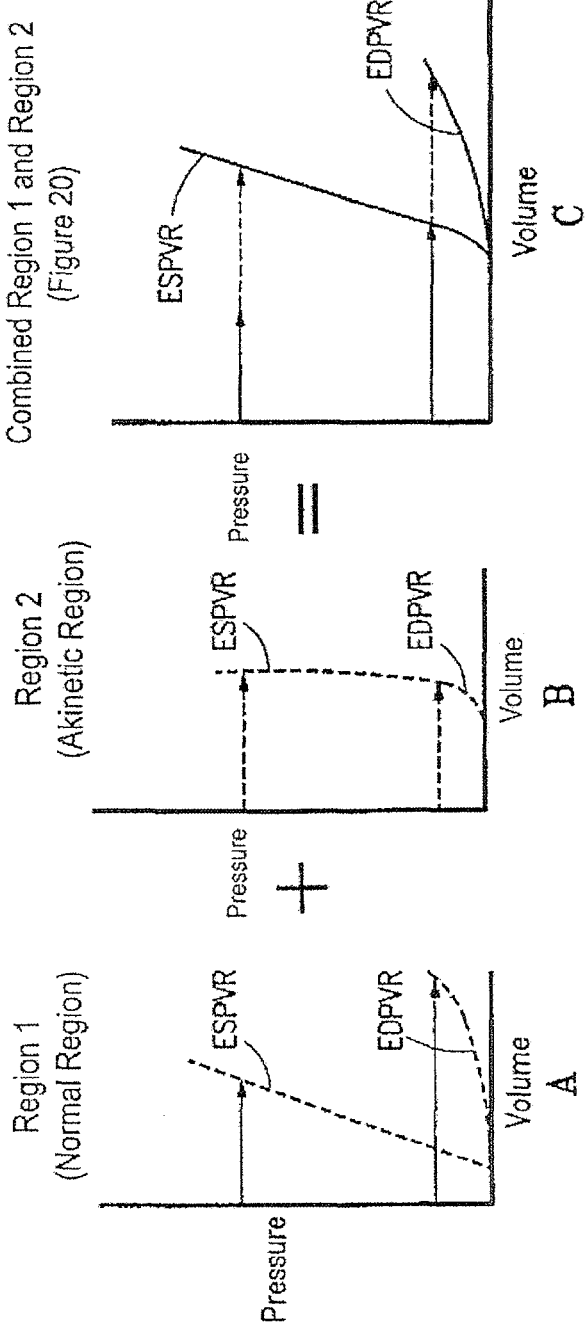
FIGS. 41A-C are diagrammatical representations of the end-systolic pressure volume relationship (ESPVR) and end-diastolic pressure volume relationship (EDPVR) of the ventricle of FIG. 40 prior to installation of a partitioning device.

Modeling experiments can be used to demonstrate the effect of implanting a diastolic recoil device of the invention. FIG. 40 is a schematic representation of a heart with dilation and poor function in the left ventricle, as illustrated also in FIG. 36A, having two distinct regions of myocardium surrounding the interior of the ventricle. Region 1 represents normal myocardium and region 2 represents dilated and dyskinetic or akinetic/myocardium. A simulation experiment is performed, using an elastance model, as described in J H. Artip; et al.; J. Thoracic and Cardiovascular Surg., 122(4), 775-782, 2001. The myocardial properties differ from one region to the next and the global ventricular properties are calculated by the interaction between the two virtual chamber regions, each chamber region having its own pressure volume characteristics. FIGS. 41A-C represent a simulation carried out using a ventricle as in FIG. 40 without a partitioning device. In FIGS. 41A and B, the dashed lines labeled ESPVR (End Systolic Pressure Volume Relationship) represent the maximal pressure that can be developed by that section of the ventricle at any given left ventricular volume. The dashed lines in FIGS. 41A and B labeled EDPVR (End Diastolic Pressure Volume Relationship) represent the passive filling phase for the respective regions of the un-partitioned ventricle, demonstrating the change in volume without great change in pressure, for each simulated region. As can be seen for Region 1 (normal), during systole the pressure changes rapidly relative to volume changes, while during diastole volume changes more rapidly (passive filling) relative to pressure changes. In contrast, in the akinetic region, Region 2, in FIG. 41B, there is no passive filling during diastole, hence the EDPVR is coincident with the ESPVR. Of note is the slope of the ESPVR in Region 2 (FIG. 41B), which is greater than that in Region 1 (FIG. 41A), as the slope is the reciprocal of ventricular compliance. Hence, akinetic Region 2 demonstrates greatly reduced ventricular compliance. The end-systolic pressure-volume relationship (ESPVR) and end-diastolic pressure-volume relationship (EDPVR) for the ventricle of FIG. 40 was determined by the sum (FIG. 41C) of the virtual volumes of the Regions 1 (FIG. 41A) and 2 (FIG. 41B) at each pressure, as shown by the solid lines drawn in FIG. 41C.

Figure 42:
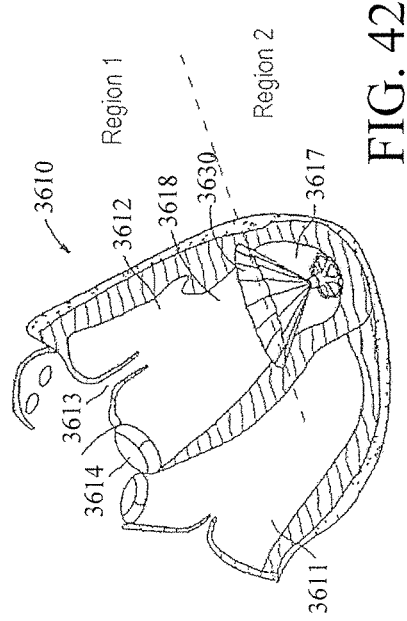
FIG. 42 is a schematic representation of a heart with a ventricle having two distinct regions after installation of a diastolic recoil device.
Figure 43:
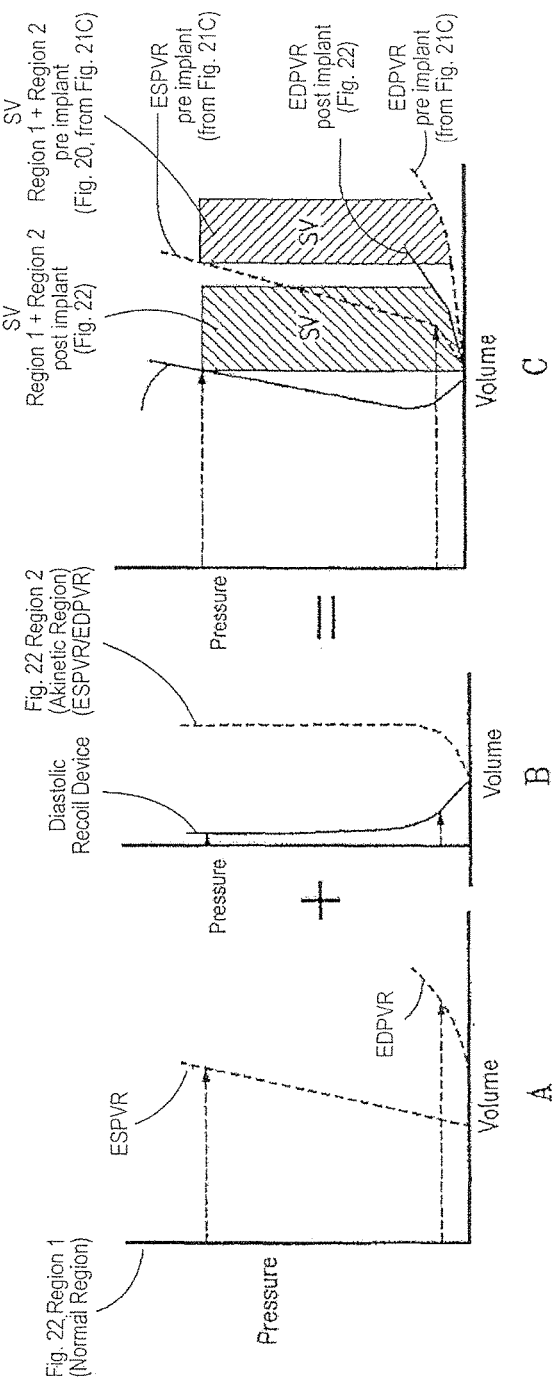
FIGS. 43A-C are diagrammatical representations of the ESPVR and EDPVR of the ventricle of FIG. 42 after treatment according to the present invention, and shows the comparison of the Stroke Volume, pre-implantation and post-implantation.

In the second part of the simulation experiment, the effect is modeled wherein the akinetic Region 2 of a ventricle with diastolic dysfunction (as shown in FIG. 42 and FIG. 36B) of the LV is partitioned by a partitioning device of the invention. The ESPVR and EDPVR for the individual contributions from normal Region 1, the diastolic recoil device, and akinetic Region 2 are represented in FIGS. 43A and B. The normal Region 1 now exhibits a steeper slope to its ESPVR as the diastolic recoil device isolates Region 2 from Region 1, reducing the overall volume and conferring greater resistance as systole proceeds. The solid line shown in FIG. 43B shows similar information as that in FIG. 39, as it represents the performance of the diastolic recoil device as it is compressed, and the dashed line in FIG. 43B is the ESPVR/EDPVR curve for the akinetic Region 2 in FIG. 42. The new ESPVR and EDPVR for the ventricle as a whole are shown in FIG. 43C, as solid lines. The corresponding ESPVR and EDPVR for the pre-implant ventricle from FIG. 41C are also reproduced in FIG. 43C as dashed lines for comparison. As can be seen in FIG. 43C, the ESPVR and EDPVR curves of the post-implant ventricle (solid lines) are shifted leftwards as compared to the curves of the dilated pre-implant ventricle (FIG. 43C "ESPVR Pre-Implant" and "EDPVR Pre-Implant", dashed lines). However, the ESPVR curve for the partitioned ventricle is shifted more than the EDPVR curve for the partitioned ventricle. This results in increased pump function of the ventricle which can be demonstrated by examining the resultant the pressure-volume loops. The stroke volume (SV) for the ventricle, pre-partitioned (FIG.

40) and partitioned (FIG. 42), are indicated by the shaded volumes labeled "SV Pre-Implant" and "SV Implant". The stroke volume is represented by the width of these shaded volumes as filling proceeds along the EDVPR curves. The right-hand boundary of the stroke volume is the pressure/volume line at end diastole, when isovolumetric contraction begins, and the left-hand boundary is the volume/pressure line representing isovolumetric relaxation during the heart cycle. The partitioned ventricle exhibits increased stroke volume (SV) compared to the dilated, pre-implant ventricle with akinetic Region 2 at comparable end-diastolic and aortic pressures ("SV Implant" vs. "SV Pre-Implant" in FIG. 43C).

Figure 44A:
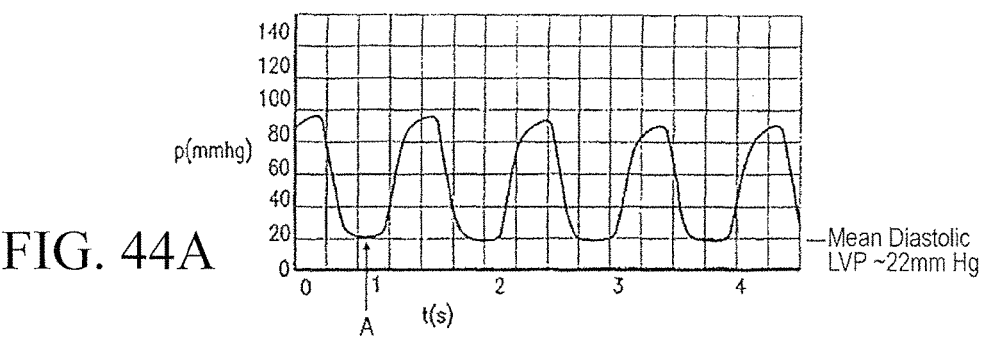
FIG. 44A is a diagrammatical illustration of the left ventricular pressure (LVP) in one dilated ventricle with diastolic dysfunction.
Figure 44B:
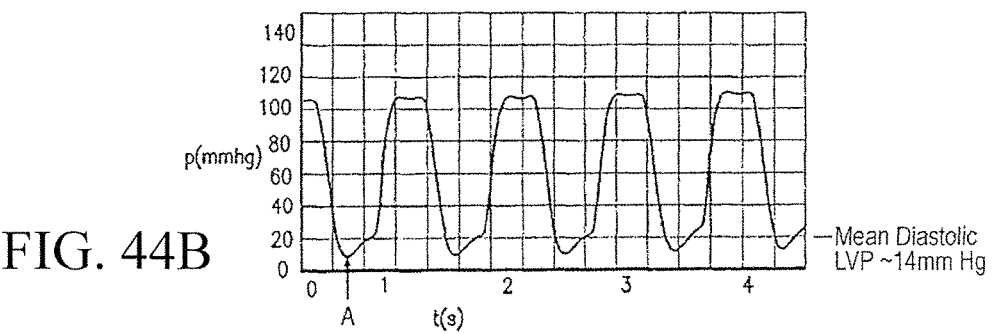
FIG. 44B is one diagrammatical illustration of the left ventricular pressure (LVP) of the ventricle of FIG. 44A after treatment according to the present invention.

FIGS. 44A and 44B, are diagrammatical illustrations of the recordings of the left ventricular pressure (LVP) in one dilated ventricle with diastolic dysfunction before and after implantation of a diastolic recoil device, respectively. In FIG. 44A, diastolic dysfunction results in inefficient filling of the ventricle at relatively high mean diastolic pressure in the ventricle. The akinetic ventricle can neither compress nor expand as effectively as a normal ventricular chamber. The resultant filling pressure at early diastole is therefore higher than in a healthy heart and early filling is decreased. During installation of the diastolic recoil device, the device is anchored to functional portions of the ventricle wall, partitioning the akinetic (nonfunctional) portion of the chamber. This mode of attachment allows the elastic frame of the partitioning device to gain energy from the effectively contracting portion of the ventricular wall, by compressing the elastically resilient frame. As the ventricle relaxes and expands, the energy stored in the frame is released and imparts additional recoil force back to the ventricle wall, which aids in the process of filling the ventricular chamber. As can be seen from FIGS. 44A and 44B, implantation of the diastolic recoil device resulted in decreased minimum diastolic pressures. In this example the minimum LV pressure is decreased by at least 50% (contrasted by points A and A' in FIGS. 44A and 44B respectively) and mean diastolic pressure at least by 10%. The contribution of the elastic energy from the frame assisting expansion of the walls of the ventricle was observed in early diastole, thereby augmenting filling and normalizing diastolic pressure. Decreased mean diastolic pressure of the partitioned ventricle compared to that of the pre-implant ventricle indicates improved diastolic function (mean diastolic LVP of ca. 14 mm Hg in FIG. 44B vs. "mean diastolic LVP of ca. 22 mm Hg in FIG. 44A). These results demonstrate that the diastolic recoil device improves either or both the systolic and diastolic LV function in the remodeled LV with a dysfunctional myocardial region.

The use of a diastolic recoil device and methods of the invention yields a decrease of minimum LV pressure during diastole by at least about 5% up to about 100%. The use of a diastolic recoil device by the methods of the invention yields a decrease of end-diastolic pressure by at least about 5%, and up to about 35%.

Other indicators of LV function may be measured upon installation of the diastolic recoil device. Some of these indicators are hemodynamic measurements, such as, for example, left ventricle end systolic volume index (LVESVI). LVESVI indicates the size of the ventricle at end systole with values normalized to body size. The baseline value for a healthy individual is ~25 ml/m2. LVESVI has significant predictive value for survival outcome, and may represent the most significant correlation used in diagnosis and treatment. In some cases, a patient can be first diagnosed as having heart disease by determining or detecting in that patient a LVESVI greater than 60 ml/m2. Such patient is thus treated by implanting one or more of the devices herein. The diastolic recoil device, by partitioning the ventricle into functional and non-functional portions, causes an initial decrease in LVESVI upon installation. The implantation of the diastolic recoil device may also promote positive remodeling of the ventricle to further decrease ventricle volume as the supported cardiac muscle more effectively contracts and expands, thus decreasing LVESVI by at least 5%.

Left ventricle ejection fraction (LVEF), another hemodynamic measurement, is the percentage of the end diastolic blood volume expelled from the ventricle upon each cardiac cycle. LVEF of 60% or greater are seen in healthy individuals, while an LVEF of 40% is considered the threshold value for diagnosis of heart failure with systolic dysfunction. Implantation of the partitioning device increases the LVEF by at least about 5% and up to about 90%.

Other indices of ventricular function may also be used for diagnosis and for therapeutic follow-up. A number of biochemical markers may be measured and used. One example is NT Pro-Brain Natriuretic Peptide, but many other biological molecules, for example, neurohormones, proteases, and proteins related to distressed or abnormal function may be measured to give quantification of the relative functionality of the ventricle prior and post-implant.

NT-Pro-Brain Natriuretic Peptide (NT-Pro-BNP) is a regulatory peptide that is produced in the ventricle and has been shown to be related to the level of stress in myocardium, as well as involved in adverse remodeling processes seen in late stage disease. A normal NT-BNP level for a healthy individual is generally in the range of 20-30 pg/ml, while in an individual with end stage heart failure, a level can be as high as 2000-3000 pg/ml, and in some instances there may be a correlation between BNP levels and LVEF. The use of NT-Pro-BNP levels as reliable markers for heart disease in a number of patient populations has been proposed (J. L. Januzzi; Cleve. Clin. J. Med., 73(2), 149-52, 155-7, 2006) and may offer advantages in ongoing patient monitoring and care. Thus the present invention contemplates treating a patient by first determining the level of NT-Pro-BNP, and if the level of NT-Pro-BNP is greater than 170 pg/ml (third quartile) or 450 pg/ml (fourth quartile), delivering to such patient one or more of the devices herein. Implantation of a diastolic recoil device improves cardiac function, and decreases the level of NT-Pro-BNP observed post-implant by at least about 10%.

Mitral valve regurgitation can be observed in patients with diastolic dysfunction, and is coupled to poor outcome. Mitral valve regurgitation increases in magnitude as the ventricle increases in size due to pathological dilation. Intervention is often necessary as blood backflow into the atrium leads to accelerated progression of heart failure. Standard therapies include both prescribed medications (i.e. vasodilators like ACE inhibitors and nitrates, and diuretics) and surgical interventions to repair or replace mitral valves. However, these surgical interventions are invasive and may present high risk to the patient. Diastolic recoil device implantation can reverse the decline in ventricular function by decreasing the effective ventricular volume which may obliterate or attenuate the cause of the mitral valve regurgitation. The severity of mitral valve regurgitation is categorized by measuring the regurgitant fraction by, for example, echocardiography. Color Doppler flow on a transthoracic echocardiogram measures the forward flow through the mitral valve during ventricular diastole and compares it to the outflow of blood through the aortic valve in ventricular systole, permitting the calculation of the regurgitant fraction. The present invention contemplates treating a patient by first determining the degree of mitral regurgitation as assessed by the regurgitant fraction and if the regurgitant fraction is at least 20%, delivering to such patient one or more of the devices herein. Diastolic recoil device implantation may therefore benefit patients with mitral valve regurgitation from any clinically relevant cause and decrease the regurgitant fraction by at least about 10%.

Although reference is made to a diastolic recoil device which is implanted in the left ventricle, it is understood by those skilled in the art that such reference is not limiting and similarly suitable diastolic recoil devices may be used in the right ventricle or other heart chambers.

EXAMPLES

Example 1

Symptomatic heart failure patients (New York Heart Association Classification levels II and III) diagnosed with ischemic cardiomyopathy post anterior infarction and systolic dysfunction were enrolled in a study implanting a diastolic recoil device similar to the one shown in FIG. 21. Size selection of the specific device was based on echocardiography comparison with a mean landing zone diameter of 55.1 mm (mean diastolic value or largest value achieved during cardiac cycle). Either 75 mm (3/9 patients) or 85 mm (6/9 patients) diameter devices were installed in a 95.7 minute (mean value) procedure, requiring mean fluoroscope time of 25.5 minutes.

A number of hemodynamic and biochemical variables were examined in each patient before implant and at 90 day post implant and are represented in Table 1 below. Data is available for 4 patients at the 90 day timepoint.

TABLE 1

| Exploratory Endpoints All data as mean values | Baseline (n = 9) Before Implant | 90 days (n = 4) |
|---|---|---|
| LVESVI (ml/m$^2$) | 101.8 | 72.7 |
| LVEF (%) | 29.3 | 37.2 |
| Patients with MR | 5/9 | 1/4 |
| NT-Pro-BNP (pg/ml) | 566 | 393 |

Left ventricle end systolic volume index (LVESVI) in a healthy individual is usually around 25 ml/m2. The mean baseline value for the patient group is notably higher, at 101.8 ml/m2. Significant reduction to 72.7 ml/m2 (~25%) for the LVESVI is observed at 90 days post implant. The ventricle has thus improved in function and was positively remodeled.

Left ventricle ejection fraction (LVEF) in a healthy individual is usually at least 60%. For this group the mean value observed before implantation of the device was 29.3%, slightly less than half of the value seen for healthy patients. At 90 days post intervention an increase in LVEF to 37.2% is observed which is an improvement of about 27%. This is a significant improvement as the threshold value of LVEF to diagnose heart failure is often placed at 40%.

In the overall patient cohort, a significant proportion of the patients (5 of 9) experienced mitral valve regurgitation (MR) prior to implantation. Of four patients who had experienced MR prior to implantation and for whom data at 90 days post implantation is available, three patients had remission of symptoms, with only one patient still experiencing MR. Thus, the improvement in LV function provided by implantation of a diastolic recoil device also provided reduction in MR regurgitation.

NT-Pro-brain Natriuretic peptide (NT-Pro-BNP) levels for a healthy individual are estimated to be in the range of 20-30 pg/ml. In the group of patients analyzed, the baseline mean value of NT-Pro-BNP prior to implantation was 566 pg/ml. This was significantly decreased by the 90 day timepoint to 363 pg/ml, an improvement of about 36%.

In Table 2 below represents data of overall functionality for the individual patients. The 6 minute walk is a simple test which measures the distance a patient is able to traverse during a 6 minutes timed period. The mean distance the patient cohort traveled prior to implant was 328 m. Ninety days post implant, data available for 4 patients shows significant improvement (~44%) to 471 m. The New York Heart Association (NYHA) Classification levels for the patients prior to implantation were Class II/III for this group. At the 90 day timepoint, reassessment of the NYHA Classification was performed on the four patients with available data. Three of the four individuals could be reassigned to less severe disease classifications. Finally, the patients performed a self scoring questionnaire, the Minnesota Living with Heart Failure test (MLHF), and registered significant improvement in self assessment of functionality. Thus, implantation of a diastolic recoil device of this invention demonstrated clear and self evident improvement in function and quality of life for the patient group.

TABLE 2

| Exploratory Endpoints Mean Values | Baseline (n = 9) Before Implant | 90 days (n = 4) |
|---|---|---|
| 6 min walk (m) | 328 | 471 |
| Improvement in NYHA class | — | 3/4 (75%) |
| MLHF | 22.9 | 12.7 |

The present invention is directed to methods for the treatment of a patient's heart having, or one which is susceptible to, heart failure, in particular, a patient's heart exhibiting diastolic dysfunction. The diastolic dysfunction may be a result of one or more conditions, for example, reduced elastic recoil in the ventricular chamber, more specifically the left ventricle. Diastolic dysfunction is established, for example, by measurements of various echocardiographic parameters such as decreased peak filling velocity and prolonged relaxation time, signs of increased filling pressure, and clinical symptoms of dyspnea and peripheral edema.

In one aspect of the invention a diastolic recoil device is provided which includes a membrane, a hub, preferably centrally located on the diastolic recoil device, and a radially expandable reinforcing frame formed of a plurality of ribs. For example, there may be at least 3 and up to 20 ribs, depending on the application. An elastic, resilient frame may be used. The ribs have distal ends which may be pivotally mounted to the hub and biased outwardly or fixed to the hub, and free proximal ends which are configured to curve or flare away from a center line axis upon expansion of the partitioning device. Tissue penetrating proximal anchors of the free proximal ends are configured to penetrate the tissue lining at an angle 30-120 degrees to the centerline axis of the diastolic recoil device. The tissue penetrating proximal anchors of the ribs may be provided with barbs, hooks, and the like which prevent undesired withdrawal of the tips from the heart wall. The diastolic recoil device and its components may be made with various sizes and diameters. The unconstrained diameter (D, in FIG. 1) of the diastolic recoil device may be about 40 mm to about 100 mm, and the height of the device when expanded (H, in FIG. 1) may range from about 10 mm to about 60 mm, and when collapsed, the diastolic recoil device of any size will fit within a catheter of less than 12 mm for delivery. In some embodiments, the unconstrained diameter of the diastolic recoil device is chosen to be oversized in relationship to the diameter of the ventricle that it is installed within. In one embodiment, a single strand extends around essentially the entire periphery of the membrane so that the flexible periphery of the membrane between each pair of ribs is effectively sealed against the heart wall. The hub may have a distally extending stem with a non-traumatic support component. The distally extending stem with non-traumatic support component together may extend a variable distance from the base of the hub. The stem may extend from about 2 mm to 20 mm from the hub to space the central hub a selected distance from the wall of the ventricle where the diastolic recoil device is seated. In some embodiments, the stem distance can be varied while retaining the same diameter membrane, thus permitting variable partitioning of the volume of the chamber. In some embodiments the support component has a plurality of pods or feet, e.g., at least three, or any number desired to distribute the force of the diastolic recoil device about a region of the ventricular wall surface to minimize, and preferably avoid immediate or long term damage to the tissue of the heart wall, by partitioning necrotic tissue such as tissue of a myocardial infarct (MI), or supporting weakened cardiac wall, and the like.

In another aspect of the invention, a diastolic recoil device adapted for percutaneous delivery to a ventricle of a heart of a patient comprising a plurality of radially expandable ribs connected at their distal ends to a central hub, is implanted in the ventricle of the patient wherein the radially expandable ribs are adapted to provide elastic support between opposing ventricular walls.

In an embodiment of the invention, a diastolic recoil device adapted for percutaneous delivery to a ventricle of a heart of a patient comprising a plurality of radially expandable ribs coupled at their distal ends to a central hub is implanted in the ventricle, wherein the ribs are adapted to augment ventricular wall movement during diastole.

In yet another embodiment of the invention, a diastolic recoil device adapted for percutaneous delivery to a ventricle of a heart of a patient comprising a plurality of radially expandable resilient ribs connected at their distal ends to a central hub and one or more anchor elements at each of the proximal ends of the ribs are adapted to secure the device to a selected area of a wall within the ventricle, wherein the ribs are adapted to support the wall and unload the cardiomyocytes to limit remodeling of the heart.

In another embodiment of the invention, a diastolic recoil device adapted for percutaneous delivery to a ventricle of a heart of a patient comprising a plurality of radially expandable ribs connected at their distal ends to a central hub is implanted in a patient, wherein the ribs are adapted to reduce diastolic pressure of a ventricle of the heart once deployed.

In still another embodiment, a diastolic recoil device adapted for percutaneous delivery to a heart of a patient comprising a plurality of radially expandable ribs connected at their distal ends to a central hub; and a plurality of anchor elements attached to a plurality of said ribs at their proximal ends wherein the anchor elements are adapted to secure the apparatus to a wall of a ventricle of said heart; and, wherein once the device is implanted in a ventricle of a patient, the device is adapted to reduce a volume of the ventricle to improve the pressure-volume relationship of the ventricle.

In another embodiment, a diastolic recoil device comprising a resiliently deformable member and a plurality of anchors, is delivered percutaneously to and anchored within the interior of a ventricle of a patient's heart to span a region of said ventricle, wherein the resiliently deformable member deforms from a first shape to a second shape during systole and to return to the first shape during diastole to assist in expansion of the ventricle.

In other embodiments, a diastolic recoil device comprising a resiliently deformable member and a plurality of anchors, is delivered percutaneously to and anchored within the interior of a ventricle of a patient's heart to span a region of the ventricle, where the resiliently deformable member stores energy during systole and releases stored energy back to a wall of the ventricle in synchrony with a heart cycle.

In some embodiments, a diastolic recoil device further comprises a delayed release spring having either a damped expansion mode or a triggered release such that the release of recoil forces back to the walls of the ventricular chamber can be selectively timed during diastole. This may aid individuals who require additional force to be applied back to ventricular walls during differing portions of diastole.

In yet another embodiment of the invention, a patient may be treated who has no systolic dysfunction, but does have diastolic dysfunction. Devices and methods are provided which utilize a diastolic recoil device having a frame and a hub which can provide force back to the walls of the ventricle. However, the device does not have a membrane as partitioning a portion of the ventricle may not be necessary for these patients. The frame may need differing characteristics to perform, as these patients may require more force to be applied to potentially stiffened and thickened heart walls. Therefore the number of ribs may be increased, the thickness of the ribs may be increased, the stiffness of the ribs may be increased, or the type of alloys or composite of which the frame is made may be different from other devices provided for in this invention. In this embodiment, the device may be seated lower than the base of the papillary muscles in the ventricle. The unconstrained diameter of such a device may be at least about 25 mm to about 90 mm.

In another aspect of the invention, methods are provided which include partitioning a chamber (e.g., left and/or right ventricles) of a patient's heart, exhibiting diastolic dysfunction disorder, or one which exhibits the characteristics of diastolic dysfunction, into a functional portion and an excluded, nonfunctional portion by implanting a diastolic recoil device according to the present invention.

Some embodiments of the invention includes the use of a diastolic recoil device having a partitioning membrane, preferably a reinforced partitioning membrane, with a pressure receiving surface, preferably concave, which defines in part the functional portion of the partitioned heart chamber when implanted or anchored within the patient's heart, in particular, within the ventricle.

In other embodiments of the invention a patient suffering from a heart condition is treated by advancing percutaneously a collapsed diastolic recoil device comprising a plurality of radially expandable ribs connected at their distal ends to a central hub and having an anchor element at the proximal end of each of the ribs; expanding the ribs in a ventricle of the heart; and, securing the device to a selected area of a wall of the ventricle with the anchor elements thereby providing elastic support between opposing ventricular walls. The ribs thus absorbing and releasing recoil forces back to the area of attachment reduce forces directed at the area of the heart in the newly created nonfunctional portion of the ventricle. This reduction eases pressure on a weakened area of a cardiac wall of the nonfunctional portion of the chamber.

The storing and release of energy by the frame occurs in synchrony with the action of the heart. This transfer of energy may decrease the ventricular pressure in diastole, increase the atrio-ventricular pressure gradient, increase filling, and thus improve ejection fraction Dyskinetic or aneurystic ventricular walls result in dyssynchronous behavior during the cardiac cycle, leading to inefficient pumping function. Installation of a device of the invention can remove those dyssynchronous contributions to heart rhythms, restoring overall synchrony in the cardiac cycle, and thus improve ejection fraction.

In yet another embodiment of the method a patient suffering from a heart condition is treated by advancing percutaneously a collapsed diastolic recoil device comprising a plurality of radially expandable ribs connected at their distal ends to a central hub and having an anchor element at the proximal end of each of the ribs; expanding the ribs in a ventricle of the heart; and, securing the device to a selected area of a wall of the chamber with the anchor elements thereby augmenting a ventricular wall movement during diastole.

Another embodiment of the method treats a patient suffering from a heart condition by advancing percutaneously a collapsed diastolic recoil device with a plurality of radially expandable resilient ribs connected at their distal ends to a central hub, and an anchor element at the proximal end of each of the ribs; expanding the ribs in a ventricle of the heart; and, securing the device to a selected area of a wall of the ventricle with the anchor elements wherein the ribs support the ventricular wall, unloading the myocardium, decreasing stress and thus benefiting mechanical function. More efficient function and decreased stress leads to decreased rates of dilation, and hence may limit remodeling of the heart.

Still another method of the invention treats a heart of a patient by advancing percutaneously a collapsed diastolic recoil device comprising a plurality of radially expandable ribs connected at their distal ends to a central hub and having an anchor element at the proximal end of each of the ribs into a ventricle of the heart; expanding the ribs in the chamber of the heart; and, securing the device to a selected area of a chamber wall with the anchor elements thereby reducing the diastolic pressure of the ventricle.

In another aspect of the invention methods are provided to reduce mitral valve regurgitation by advancing percutaneously a collapsed diastolic recoil device comprising a plurality of radially expandable ribs connected at their distal ends to a central hub and having an anchor element at the proximal end of each of the ribs; expanding the ribs in a ventricle of the heart; and, securing the device to a selected area of a wall of the ventricle with the anchor elements thereby reducing mitral valve regurgitation.

Another embodiment of the invention is a method of treating a patient suffering from a heart condition by advancing percutaneously to the interior of a ventricle of the patient's heart a diastolic recoil device comprising a resiliently deformable member and a plurality of anchors; securing the device to opposing wall sections of the ventricle with the anchors; deforming the deformable member as the opposing wall sections move toward each other during systole; and providing a recoil force from the deformable member to the wall sections during diastole.

Yet another embodiment is a method of treating a patient suffering from a heart condition by advancing percutaneously to the interior of a ventricle of the patient's heart a diastolic recoil device comprising a resiliently deformable member and a plurality of anchors; securing the diastolic recoil device to opposing wall sections of the ventricle with the anchors; storing energy within the deformable member as the opposing wall sections move toward each other during systole; and releasing energy from the deformable member to the wall sections during diastole.

In some embodiments of the invention, use of the diastolic recoil device or the methods of treatment results in improvement in the ejection fraction of the ventricle. The ejection fraction increase may be at least about 5% up to about 90%.

In some embodiments of the invention, use of the diastolic recoil device or the methods of treatment results in decreasing the left ventricle (LV) functional chamber by about 10% to 40%.

In some embodiments of the invention, use of the diastolic recoil device or the methods of treatment results in decreasing minimum LV pressure during diastole at least by about 5%.

In some embodiments of the invention, use of the diastolic recoil device or the methods of treatment results in decreasing end-diastolic pressure by at least about 5%.

The diastolic recoil device may be installed according to the methods of the invention in about one hour. The implantation of the device according to the methods of the invention requires require periods of about 25 minutes under a fluoroscope to install the partitioning device.

Similarly suitable diastolic recoil devices and methods may be used in the left or right ventricle or other heart chambers.

In some embodiments of the invention, after implantation of a diastolic recoil device of the invention, the left ventricle end systolic volume index (LVESVI) of the patient is decreased at least by about 5%.

In other embodiments of the invention, a number of biochemical markers are measured to evaluate cardiac function. One of these, NT-Pro-Brain Natriuretic Peptide (NT-Pro-BNP), is a regulatory peptide which is produced in the ventricle, and is related to the level of stress in myocardium. NT-Pro-BNP is decreased post-implant by at least about 10%.

In some embodiments of the invention, implantation of a partitioning device reverses the decline in ventricular function which may mitigate mitral valve regurgitation and/or decrease the stress on impaired valve leaflets sufficiently to alleviate regurgitation. Diastolic recoil device implantation according to this invention may therefore benefit patients with mitral valve regurgitation from any cause and decreases the regurgitant fraction by at least about 10%.

The following description of the preferred embodiments of the invention is not intended to limit the invention to these preferred embodiments, but rather to enable any person skilled in the art to make and use this invention. Described herein are devices, systems and methods for improving cardiac function.

The present invention is directed to devices and methods for the treatment of a patient's organ such as a heart. In some cases the heart is susceptible to or experiencing systolic or diastolic dysfunction, mitral valve regurgitation or heart failure.

Diastole is the phase of cardiac cycle during which relaxation of the heart muscles occurs after ejecting blood into general circulation and is governed by active and passive properties of the myocardium, geometrical characteristics of the chamber and external forces.

In the cardiac cycle left ventricular diastolic filling begins with opening of the mitral valve as pressure in the ventricle falls below pressure in the atrium. As the ventricle begins to contract the pressure in the ventricle soon exceeds that of the atrium and the mitral valve closes, which marks the end of diastole. The ventricular pressure and volume at this point are referred to as end-diastolic pressure ("EDP") and end-diastolic volume ("EDV"), and the beginning of ventricular systole.

The rate and amount of left ventricular diastolic filling depends upon the positive pressure upstream of the left ventricle provided by venous return and decreasing pressure provided within the left ventricle by expansion of the ventricle during diastole. A reduction in ventricular compliance (i.e., increase in stiffness of ventricular heart wall) may result in less diastolic expansion of the ventricle, less ventricular filling (i.e. decreased end-diastolic volume EDV) and a greater diastolic pressure (or filling pressure), resulting in a change in the ventricular diastolic pressure-volume characteristics. In a case of ventricular enlargement and/or the decrease of myocardial function, the left ventricular elastic recoil forces may be diminished, therefore leading to increase of the ventricular filling pressure.

The devices and methods herein involve implanting within the ventricle a device to improve cardiac function. More specifically the device improves cardiac function by reducing left ventricular wall stress, by improving the composite material properties of a left ventricle, by increasing diastolic compliance, by reducing filling pressure, by improving any other suitable factor, and/or by any combination thereof. In one embodiment, the device partitions the patient's ventricle into a functional portion and an excluded, non-functional portion. The method may be used to treat a heart, in particular the left ventricle.

The increase in left ventricular (LV) volume that occurs after myocardial infarction (MI) is increasingly recognized as a potential target for therapeutic intervention. In general, this LV remodeling process is thought to be driven by an increase in stress in the LV wall. Specifically, a compensatory increase in end-diastolic volume is associated with an increase in end-diastolic stress which causes eccentric hypertrophy of myocardium. In addition, increased end-systolic stress in the MI border zone (BZ) may lead to non-ischemic infarct extension and subsequent LV enlargement.

Figure 49A:
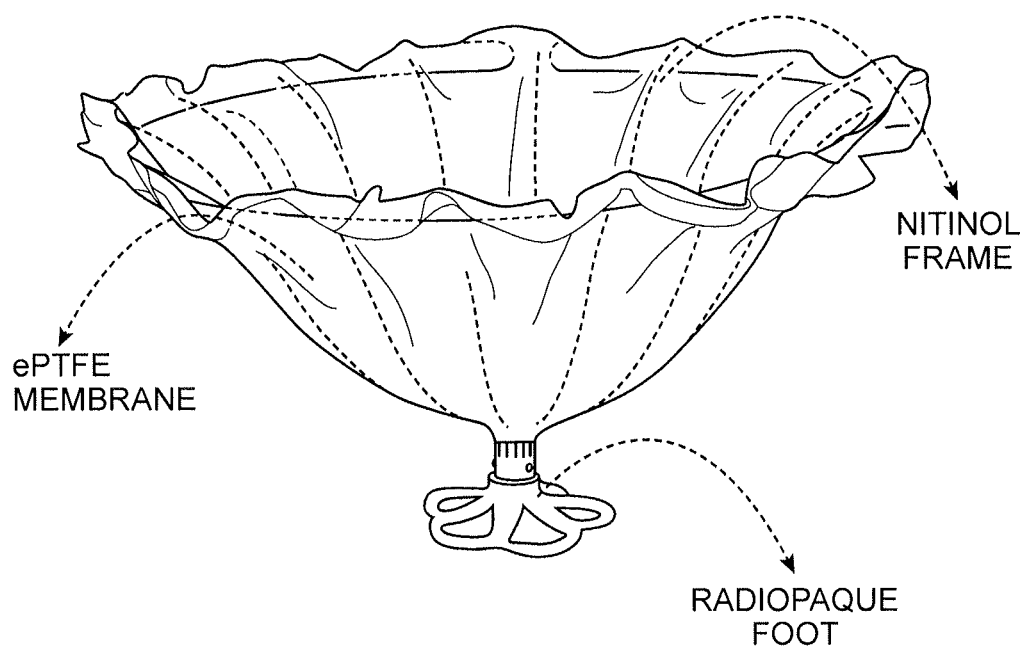
FIGS. 49A and 49B illustrates a device for improving cardiac function of a first preferred embodiment.
Figure 49B:
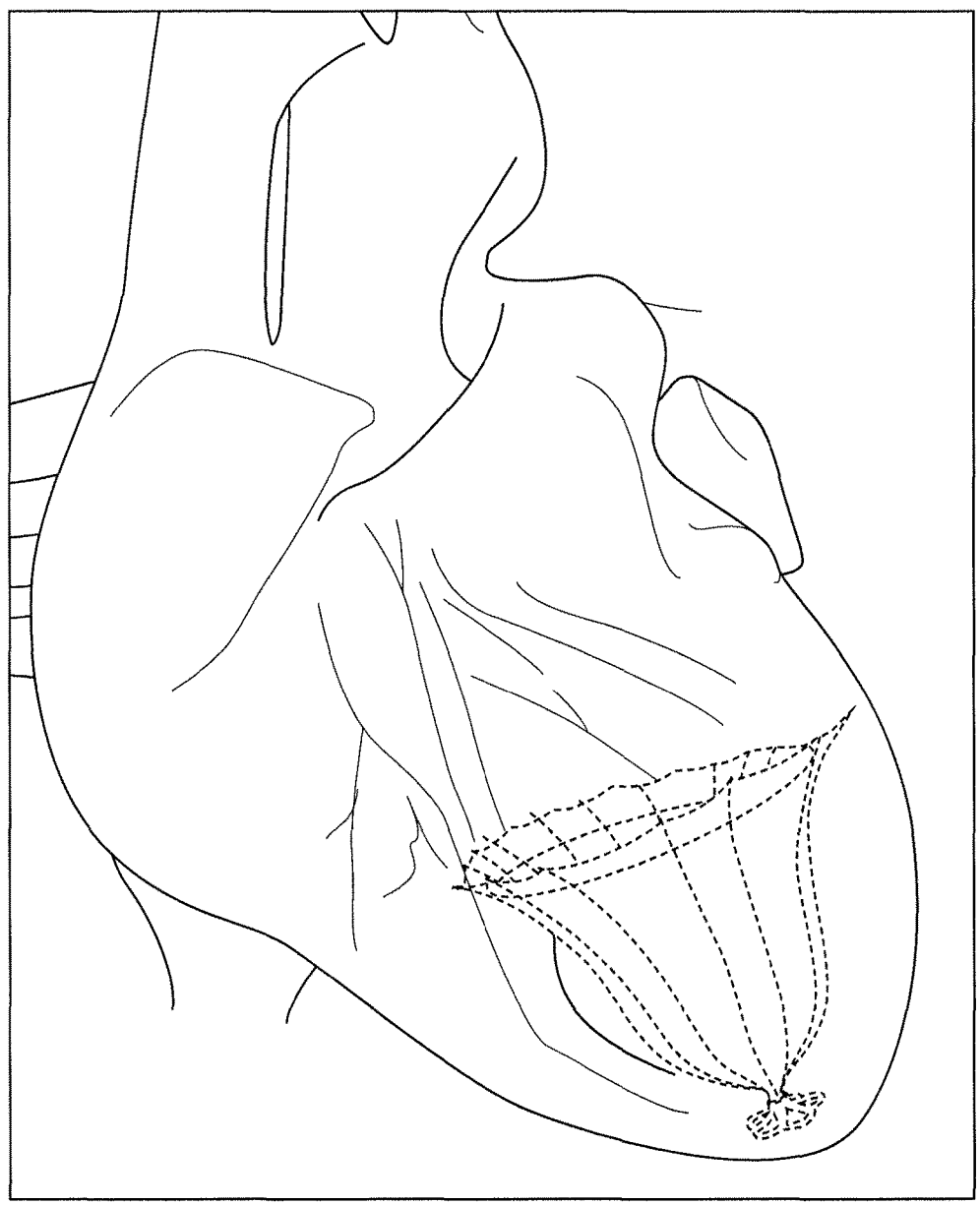

A catheter-based device, as shown in FIG. 49A for example, and system, as described herein may be used to reverse, reduce, prevent and/or treat left ventricular (LV) remodeling, for example, after an antero-apical myocardial infarction (MI). When deployed, as shown in FIG. 49B, the device described herein partitions the LV into one or more upper chambers and one or more lower chambers, thereby reducing LV end-diastolic and end-systolic volumes of the heart. Improvements have been shown in LV ejection fraction, as well as improvements in NYHA class and 6 minute walk Finite element (FE) modeling of the heart and cardiac surgical procedures is becoming more common. For example, FE modeling allows the calculation of LV myofiber stress which can be difficult to measure in vivo. In addition, the FE method allows inverse calculation of the myocardial material parameters, by either manually or automatically adjusting these parameters to match measured LV volume and/or strain.

Described herein is the first patient-specific model capable of simulating a direct interaction between the device described herein and the LV. In this model, the LV was reconstructed from computed tomography (CT) images taken from a patient. In addition, contact modeling and a validated user-defined material law for diastolic and end-systolic myocardial mechanics implemented in the finite element (FE) software LS-DYNA was used to simulate both the entire implantation process and the effects of the device on LV function and regional mechanics. Described herein are methods for simulating such patient-specific effects of the device. Also described herein are the preliminary results from a single patient study employing the device.

Imaging

Figure 45:
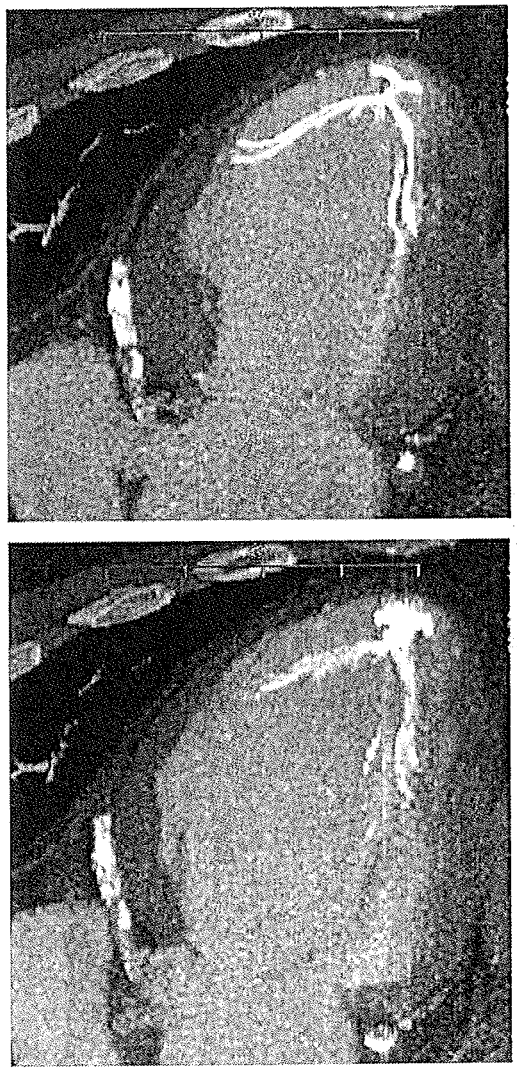
FIGS. 45A-B illustrate CT images of LV 6 months after Device implantation: (a) End-diastole and (b) end-systole in accordance with some embodiments.

Imaging was performed using a 64 slice CT scanner (Siemens Medical, Malvern, Pa.). Image slices were 0.75 mm in width with 0.4 mm overlap. The image sequence was gated to the surface electrocardiogram and there were 10 R wave to R wave phases. A series of long and short-axis images of the LV were reconstructed and analyzed, as shown in FIGS. 45A and 45B). Computed Tomography data acquisition was triggered by the QRS complex of the electrocardiogram.

It will be appreciated by one skilled in the art that the width and overlap of the image slices can be selected to achieve any desired result.

Figure 46:
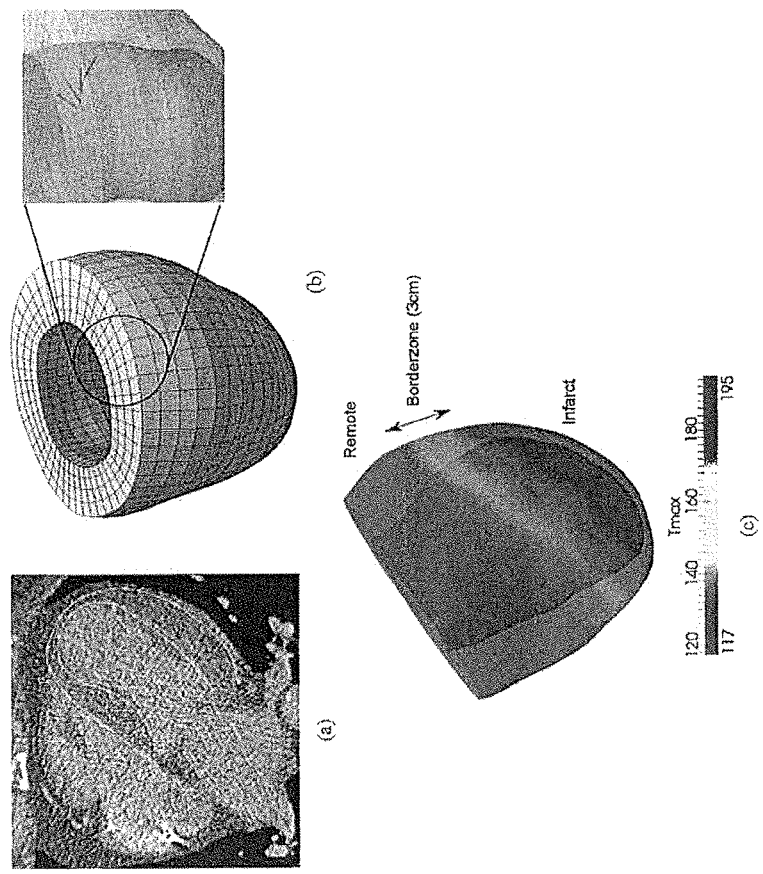
FIGS. 46A-C illustrate construction of a patient-specific finite element LV model: (a) Digitization of the endocardial and epicardial surfaces, (b) fiber orientation in the finite element LV model and (c) regional contractility in the LV with infarct in accordance with some embodiments.

A customized computer implemented program (iContours, Liang Ge, Cardiac Biomechanics Lab, San Francisco, Calif.) based on the medical image processing environment Mevislab (v 2.1, Mevislab, Bremen, Del.) was designed. The program was used to contour the endocardial and epicardial surfaces of the LV, as shown in FIGS. 46A-C. In the illustrated example, end diastole (ED) and end systole (ES) were defined as the images with the maximum and minimum cross sectional area, respectively.

Finite Element Modeling

Finite element models of the LV and device were created based on PRE-OP CT images and device specifications. For example, as shown in FIG. 49A, device specifications may include geometry, dimensions, material properties of the various components, and/or other suitable characteristics of the device To determine the acute effects of the device, implantation of the device was first simulated on an PRE-OP LV model before simulating end-of-diastole (ED) and end-of-systole (ES) of the LV implanted with the device (Virtual-Device case). In a POST-OP case, diastolic and systolic material parameters in the LV model of the Virtual-Device case were adjusted so that the model LV volume aligned with a 6-months POST-OP CT and measured LVEDP data. In each of these 3 cases (PRE-OP, Virtual-Device and POST-OP), myofiber stress at ED and ES, and pump function were calculated. All the simulations were performed using LS-DYNA (Livermore Software Technology Corporation, Livermore, Calif.,).

PRE-OP Finite Element Model of the Left Ventricle

Endocardial and epicardial surfaces were created from LV contours (Rapidform; INUS Technology, Inc, Sunnyvale, Calif.). A space between the endocardial and epicardial surfaces was filled with 3648 8-node trilinear brick elements to generate a volumetric mesh that was 4 elements thick (Truegrid; XYZ Scientific Applications, Inc, Livermore, Calif.) (FIG. 46B).

Cardiac myofiber angles at the epicardium and endocardium were assigned to be −60 degrees and 60 degrees respectively (counterclockwise positive when viewed from the epicardium) with respect to the circumferential direction. The angles varied linearly across the LV wall.

Three distinct material regions were assigned in the LV, namely, an infarcted region, a borderzone region and a remote myocardium zone (e.g., healthy remote region). The infarcted region in the LV was akinetic (e.g., no change in wall thickness in a cardiac cycle), and was defined to as a region where ventricular wall thickness was less than 6 mm. The borderzone (BZ) region (e.g., having reduced contractility) was defined to as a region adjacent to the infarcted region. In some embodiments, the BZ had a width of about 3 cm. The remainder of the LV (e.g., not including the infarcted region and the borderzone region) was defined as a remote myocardium zone, as shown in FIG. 46C.

Material Law and Parameters

Constitutive law describing passive filling of the LV was prescribed to the entire LV using the strain energy function:

$$W = \frac{C}{2}(\exp(b_f E_{ff}^2 + b_t(E_{ss}^2 + E_{nn}^2) + b_{fs}(E_{fs}^2 + E_{sf}^2 + E_{fn}^2 + E_{nf}^2)) - 1).$$

The strain energy function in Equation (1) is transversely isotropic with respect to the local fiber direction. In this equation, C, $b_f$, $b_{fs}$ and $b_t$ are the diastolic myocardial material parameters and $E_{ij}$ with subscripts $\{i,j\} \in \{f,s,n\}$ are the components of the Green strain tensor E where f, s and n denote the fiber, cross-fiber and transverse-fiber directions, respectively. In the illustrative example described herein, the values of the material parameters in the exponent of Equation (1) were obtained from sheep with $b_f$=49.25, $b_{fs}$=17.44 and $b_t$=19.25 in the entire LV. Material parameter C at the infarct ($C_I$) was defined to be ten times stiffer than that in the remote ($C_R$) and in the BZ ($C_{BZ}$) i.e. $C_I$=10$C_R$=$C_{BZ}$. The C-values were then scaled accordingly so that the LV cavity volume at end-diastole (EDV) matched the measurement from CT images.

Assumption of near incompressibility of the myocardium requires the decoupling of strain energy function W into a dilational part U that depends on the Jacobian J of the deformation gradient tensor and a non-dilational part $\tilde{W}$ that depends on $\overline{C}$, which is the deviatoric decomposition of the right Cauchy-Green deformation tensor C (i.e. $C=j^{2/3}\tilde{C}$). The dilational part of W was prescribed the function $$U = \frac{\kappa}{2}(J-1)^2$$

and the resultant second Piola-Kirchkoff (PK2) stress during diastole becomes:

$$S = \kappa(J-1)JC^{-1} + 2J^{-\frac{2}{3}}Dev\left(\frac{\partial \tilde{W}}{\partial \tilde{C}}\right).$$

In Equation (2), κ is the bulk modulus. In the illustrated example, the bulk modulus was prescribed a value of 1040 kg/m3, a value close to that of water. Dev is the deviatoric projection operator:

$$Dev(\cdot) = (\cdot) - \frac{1}{3}([\cdot]:C)C^{-1}.$$

Contraction during systole was modeled by adding an active stress component $T_0$ in the fiber direction f to the RHS of Equation (2) i.e. adding $T_0 f \otimes f$. The active stress $T_0$ that developed during systole is defined by a time-varying elastance model where:

$$T_0 = \frac{1}{2}T_{max}\frac{Ca_0^2}{Ca_0^2 + ECa_0^2}\left(1 - \cos\left(\frac{0.25}{ml_R\sqrt{2E_{ff}+1}+b}+1\right)\pi\right).$$

In Equation (4), the active stress $T_0$ is a function of the fiber strain $E_{ff}$, the stress-free sarcomere length $l_R$, the length dependent calcium sensitivity $ECa_0$, the intracellular calcium concentration Ca0 and the maximum isometric tension achieved at the longest sarcomere length $T_{max}$. The length dependent calcium sensitivity was defined by:

$$ECa_0 = \frac{Ca_{0,max}}{\sqrt{\exp(Bl_R\sqrt{2E_{ff}+1}-l_0)-1}},$$

where $l_0$ is the sarcomere length at which no active tension develops and $Ca_{0,max}$ is the maximum peak intracellular concentration. In the illustrated example, (based on large animal studies), the material constants in the time-varying elastance model were prescribed values $Ca_0$=4.35 μmol/l, $Ca_{0,max}$=4.35 μmol/l, B=4.75 μm$^{-1}$, $l_0$=1.58 μm, m=1.0489 s μm$^{-1}$, b=−1.429 s and $l_R$=1.85 μm.

In the illustrated example, to reflect the regional contractile state of the infarcted LV, $T_{max}$ of the infarct ($T_{max\_I}$) and the remote region ($T_{max\_R}$) were adjusted so that: (a) the predicted LV cavity volume at end-systole (ESV) matched the measurements from CT images and (b) the average difference of the infarct thickness at ED and at ES was zero. The latter criterion was used to reflect akinesis of the infarct. In the illustrated example, across the borderzone, $T_{max}$ was prescribed to vary linearly (from $T_{max\_I}$ to $T_{max\_R}$) with distance measured from the infarcted region.

In the illustrated example, these active and passive constitutive laws were implemented using a user-defined material subroutine in LS-DYNA.

Boundary Conditions

The LV base was constrained from moving in the longitudinal direction (e.g., in the apex-base direction). In addition, the epicardial-basal edge was constrained from moving in any direction. The inner endocardial wall of the LV was loaded based on the measured pressure data presented in the "Clinical data" section. In the illustrated example, pressure at ED (EDP) was prescribed to be 20 mm Hg in both the PRE-OP and VIRTUAL-Device case, and 12 mm Hg in the POST-OP case. Pressure at end-systole (ESP) was prescribed to be 120 mm Hg in each of the three cases.

Device Model

Figure 47:
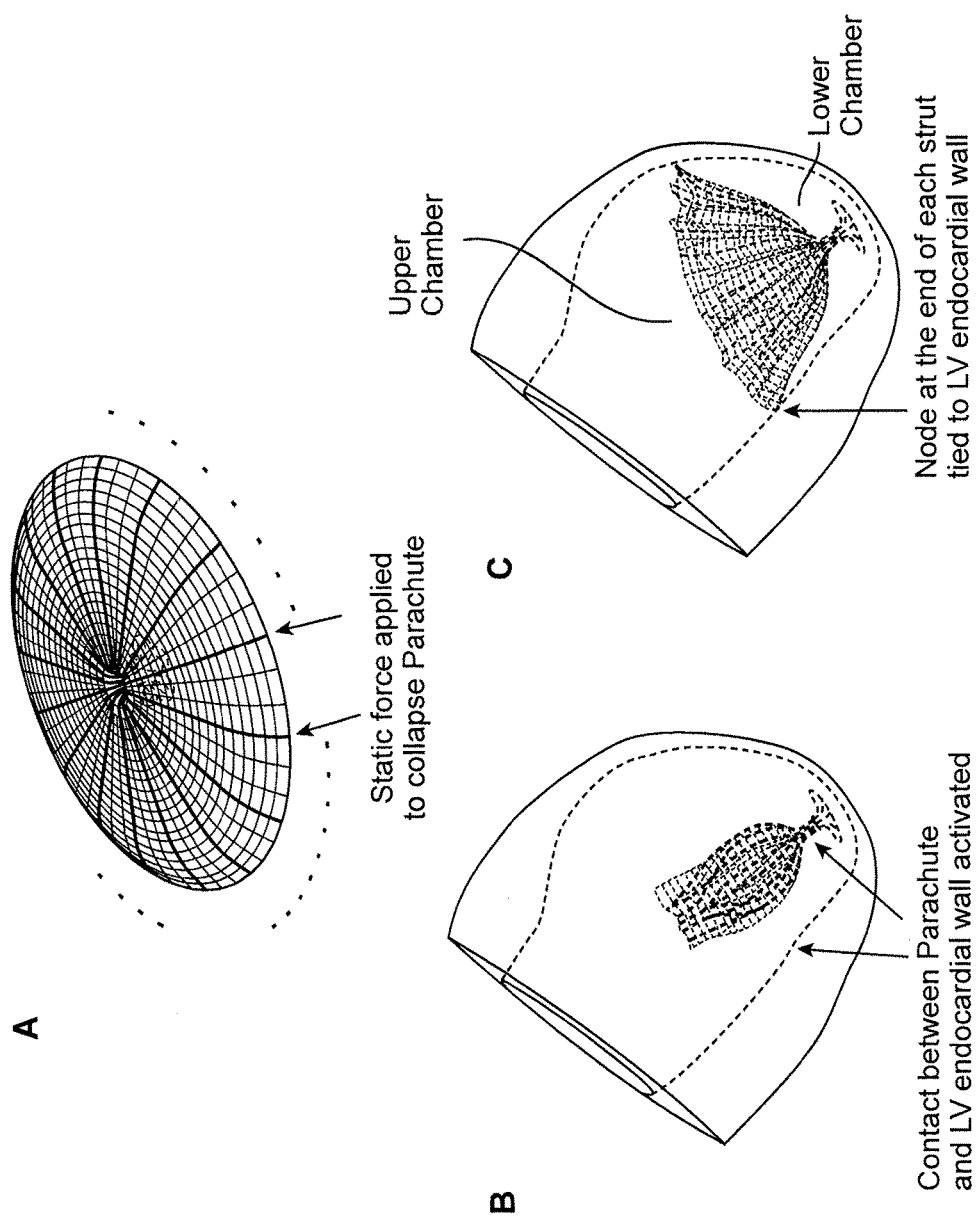
FIGS. 47A-C illustrate virtual implantation of a device into LV: a) Finite element model of the device in which the struts of the Nitinol frame are shown in red, (b) Collapsed device, (c) Implanted device. Refer to text for explanation in accordance with some embodiments.

A finite element model of the device was created, as shown in FIG. 47A The model was created for one specific example of the device which included an expanded polytetrafluoroethylene (ePTFE) membrane coupled to an expanded Nitinol frame, as shown in FIG. 49A. The Nitinol frame included 16 struts and was attached to a radiopaque foot. The approximate diameter of the device was about 85 mm. In the illustrated example, the Nitinol frame, ePTFE membrane and foot were modeled using 496 beam elements, 1152 shell elements and 1110 solid elements, respectively. Isotropic and linear elastic material law (*MAT ELASTIC) was assigned to each of the components (the Nitinol frame, ePTFE membrane and foot). The material parameters of the illustrated example are shown in Table 1.

TABLE 1

Table 1: Material parameters of the different components in the device.
*Unit for the elastic modulus is MPa.

| (1) Component | (2) Elastic Modulus | (3) Poisson Ratio |
|---|---|---|
| (4) Nitinol Frame | (7) $33.73 \times 10^3$ | (10) 0.33 |
| (5) Foot | (8) 20 | (11) 0.45 |
| (6) ePTFE Membrane | (9) 400 | (12) 0.33 |

Virtual Implantation of the Device

In the implantation process, the device is collapsed and delivered percutaneously from the femoral artery by a catheterization technique. Once in position, the device is expanded and the anchor tip of each strut in the device can engage and hook on to the left ventricular endocardial wall. As a result, the struts are not "stress-free" after the device is deployed in the LV.

To account for residual stress in the struts and in the LV after implantation, the implantation process of the device was simulated. First, the device was collapsed by applying a constant follower force at the end of each strut. In the illustrated example, a force of 0.053N was sufficient to deform the device so that the frame did not come into contact with the LV, as shown in FIG. 47B.

Next, the follower force was removed and a contact constraint between the LV endocardium and the device was activated. Consequently, the device expanded and the struts came into contact with the LV endocardium. To simulate the anchor tip of each strut hooking onto the LV endocardial wall after implantation, the nodal tip of each strut was tied to the endocardial wall upon contact, as shown in FIG. 47C. The deployed position of the device in the LV was adjusted based on CT images taken from the same patient 6 months after implantation. The resultant configuration of the implanted device partitioned the LV into two chambers, for example, a lower static chamber containing the infarcted region and an upper functional chamber containing the remote healthy region. Two cardiac phases, for example, end diastole and end systole were simulated using such a configuration.

In the illustrated example, leaks between the upper and lower chambers were found to be negligible based on Doppler echocardiography, EDP and ESP in the lower chamber were adjusted so that the lower chamber has a constant volume of 36.2 ml (based on CT measurements). In the illustrated example, the ESP in the upper chamber was kept at the baseline value of 120 mmHg and the EDP was adjusted to match clinical data as described in the section "Boundary conditions".

Statistical Analysis

Stress and strain were averaged over the modeled elements of each LV region and presented as the average+ standard deviation in each region. A single finite element model based on a patient was employed. In some embodiments, the results obtained are not stochastic and thus statistical tests may therefore not be appropriate.

Clinical Data

The single device procedure studied was performed at the Texas Heart Institute as part of the multi-center, phase 1 'Parachute United States Feasibility Trial' clinical trial. The study protocol was approved by the Texas Heart Institute Institutional Review Board (IRB). Subsequent analysis of radiographic images obtained from the Device patient was approved by the Committee on Human Research of the University of California, San Francisco.

The device was implanted in a single male 52 year old patient who has a 9-year old post large antero-apical MI. The procedure was uneventful and there were no complications at one year follow up. Pre-op New York Heart Association class was 3 and improved to 1 at 1 year.

CT images were obtained before and 6 months after Device implantation. PRE-OP and 6 month POST-OP volumes are given in Table 2.

TABLE 2

| | Lower ED Volume | Upper ED Volume | Total ED Volume | Lower ES Volume | Upper ES Volume | Total ES Volume | Stroke Volume | Lower ED Press. | Lower ES Press. | Upper ED Press. | Upper ES Press. |
|---|---|---|---|---|---|---|---|---|---|---|---|
| CT Scan: PRE-OP | — | — | 222.8 | — | — | 161.0 | 61.8 | — | — | 18.2* | N/A |
| FE Model: PRE-OP | — | — | 205.7 | — | — | 143.4 | 61.3 | — | — | 20 | 120 |
| CT Scan: 6 month POST-OP | 36.2 | 176.7 | 212.9 | 31.8 | 120.3 | 151.8 | 61.2 | N/A | N/A | 12.9* | N/A |
| FE Model: VIRTUAL-Device | 35.7 | 163.1 | 198.8 | 32 | 111.1 | 143.1 | 55.7 | 7.74 | 114.3 | 20 | 120 |
| FE Model: 6 month POST-OP Device | 38.2 | 166.3 | 204.5 | 31.8 | 113.4 | 145.2 | 59.3 | 5.4 | 114.3 | 12 | 120 |

Table 2, illustrates an example of left ventricular volumes and pressures before and after device implantation. (*) denotes the average value measured in 10 other patients as described in the "Clinical data" section. Pressures in the PRE-OP cases correspond to the entire LV chamber which is not partitioned Note that the acute device effect was substantially mechanical. The chronic device effect was achieved by adjusting the acute model to match LV volumes and pressures obtained at 6 months. ED=end-diastole, ES=end-systole, Lower=lower chamber, Upper=upper chamber. Volume units are [ml] and pressure units are [mm Hg].

In the illustrated example, total LV volume was reduced at 6 months by 4.4 and 5.7% at ED and ES respectively. On the other hand, when the comparison was made between the volume of the functioning chamber at 6 months POST-OP (upper chamber) and that at PRE-OP (entire LV chamber), there was a reduction of 20.7 and 25.3% at ED and ES, respectively, after implantation. PRE-OP ejection fraction was 27.7% and upper chamber ejection fraction at 6 months POST-OP was 31.9%. Stroke volume was essentially unchanged at 6 months POST-OP.

In ten other patients that underwent the device procedure as part of the initial multi-center, phase 1 'Parachute Trial', LVEDP was measured to be 18.2+82 and 12.9+4.5 mm Hg (p<0.05) at pre- and 6 month post-op, respectively.

Pre-OP Model

Regional LV material parameters assigned to the PRE-OP model are shown in Table 3 and the resultant regional variation of contractility $T_{max}$ is shown graphically in FIG. 46C. In the illustrated example, contractility of the infarcted region (117 kPa) was 60% that of the remote region (195 kPa) in order for the average difference between the infarct thickness at ED and at ES to be zero. Thus, the contractility in the 3 cm borderzone region varied linearly with distance from the infarcted region with values between 117 to 195 kPa.

The finite element model of the PRE-OP LV example, as shown in FIG. 46C closely resembles the PRE-OP CT images showing the thin antero-apical infarcted region as shown in FIG. 46A. As seen in Table 2, PRE-OP LV volume at ED and ES was within 7.7 and 10.9% of the PRE-OP CT data, respectively.

Acute Mechanical Effect of Device (VIRTUAL-Device)

The VIRTUAL-Device model example illustrated in FIG. 47C qualitatively resembles the CT images taken 6 months after implantation, as shown in FIGS. 45A and 45B. It will be appreciated from the figure and disclosure herein, that the apical infarcted region and part of the borderzone region were covered by the device after implantation. Also shown in FIG. 49B. In the illustrated example, the total resultant contact force exerted by the device on the myocardium after implantation is 2.3N.

The effects of VIRTUAL-Device on LV volumes and pressures are shown in Table 2. First, to maintain a lower chamber volume of 36.2 ml throughout the cardiac cycle, the lower chamber (region below the device) pressure was predicted to be less than that in the upper chamber, which was held equal to that at baseline. At ED and ES, the lower chamber pressure was predicted to be 61.3% and 4.8% lower, respectively.

Next, the VIRTUAL-Device caused a reduction in total LV volume of 3.4 and 0.2% at ED and ES respectively and, as a result, stroke volume decreased by 9.9%.

Chronic Effect of Device (6 Month POST-OP)

To better match the 6 months POST-OP CT and measured LVEDP data (for example, the measured stroke volume and the decrease in the measured LVEDP), the LV material parameters were adjusted. The adjusted parameters are shown in Table 3.

TABLE 3

|  | Infarct passive stiffness (C_I) | Remote passive stiffness (C_R) | Infarct contractility (Tmax_I) | Remote contractility (Tmax_R) |
|---|---|---|---|---|
| FE Model: PRE-OP | 2.75 | 0.275 | 117 | 195 |
| FE Model: VIRTUAL-Device | 2.75 | 0.275 | 117 | 195 |
| FE Model: 6 month POST-OP Device | 1.6 | 0.16 | 117 | 195 |

Table 3 illustrated the left ventricular regional material parameters with units shown in kPa. Briefly, a 41.8% reduction in passive stiffness led to a POST-OP model with total LV volume at ED and ES that was within 3.9 and 4.3% respectively of the POST-OP CT data. In addition, POST-OP model stroke volume was now within 4% of the POST-OP imaging data.

Myofiber Stress

In the illustrated example, the residual myofiber stress in the LV immediately after implantation of the Device is 0.06 kPa. The effects of device on LV regional myofiber stress at ED and ES are tabulated in Table 4 and shown in FIGS. 48A and 48B.

TABLE 4

|  | Lower Stress at ED | Upper Stress at ED | Total Stress at ED | Lower Stress at ES | Upper Stress at ES | Total Stress at ES |
|---|---|---|---|---|---|---|
| FE Model: PRE-OP | 11.4 ± 6.4 | 5.7 ± 3.9 | 8.3 ± 5.9 | 65.9 ± 40.2 | 30.8 ± 20.1 | 47.1 ± 35.6 |
| FE Model: VIRTUAL-Device | 5.3 ± 2.8 | 5.8 ± 3.6 | 5.6 ± 3.2 | 63.2 ± 37.6 | 31.1 ± 19.6 | 45.5 ± 33.3 |
| FE Model: 6 month POST-OP Device | 4.8 ± 2.6 | 4.2 ± 2.7 | 4.5 ± 2.7 | 65.1 ± 39.4 | 31.4 ± 20.5 | 47.0 ± 35.0 |

Table 4 illustrates an example of the effect of the device on left ventricular myofiber stress with unit shown in kPa.

Because the left ventricular wall at the apical infarcted region was substantially thinner than that in the remote region, myofiber stress was elevated in antero-apical region of the LV in the PRE-OP model. Specifically, stress in the apical region (lower chamber) was 98 and 114% higher than in the remote myocardium region (upper chamber).

As a result of the smaller lower chamber pressure at ED in the POST-OP model, the average ED myofiber stress in the lower chamber was reduced by 57.2% (from 11.4±6.4 to 4.8±2.6 kPa). The average myofiber stress in the upper chamber was substantially unchanged in the VIRTUAL-Device case but after diastolic stiffness and loading at ED were adjusted accounting for the improvement in diastolic compliance to match clinical data in the POST-OP model, upper chamber stress at ED was reduced by 26.3% (from 5.7±3.9 to 4.2±2.7 kPa). As a consequence, the combined average myofiber stress at ED was 45.8% lower POST-OP when compared to the PRE-OP model.

In contrast, the average ES myofiber stress in the lower chamber decreased only slightly in the VIRTUAL-Device case and was essentially unchanged in the POST-OP model. Upper chamber stress at ES was also unchanged. As a consequence, the combined average myofiber stress at ES in the POST-OP model was not different than PRE-OP.

It will be appreciated from the disclosure herein that the device causes a substantial reduction in myofiber stress at ED by improving diastolic compliance. Considering only the acute mechanical effect (VIRTUAL-Device), stress at ED in the lower chamber was reduced. However, after adjusting to better match POST-OP CT and LVEDP data, stress at ED was reduced in both the upper and lower LV chambers.

Device Model

Disclosed herein is the first patient-specific mathematical model of a human LV implanted with the device described herein. The model provides unexpected superior results because in addition to simulating a beating LV implanted with the device, the entire implantation process of the device was also simulated to account for possible influence of the residual stresses on the LV function and regional myofiber stress. It will be appreciated from the disclosure herein that the residual stress in the LV is small (for example, about 2 orders of magnitude smaller than the ED stress). This result is also consistent with the results which show that the total contact force of 2.3N exerted by the device on the LV is small compared to the total pressure force (for example, product of pressure and endocardial surface area) exerted on the LV. In the VIRTUAL-Device example, the total pressure force is about 30N and 200N at ED and ES, respectively.

Effects on Myofiber Stress

Figure 48:
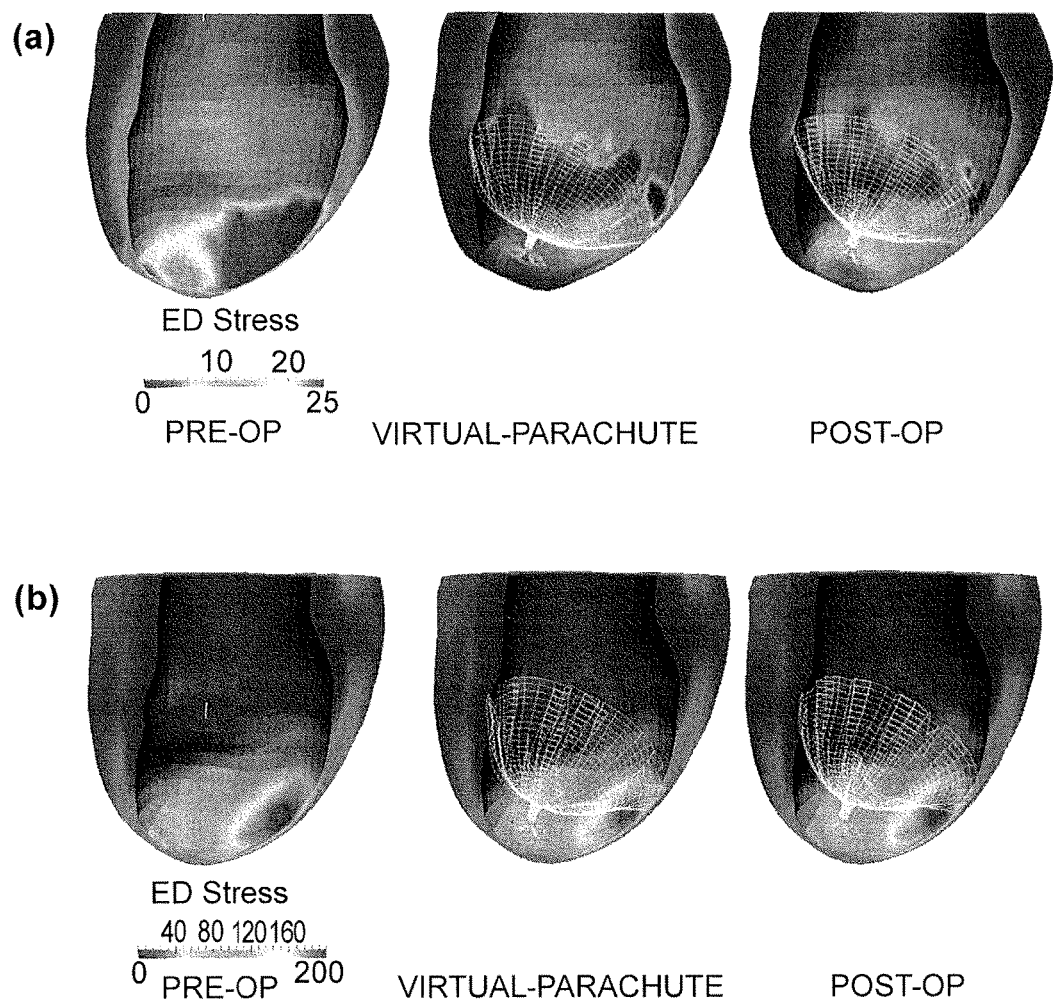
FIGS. 48A-B illustrates the effect of device on an LV regional myofiber stress: (a) end-diastole and (b) end-systole (units of color scale in kPa) in accordance with some embodiments.

The results from the single patient study disclosed herein show that the therapeutic effect of the device came from lowering the EDP acting on the infarcted region in the partitioned lower chamber. The lowered pressure acting on the infarcted region reduced myofiber stress in the LV at ED. Considering the POST-OP example, the average myofiber stress (across the entire LV) at ED was reduced by 45.8% and the myofiber stress distribution at ED became more homogeneous, as shown in FIGS. 48A and 48B. Without being limited in theory, given that the elevated myofiber stress is widely believed to be responsible for adverse cardiac remodeling, and is usually found at the thin infarcted region, it is believed that the reported therapeutic effects are an outcome of the local reduction in the infarct myofiber stress as predicted by according to the disclosure herein.

Effects on Left Ventricular Pump Function

On the other hand, the simulation results disclosed herein show that both EDV and ESV were reduced, at least acutely, after the device was implanted into the LV. Because the reduction in the EDV was larger than in the ESV, stroke volume was reduced as a result (by 9.9%). A reduction in stroke volume is also found in simulations of other treatments such as Surgical Ventricular Restoration.

Left Ventricle with Infarcted Region

The LV borderzone region was modeled as a region having contractility that varies linearly with distance from the infarcted region based on the findings, as described herein, that such a borderzone model produces strain results that better match the in-vivo strain measurements. Thus, in some embodiments, the contractility of the entire LV depends on two parameters, for example, the contractility in the akinetic infarct ($T_{max\_I}$) and the contractility in the remote region ($T_{max\_R}$). It was determined that the contractility in the akinetic infarcted region is 60% of that in the remote region. This result is close to the result found in sheep. In the study by Dang et al. 50% of the myocytes is needed to produce akinesis when the infracted region diastolic stiffness $C_1$ is 10 times that at the remote region $C_R$ i.e. $C_I=10C_R$. The relationship ($C_I=10C_R$), which was used in this example, was based on sheep studies.

It will be appreciated from the disclosure herein that to evaluate the effects of the device on LV, the analysis was simplified by modeling the Nitinol strut using beam elements. It will also be appreciated that the infarcted region was determined based on the LV wall thickness instead of using the more accurate delayed hyper-enhancement technique. It will also be appreciated that the lack of LV regional in-vivo strain measurements meant the model could not be validated against local myocardial strain. It will also be appreciated that the actual lower chamber pressure measurement (which can be difficult to obtain) to corroborate the results on the lower chamber pressure was not attainable.

Disclosed herein is the first realistic finite element model of the device described herein implanted in a human LV, including the implantation process, and quantified effects of such a treatment on both LV function and regional myofiber stress. The results of this single-patient study described herein show that the device reduces the LV end-diastolic myofiber stress, particularly in the infarcted region.

The systems may be comprised of various modules as discussed herein. As can be appreciated by one of ordinary skill in the art, each of the modules comprises various sub-routines, procedures, definitional statements and macros. Each of the modules are typically separately compiled and linked into a single executable program. Therefore, the description of each of the modules is used for convenience to describe the functionality of the preferred system. Thus, the processes that are undergone by each of the modules may be arbitrarily redistributed to one of the other modules, combined together in a single module, or made available in, for example, a shareable dynamic link library.

As used herein, "instructions" refer to computer-implemented steps for processing information in the system. Instructions can be implemented in software, firmware or hardware and include any type of programmed step undertaken by components of the system.

A "microprocessor" or "processor" may be any conventional general purpose single- or multi-core microprocessor. In addition, the microprocessor may be any conventional special purpose microprocessor such as a digital signal processor or a graphics processor.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

While certain exemplary embodiments have been described and shown in the accompanying drawings, it is to be understood that such embodiments are merely illustrative and not restrictive of the current invention, and that this invention is not restricted to the specific constructions and arrangements shown and described since modifications may occur to those ordinarily skilled in the art.

What is claimed is:

1. A method of treating a patient suffering from a heart condition, the method comprising:
    advancing, into a ventricle of a heart, a collapsed device comprising:
        a plurality of radially expandable resilient ribs connected at their distal ends to a central hub, and
        a membrane coupled to said ribs;
    expanding said ribs in said ventricle of said heart, thereby partitioning said ventricle with said membrane; and
    securing said device to opposing walls of said ventricle, wherein when expanded and secured, said ribs exert an outward force on said opposing walls of said ventricle, thereby assisting in expanding said ventricle during diastole, and providing elastic support between said opposing ventricular walls, thereby improving diastolic compliance.

2. The method of claim 1, wherein advancing further comprises advancing the collapsed device percutaneously.

3. The method of claim 1, wherein by improving diastolic compliance, myofiber stress in the ventricle is reduced.

4. The method of claim 1, wherein the method enhances, improves, or restores a composite material property of the ventricle of the heart.

5. The method of claim 1, wherein the method reduces a filling pressure of the heart.

6. The method of claim 1, further comprising augmenting movement of said walls of said ventricle during diastole.

7. The method of claim 6, wherein augmenting movement of said walls of said ventricle during diastole comprises harnessing motion of a healthy portion of said ventricle to create motion in an unhealthy portion of said ventricle.

8. The method of claim 1, further comprising decreasing stress in said walls of said ventricle, thereby limiting remodeling of said heart.

9. The method of claim 1, further comprising reducing diastolic pressure of said ventricle.

10. The method of claim 1, further comprising improving a pressure-volume relationship of said ventricle.

11. The method of claim 1, further comprising supporting a weakened cardiac wall.

12. A method of treating a patient suffering from a heart condition, the method comprising:
    advancing a collapsed device comprising a plurality of radially expandable resilient ribs connected at their distal ends to a central hub, said device further comprising a membrane coupled to said ribs;
    expanding said ribs in a left ventricle of said heart; partitioning said left ventricle with said membrane; and
    securing said device to opposing walls of said ventricle thereby separating said left ventricle into a main functioning portion and a secondary, essentially non-functioning portion and thereby reducing pressure acting on the non-functioning portion.

13. The method of claim 12, wherein advancing further comprises advancing the collapsed device percutaneously.

14. The method of claim 12, wherein by reducing pressure acting on the non-functioning portion of the left ventricle, myofiber stress in the left ventricle is reduced.

15. The method of claim 12, wherein the non-functioning portion of the left ventricle is an infarcted region of the left ventricle.

16. A method of treating a patient with a diseased left ventricle, the method comprising:
    advancing percutaneously to the left ventricle an implant having:
        an expandable frame formed from a plurality of ribs extending from a first end of a central hub,
        a support component extending from a second end of the central hub, and
        a membrane secured to the plurality of ribs;
    aligning the implant with the left ventricular outflow tract;
    expanding the implant within the left ventricle; and
    securing the expanded implant within the left ventricle, wherein, when extended from the second end of the central hub, the support component atraumatically contacts an apex of the left ventricle.

17. The method of claim 16, further comprising sealing a peripheral portion of the membrane against the left ventricle wall.

18. The method of claim 17, wherein securing the expanded implant within the left ventricle isolates an akinetic region of the heart from a functional portion of the ventricle.

19. The method of claim 17, wherein securing the expanded implant within the left ventricle isolates an enlarged region of the heart from a functional portion of the ventricle.

20. The method of claim 16, further comprising abutting the support component against the ventricle wall and spacing an interior portion of the membrane from the ventricle wall.

21. The method of claim 20, wherein the interior portion of the membrane is adapted to provide a trampoline effect wherein a pressure receiving face of the interior portion of the membrane is configured to move in a first direction relative to a wall of the ventricle during systole and to recoil in a second direction during diastole.

22. The method of claim 16, wherein aligning the implant with the left ventricular outflow tract comprises aligning the implant to receive flow of blood exiting the mitral valve and redirecting the flow of blood towards the aortic valve.

23. The method of claim 16, wherein aligning comprises aligning a central axis through the central hub of the implant with the left ventricular outflow tract.

24. A method of treating a left ventricle of a patient suffering from a heart condition, the method comprising:
    percutaneously advancing to the left ventricle an implant having a frame formed from a plurality of ribs and a membrane secured to the frame; and
    securing the implant within the left ventricle so that the membrane cyclically and resiliently moves relative to a wall of the left ventricle during a cardiac cycle so that a gap between the membrane and the wall of the left ventricle decreases and increases in a trampoline-like fashion.

25. The method of claim 24, wherein percutaneously advancing comprises collapsing the implant and expanding the implant after advancing into the left ventricle.

26. The method of claim 24, further comprising securing an end of each of the plurality of ribs against the wall of the left ventricle.

27. The method of claim 24, wherein securing comprises securing the implant at the apex of the left ventricle.

28. The method of claim 24, wherein securing the implant comprises securing the implant so that the membrane and frame move relative to the wall of the left ventricle during a cardiac cycle.

29. The method of claim 24, wherein securing the implant within the left ventricle comprises securing an edge of the implant to the left ventricle so that a central portion of the implant is separated from the wall of the left ventricle and so that the implant may elastically recoil relative to the wall during a cardiac cycle.

30. The method of claim 24, further comprising aligning the implant with an axis extending through an aortic valve and along the left ventricular outflow tract.

* * * * *